(12) United States Patent
Matsushita et al.

(10) Patent No.: US 12,121,682 B2
(45) Date of Patent: Oct. 22, 2024

(54) METHOD FOR RECYCLING USED BALLOON CATHETER, BALLOON CATHETER, AND INFORMATION PROCESSING SYSTEM

(71) Applicant: KANEKA CORPORATION, Osaka (JP)

(72) Inventors: Keisuke Matsushita, Tokyo (JP); Ryoji Nakano, Settsu (JP)

(73) Assignee: KANEKA CORPORATION, Osaka (JP)

( * ) Notice: Subject to any disclaimer, the term of this patent is extended or adjusted under 35 U.S.C. 154(b) by 1060 days.

(21) Appl. No.: 17/042,483

(22) PCT Filed: Jan. 15, 2019

(86) PCT No.: PCT/JP2019/000921
§ 371 (c)(1),
(2) Date: Sep. 28, 2020

(87) PCT Pub. No.: WO2019/187505
PCT Pub. Date: Oct. 3, 2019

(65) Prior Publication Data
US 2021/0023348 A1 Jan. 28, 2021

(30) Foreign Application Priority Data
Mar. 29, 2018 (JP) .................. 2018-065251

(51) Int. Cl.
*A61M 25/10* (2013.01)
*G16H 40/40* (2018.01)

(52) U.S. Cl.
CPC ......... *A61M 25/1011* (2013.01); *G16H 40/40* (2018.01); *A61M 2025/1054* (2013.01); *A61M 2205/60* (2013.01)

(58) Field of Classification Search
CPC ...... A61M 25/1011; A61M 2025/1054; A61M 2205/60; A61M 2025/0019; G16H 40/40
See application file for complete search history.

(56) References Cited

U.S. PATENT DOCUMENTS 4,721,123 A * 1/1988 Cosentino ........... A61M 25/002
134/57 R
5,135,488 A 8/1992 Foote et al.
(Continued)

FOREIGN PATENT DOCUMENTS

JP    6-811172 A    12/1994
JP    3115667 U    11/2005
(Continued)

OTHER PUBLICATIONS

Japanese Decision to Grant a Patent (including an English translation thereof) issued in the corresponding Japanese Patent Application No. 2019-123427 on Jan. 10, 2023.
(Continued)

*Primary Examiner* — Bradley J Osinski
(74) *Attorney, Agent, or Firm* — Birch, Stewart, Kolasch & Birch, LLP

(57) ABSTRACT

A method for recycling a used balloon catheter includes accepting a used balloon catheter. The balloon catheter includes a detector that detects a state value including at least a pressure generated in a pipe path formed within the balloon catheter and a storage that stores a result of detection of the state value by the detector. The method includes determining at least one of reusability of the used balloon catheter and a method of recycling the used balloon catheter, based on the result of detection stored in the storage of the used balloon catheter.

11 Claims, 45 Drawing Sheets

(56) References Cited

U.S. PATENT DOCUMENTS

| | | | | |
|---|---|---|---|---|
| 5,458,571 | A | * 10/1995 | Lampropoulos | G01D 9/00 604/509 |
| 2017/0157371 | A1 | 6/2017 | Tsuneoka et al. | |
| 2018/0168463 | A1* | 6/2018 | Morris | G16H 20/30 |

FOREIGN PATENT DOCUMENTS

| | | |
|---|---|---|
| JP | 2015-142632 A | 8/2015 |
| JP | 2016-515410 A | 5/2016 |
| WO | WO 90/11040 A2 | 10/1990 |
| WO | WO 93/06776 A1 | 4/1993 |
| WO | WO 2014/145411 A2 | 9/2014 |
| WO | WO 2018/009705 A1 | 1/2016 |

OTHER PUBLICATIONS

International Search Report (PCT/ISA/210) issued in PCT/JP2019/000921 mailed on Apr. 2, 2019.
Written Opinion (PCT/ISA/237) issued in PCT/JP2019/000921 mailed on Apr. 2, 2019.

* cited by examiner

FIG.12
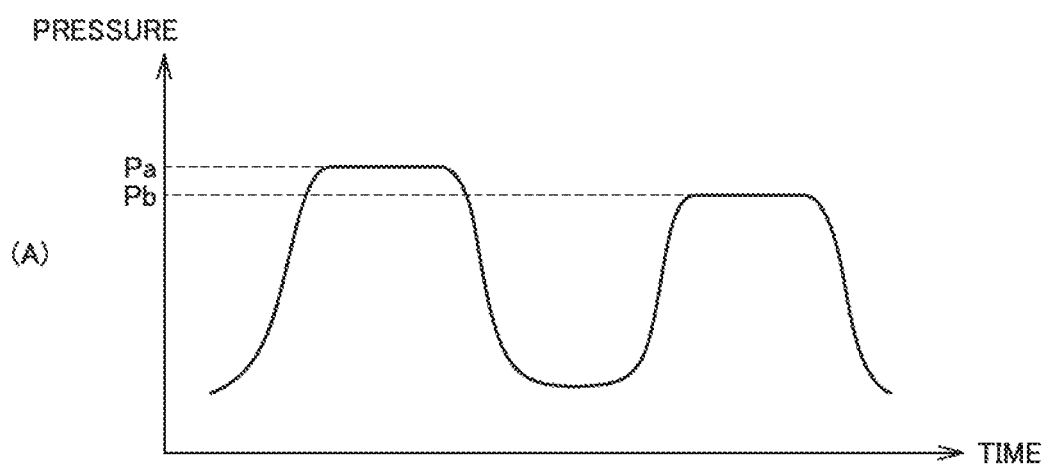
(A)
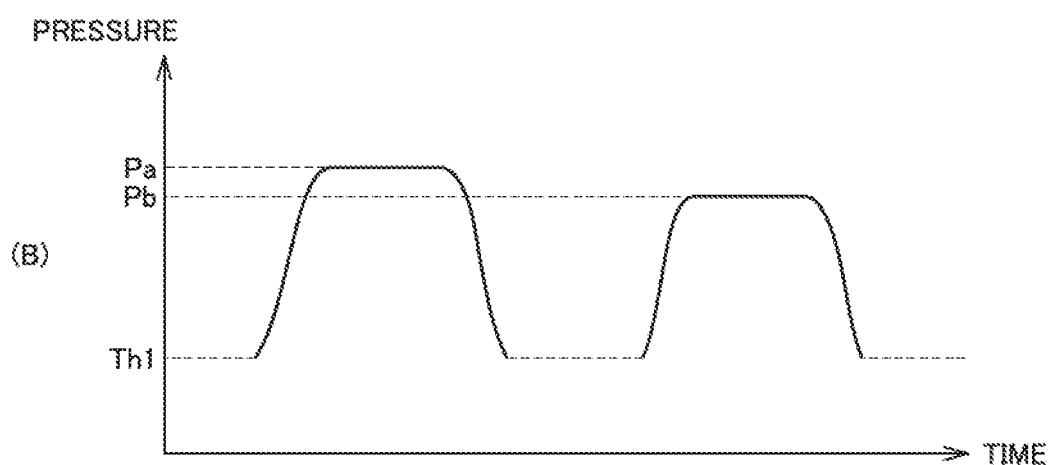
(B)

FIG.26
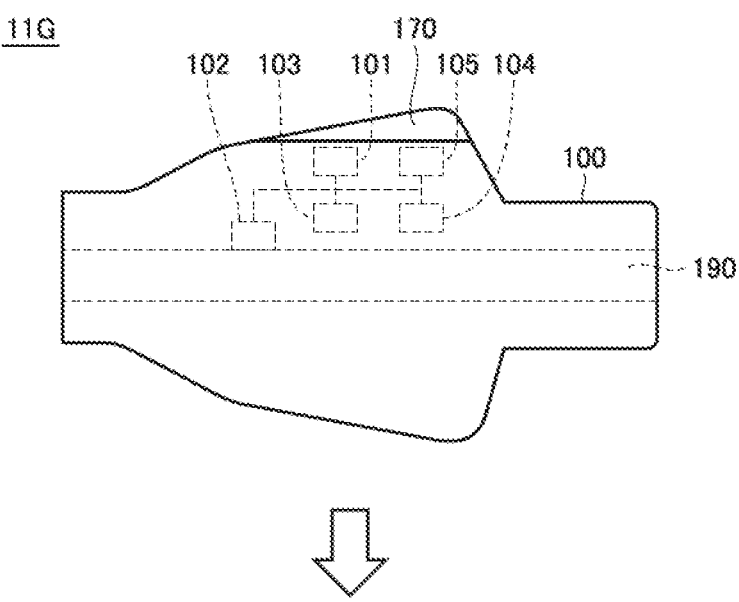
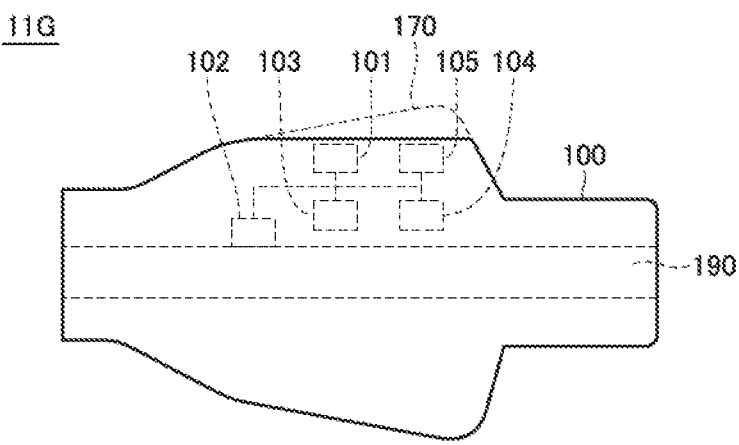

FIG.32
(A)
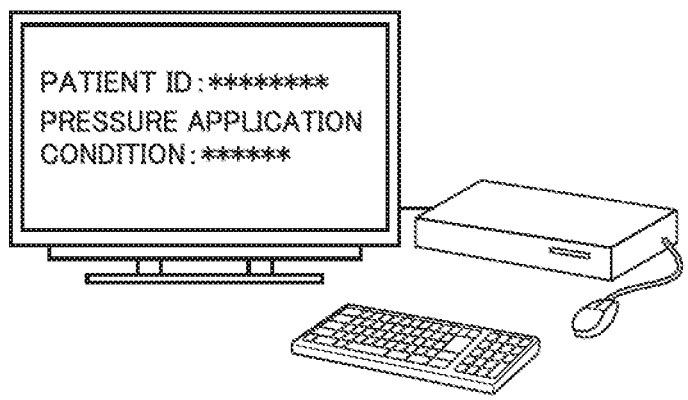
(B)
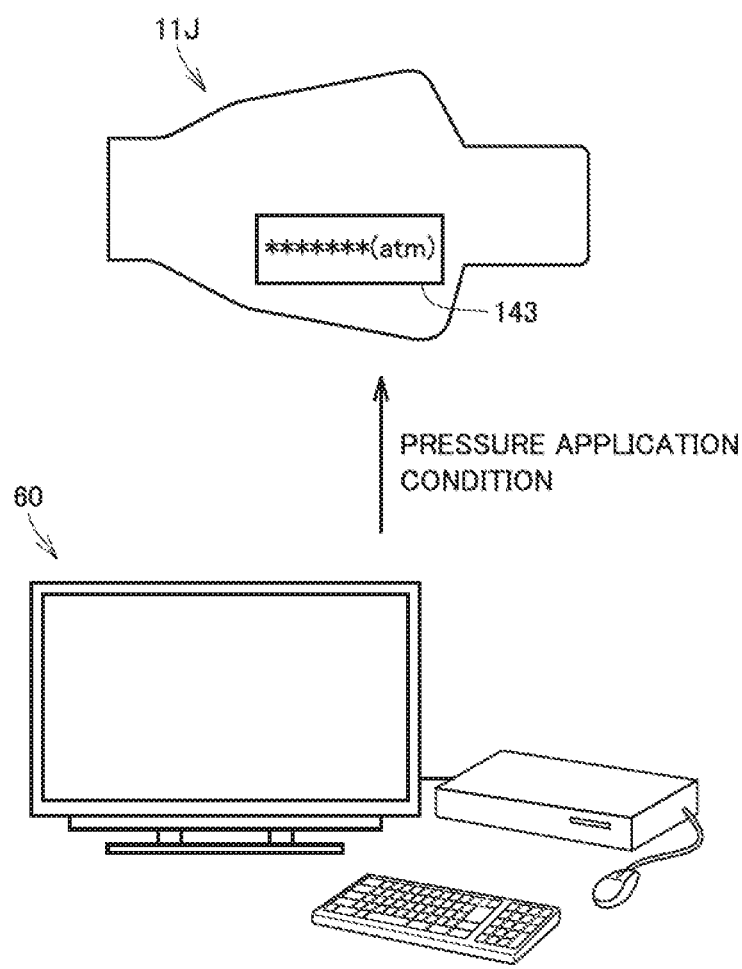

FIG.37

CATHETER INSPECTION/TREATMENT RECORD PAPER — 980

DATE OF INSPECTION: MM DD, YYYY  
MEDICAL CHART NUMBER: *********  
NAME:    
DATE OF BIRTH: MM DD, YYYY

WEIGHT: ***kg  
CRE: ** mg/cl  
E-GFR: *****

| TIME | CLINICAL COURSE RECORD | MEDICATION | NURSING RECORD |
|---|---|---|---|
| 12:00 | CARRIED IN ANESTHESIA | 12:30 HEPARIN | CHEST *** |
| 12:32 | CATHETER **** ******** | | |
| 12:45 | LOWER LIMB ANGIOGRAPHY | | |
| | ********* CATALOG No. ****, LOT No. **** GUIDING CATHETER FOR CORONARY ARTERY — 981 | | |
| | **** GUIDE WIRE —********* — 982 | | |

METHOD FOR RECYCLING USED BALLOON CATHETER, BALLOON CATHETER, AND INFORMATION PROCESSING SYSTEM

TECHNICAL FIELD

The present invention relates to a method for recycling a used balloon catheter, a balloon catheter, and an information processing system including a balloon catheter.

BACKGROUND ART

A system that monitors inflation (which is also referred to as "expansion") of a balloon catheter and shows data on inflation has conventionally been known.

For example, WO90/11040 (PTL 1) discloses a system which assists in control of balloon catheter inflation pressures and automatically records balloon catheter inflation data. The system includes a syringe (an inflation device) and a controller connected to the syringe.

The syringe is connected to a balloon catheter and injects a sterile solution into a pipe path of the balloon catheter. The syringe includes a transducer that monitors a fluid pressure applied to the balloon catheter by the syringe.

The controller receives an electrical signal output from the transducer. The controller shows and stores magnitude of the fluid pressure applied to the balloon catheter and a duration for which the fluid pressure is applied to the balloon catheter, based on the received electrical signal.

CITATION LIST

Patent Literature

PTL 1: WO90/11040

SUMMARY OF INVENTION

Technical Problem

The balloon catheter is removed from the inflation device after surgery for a patient. Thereafter, the balloon catheter is typically disposed of.

In consideration of costs and an environment, however, the balloon catheter is preferably reused. In this case, a state of use of the used balloon catheter should be taken into consideration.

The present disclosure was made in view of the problem above, and the present disclosure provides a method of recycling a balloon catheter in consideration of a state of use of the balloon catheter, a balloon catheter therefor, and an information processing system including the balloon catheter.

Solution to Problem

According to one aspect of the present disclosure, a method for recycling a used balloon catheter includes accepting a used balloon catheter. The balloon catheter includes a detector that detects a state value including at least a pressure generated in a pipe path formed within the balloon catheter and a storage that stores a result of detection by the detector. The method includes determining at least one of reusability of the used balloon catheter and a method of recycling the used balloon catheter based on the result of detection stored in the storage of the used balloon catheter.

According to another aspect of the present disclosure, a balloon catheter with a pipe path includes a detector that detects a state value including at least a pressure generated in the pipe path, a storage that stores a result of detection by the detector, and an interface unit for output of the result of detection stored in the storage.

According to yet another aspect of the present disclosure, an information processing system includes a balloon catheter including a pipe path and an information processing apparatus. The balloon catheter detects a state value including at least a pressure generated in the pipe path, stores a result of detection in a memory, and outputs the stored result of detection to the outside. The information processing apparatus receives the result of detection output to the outside.

Advantageous Effects of Invention

According to the configuration, a balloon catheter can be recycled in consideration of a state of use of the balloon catheter.

BRIEF DESCRIPTION OF DRAWINGS

FIG. 12 is a diagram for illustrating overview of exemplary data detected by a detector of the balloon catheter.

FIG. 26 is a diagram representing a hub of the balloon catheter.

FIG. 32 is a diagram for illustrating a method of notifying a doctor of a pressure application condition.

FIG. 37 is a diagram representing exemplary paper for recording catheter inspection and treatment.

DESCRIPTION OF EMBODIMENTS

Figure 1:
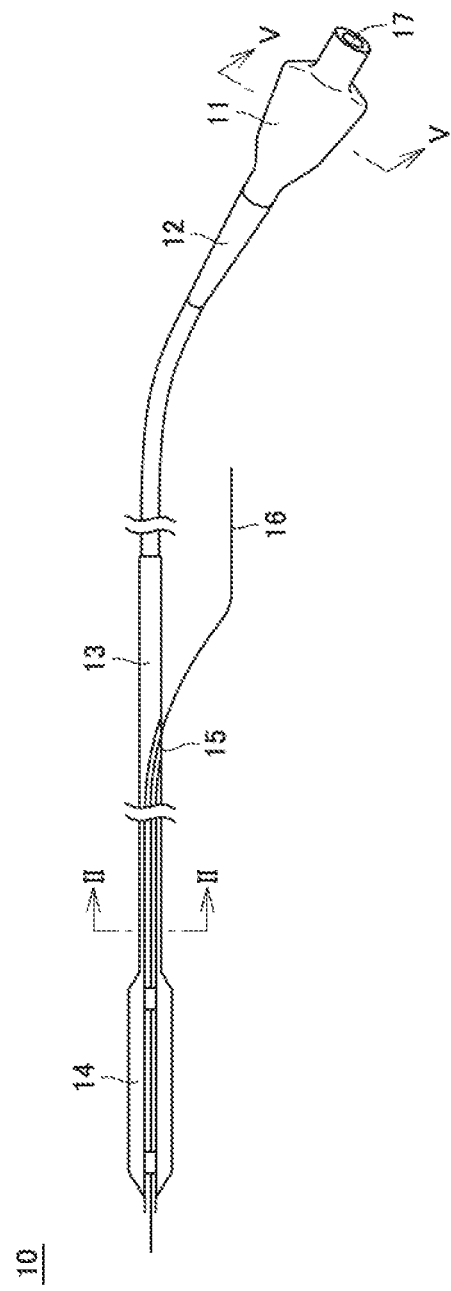
FIG. 1 is a diagram for illustrating a schematic configuration of a balloon catheter.

A balloon catheter in which application of a pressure is required, an information processing system including a balloon catheter, and a method for recycling a used balloon catheter will specifically be described below with reference to embodiments.

The balloon catheter, the information processing system, and the method for recycling the used balloon catheter according to the present disclosure, however, are not restricted by the embodiments, and modification and combination can be made within the scope in conformity with the gist of the disclosure. Hatching, members, or signs may not be provided in each drawing for the sake of convenience. A dimension of various members in the drawings may be different from an actual dimension, because assistance for understanding of features of the present disclosure is prioritized.

"A. Acquisition of Data," "B. Recycling of Balloon Catheter," "C. Medical Assistance," "D. Improvement in Product," "E. Individual Management," "F. Management by Supply Chain," and "G. Management of Reuse Product by Maintenance Service Provider" will mainly be described below in this order.

In the section "A. Acquisition of Data," a configuration of a balloon catheter is specified and data obtained by the balloon catheter will be described. In the section "B. Recycling of Balloon Catheter," recycling processing based on obtained data will be described.

Similarly, in each section of "C. Medical Assistance," "D. Improvement in Product," "E. Individual Management," "F. Management by Supply Chain," and "G. Management of Reuse Product by Maintenance Service Provider," an example where the obtained data is used will be described.

A. Acquisition of Data a1. Overview

FIG. 1 is a diagram for illustrating a schematic configuration of a balloon catheter.

Referring to FIG. 1, a balloon catheter 10 includes a hub 11, a strain relief 12, a catheter shaft 13, a balloon 14, and a guide wire port 15.

Guide wire port 15 is formed in catheter shaft 13. A guide wire 16 is inserted into balloon catheter 10 through guide wire port 15. Hub 11 includes a balloon inflation port 17.

In connection with balloon catheter 10, a side of hub 11 is also referred to as a "rear end side" and a side of balloon 14 is also referred to as a "tip end side" below.

Figure 2:
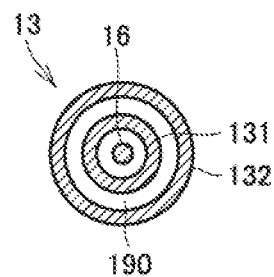
FIG. 2 is a cross-sectional view along II-II in FIG. 1.

FIG. 2 is a cross-sectional view along II-II in FIG. 1.

Referring to FIG. 2, catheter shaft 13 is constituted of an inner pipe 131 and an outer pipe 132. Inner pipe 131 functions as a path for insertion of guide wire 16.

A pipe path 190 which is a space between inner pipe 131 and outer pipe 132 functions as a flow path for fluid. Pipe path 190 communicates with the inside of hub 11. Pipe path 190 is typically filled with liquid (which is also referred to as a "solution" below) as fluid, which is a mixture of a contrast agent, physiological saline, and heparin. The solution is normally also referred to as a "sterile solution."

On the tip end side of catheter shaft 13, inner pipe 131 extends from a tip end of outer pipe 132 and passes through balloon 14 in an axial direction. The tip end side of balloon 14 is joined to inner pipe 13. The rear end side of balloon 14 is joined to outer pipe 132.

As a doctor (operator) uses an inflation device to perform an operation to increase a pressure of the solution (fluid pressure), balloon 14 is inflated.

Figure 3:
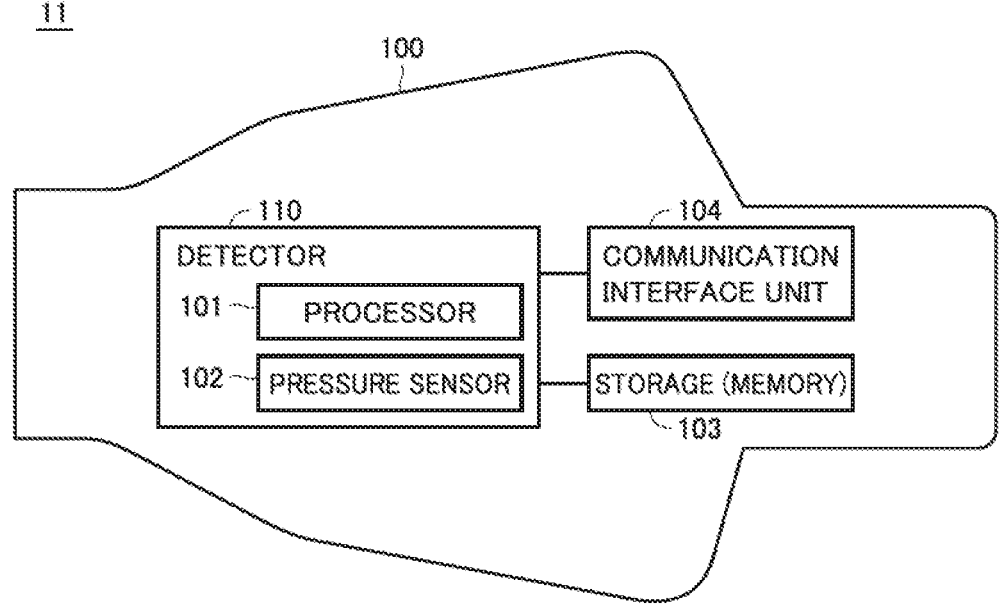
FIG. 3 is a diagram for illustrating a functional configuration of the balloon catheter.

FIG. 3 is a diagram for illustrating a functional configuration of balloon catheter 10.

Referring to FIG. 3, hub 11 of balloon catheter 10 includes a detector 110, a storage 103, and a communication interface unit 104.

Detector 110 is typically constituted of a processor 101, a pressure sensor 102, and a clock (not shown). Detector 110 is communicatively connected to storage 103 and communication interface unit 104. Since detector 110 includes processor 101, it functions as a control unit of balloon catheter 10.

Detector 110 detects a state value including at least a pressure generated in pipe path 190 of balloon catheter 10. In one aspect, detector 110 detects with pressure sensor 102, change over time in pressure (fluid pressure) applied by the inflation device to pipe path 190.

Specifically, pressure sensor 102 outputs an electrical signal (for example, a voltage) in accordance with a detected pressure. Processor 101 converts the electrical signal into a pressure. Processor 101 processes that pressure as the pressure generated in pipe path 190.

Figure 14:
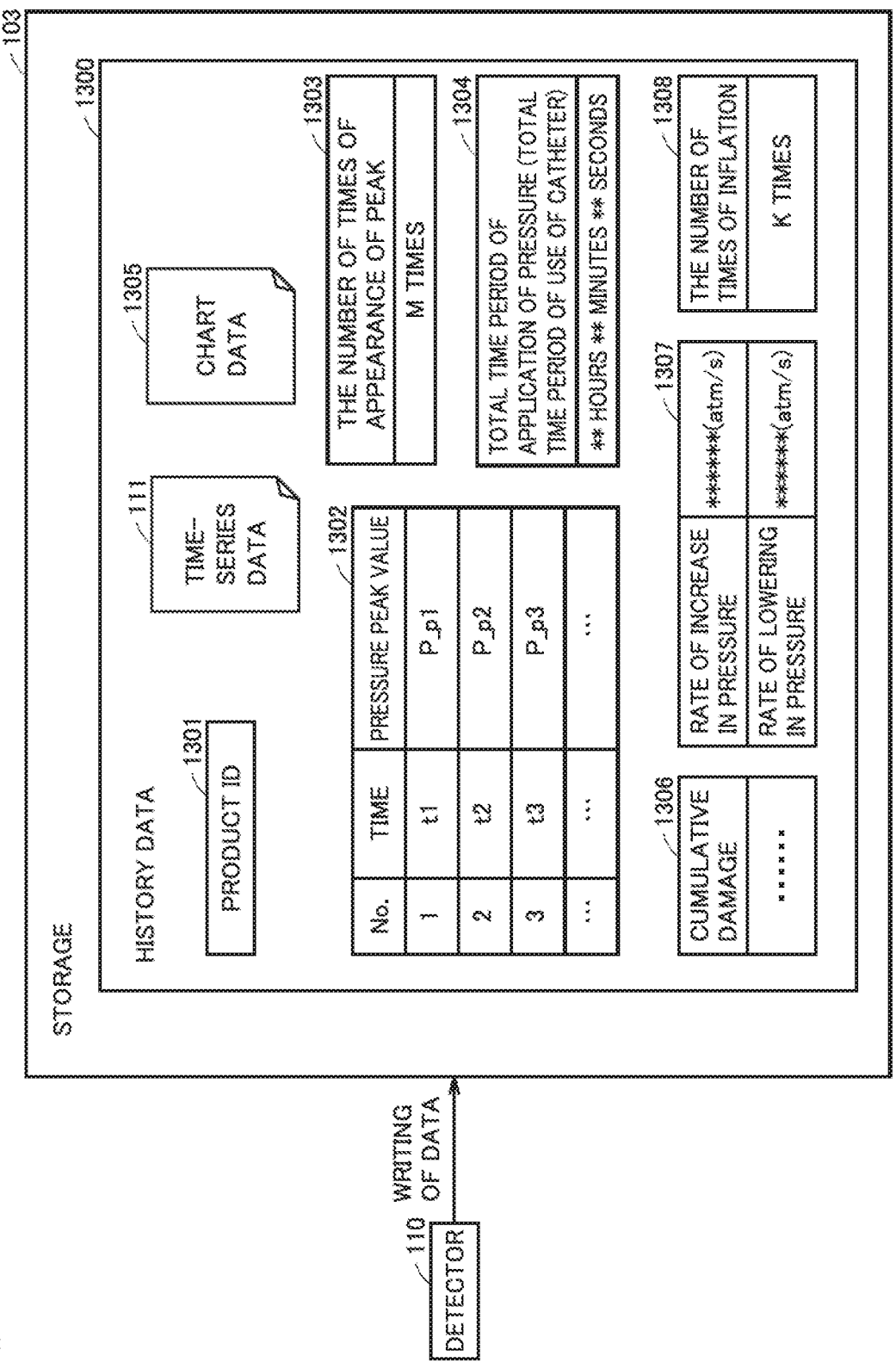
FIG. 14 is a diagram for illustrating a state value stored in a storage by a data processing unit.

The "state value," that is, a "result of detection," includes various values such as change over time in pressure applied to pipe path 190, a peak value of the pressure, and the number of times of appearance of the peak. These values are calculated by computation by processor 101. Specific examples of the "state value" will be described later (FIG. 14 or the like).

Storage 103 stores a result of detection by detector 110. Storage 103 is typically implemented by a non-volatile memory. Storage 103 may be implemented, for example, by a flash memory.

Communication interface unit 104 externally outputs a result of detection stored in storage 103. Communication interface unit 104 establishes wireless or wired communication with an external apparatus based on a predetermined communication protocol.

With such a configuration, balloon catheter 10 can store in storage 103, a state value including at least a pressure generated in pipe path 190. Furthermore, balloon catheter 10 can externally output a state value stored in storage 103 through communication interface unit 104.

Though detector 110 preferably includes a clock from a point of view of obtaining time-series data, the clock is not essential. In a configuration where detector 110 includes a clock, power is preferably constantly fed by a battery or the like to a circuit such as detector 110. Instead of the clock, a timer may be provided.

Though a configuration in which hub 11 detects a pressure in pipe path 190 is exemplified above, limitation thereto is not intended. Pressure sensor 102 may be provided in another portion such as catheter shaft 13 or strain relief 12. Similarly, processor 101, storage 103, and communication interface unit 104 may be provided in a portion other than hub 11.

Storage of a result of detection in storage 103 and external output of the result of detection through communication interface unit 104 are typically based on a command from processor 101. A program executed by the processor may be stored in storage 103 or in another portion such as detector 110.

Instead of or along with externally outputting the result of detection stored in storage 103, communication interface unit 104 may output a result of detection to an output apparatus provided in balloon catheter 10. For example, communication interface unit 104 may output a result of detection to a display (see FIG. 32) or a speaker (see FIG. 30).

Figure 4:
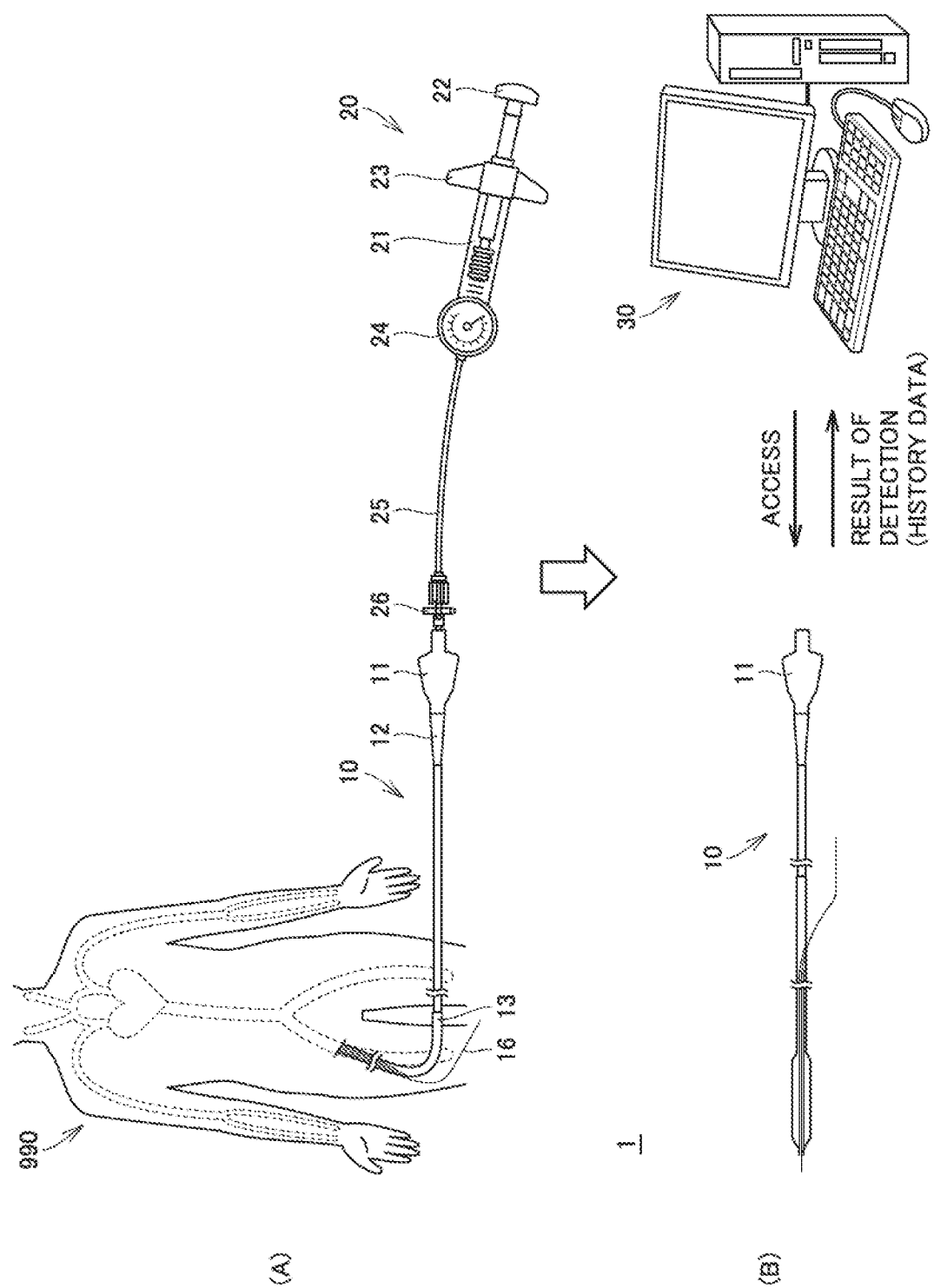
FIG. 4 is a diagram for illustrating exemplary usage of the balloon catheter.

FIG. 4 is a diagram for illustrating exemplary usage of balloon catheter 10.

Referring to FIG. 4, as shown in a state (A), while an inflation device 20 is connected to balloon catheter 10, a tip end of balloon catheter 10 is inserted into a body (specifically, into a blood vessel) of a patient 990. Before insertion of balloon catheter 10 into patient 990, zero-point calibration of pressure sensor 102 is preferably carried out as necessary.

Inflation device 20 typically includes a syringe 21, a piston 22, a locking lever 23, a gauge 24, a connection tube 25, and a T-shaped stopcock 26.

Inflation device 20 is connected to balloon catheter 10 with T-shaped stopcock 26 being interposed. As a doctor operates piston 22 while inflation device 20 is connected to balloon catheter 10, a solution in syringe 21 is delivered to balloon catheter 10 through connection tube 25. Balloon 14 is thus inflated within a blood vessel. Gauge 24 measures a pressure of the solution that flows from syringe 21 to connection tube 25.

With a surgery above, a state value including at least a pressure generated in pipe path 190 of balloon catheter 10 is stored in storage 103 (see FIG. 3) of balloon catheter 10. When the surgery for patient 990 ends, balloon catheter 10 is drawn from the inside to the outside of the human body.

As shown in a state (B), information processing system 1 includes balloon catheter 10 and a management apparatus 30. Management apparatus 30 is typically implemented by a server or a personal computer.

Balloon catheter 10 performs processing for transmitting a state value (a result of detection) stored in storage 103 to external management apparatus 30. Typically, as management apparatus 30 transmits a signal that requests for transmission of the result of detection to balloon catheter 10, balloon catheter 10 transmits the result of detection to management apparatus 30.

Prior to such transmission and reception of the result of detection, a maintenance service provider of the balloon catheter accepts used balloon catheter 10. Typically, a collection service provider that collects balloon catheters collects used balloon catheters 10 from a hospital and passes the collected used balloon catheters 10 to a maintenance service provider. Thereafter, typically, the maintenance service provider transmits and receives the result of detection. The collection service provider and the maintenance service provider may be the same.

In the present example, the term "accept" is used as a concept encompassing "collect". A used balloon catheter accepted by a maintenance service provider is also referred to as a "collected used balloon catheter" below for the sake of convenience. Furthermore, a result of detection (a state value) is also referred to as "history data."

Though details will be described later, a result of detection read from storage 103 by management apparatus 30 is used for determination as to whether or not to recycle a used balloon catheter.

a2. Details of Balloon Catheter

The balloon catheter includes a balloon catheter that physically spreads by pressing, a tissue (a blood vessel or the like) by inflating a balloon and a balloon catheter that provides a living body with repeated rhythms of inflation and deflation of a balloon. Balloon catheter 10 according to the present embodiment typically intends the former (a balloon catheter that physically spreads by pressing, a tissue by inflating a balloon), although the latter is not excluded.

The former balloon catheter is further categorized into a "balloon catheter simply including a balloon alone," a "balloon catheter in which a pharmaceutical drug is applied to a surface of a balloon," a "balloon catheter including small physical protrusions on a balloon," a "balloon catheter in which a stent for implantation is held on a balloon and the stent alone is expanded to indwell," and a "balloon catheter in which small pores (micropores) are provided in a wall of a balloon so that a pharmaceutical drug can be injected through the pores."

Though a rapid exchange type configuration in which guide wire 16 is inserted to a position intermediate (guide wire port 15) between the tip end side and the rear end side of catheter shaft 13 is described above by way of example of balloon catheter 10 as shown in FIG. 1, the type of the balloon catheter is not limited thereto.

For example, the balloon catheter may be such an over-the-wire type that a guide wire is inserted from the tip end side to the rear end side of a catheter shaft. The balloon catheter may be a perfusion balloon catheter including a perfusion lumen through which blood or the like is movable between the rear end side and the tip end side of a balloon for facilitated transfer of a pharmaceutical drug held on the balloon to an inner wall of a blood vessel by inflation of the balloon for a long period of time.

"Supply of power," "sensing", "stored data," and "reading of data" in connection with balloon catheter 10 will be described below in this order.

(1) Supply of Power

A manner of supply of power to detector 110 (processor 101 and pressure sensor 102), storage 103, and communication interface unit 104 will be described below.

Figure 5:
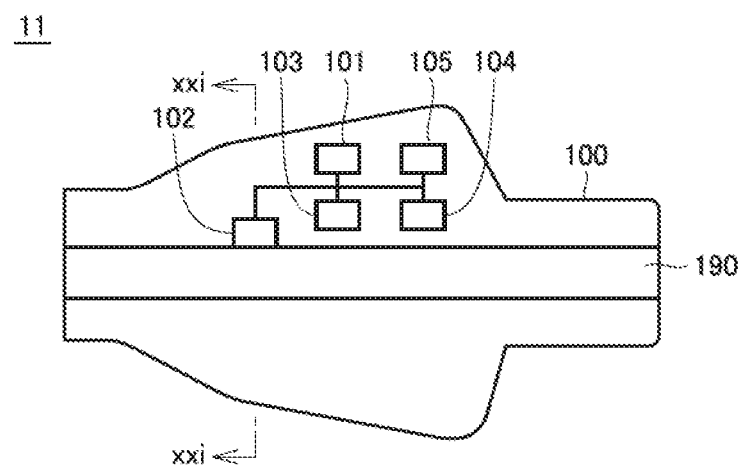
FIG. 5 is a diagram for illustrating supply of power.

FIG. 5 is a diagram for illustrating supply of power.

Referring to FIG. 5, hub 11 includes in a housing 100 of hub 11, processor 101, pressure sensor 102, storage 103, communication interface unit 104, and a battery 105.

In such a configuration, processor 101, pressure sensor 102, storage 103, and communication interface unit 104 receive supply of power from battery 105.

Battery 105 may be chargeable. Hub 11 may allow replacement of battery 105.

Figure 6:
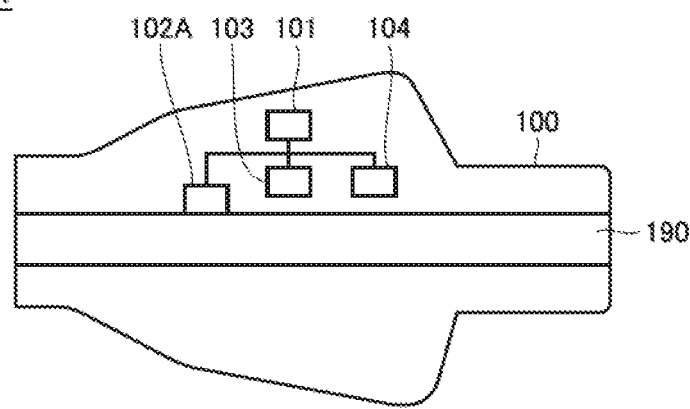
FIG. 6 is a diagram for illustrating a first modification of supply of power.

FIG. 6 is a diagram for illustrating a first modification of supply of power.

Referring to FIG. 6, balloon catheter 10 includes a hub 11A instead of hub 11. Hub 11A includes processor 101, a piezoelectric element 102A as the pressure sensor, storage 103, and communication interface unit 104.

With such a configuration, when a pressure is applied to pipe path 190 as a result of operation of inflation device 20, piezoelectric element 102A is slightly deformed (specifically, compressed). Piezoelectric element 102A thus generates electricity. Electricity generated by piezoelectric element 102A is supplied to processor 101, storage 103, and communication interface unit 104.

In such a configuration, a pressure sensor and a power supply can be implemented by a single element.

In reading a result of detection (a state value) stored in storage 103 in the configuration including piezoelectric element 102A, a pressure should be applied to piezoelectric element 102A or power should externally be fed to processor 101.

Figure 7:
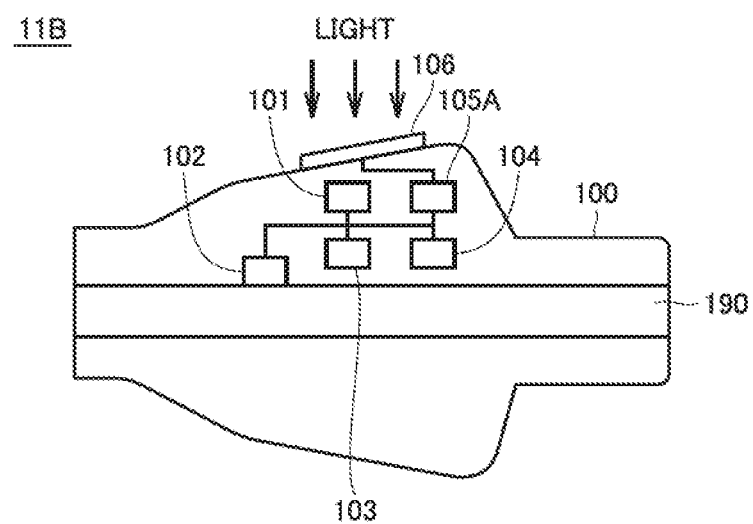
FIG. 7 is a diagram for illustrating a second modification of supply of power.

FIG. 7 is a diagram for illustrating a second modification of supply of power.

Referring to FIG. 7, balloon catheter 10 includes a hub 11B instead of hub 11. Hub 11B includes processor 101, pressure sensor 102, storage 103, communication interface unit 104, a storage battery 105A, and a solar panel 106.

Electricity generated by solar panel 106 is stored in storage battery 105A.

Processor 101, pressure sensor 102, storage 103, and communication interface unit 104 receive supply of power from storage battery 105A.

In such a configuration, electric power can be generated by external light (light in an operating room or the like). Therefore, electric power can continuously be supplied to processor 101 and the like.

Figure 8:
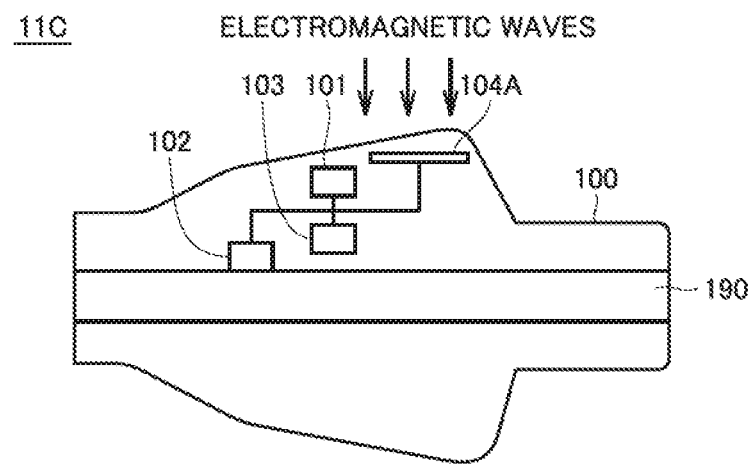
FIG. 8 is a diagram for illustrating a third modification of supply of power.

FIG. 8 is a diagram for illustrating a third modification of supply of power.

Referring to FIG. 8, balloon catheter 10 includes a hub 11C instead of hub 11. Hub 11C includes processor 101, pressure sensor 102, storage 103, and an antenna 104A for contactless communication. Hub 11C is in a form of pressure sensor 102 and a radio frequency identifier (RFID) as being combined.

Antenna 104A can allow a current to flow through a circuit including processor 101, by receiving radio waves from a not-shown data reader (for example, a reader-writer). Hub 11C outputs a result of detection stored in storage 103 to an external apparatus through antenna 104A.

By including antenna 104A, hub 11C can thus perform a function of a power supply and a function of communication interface unit 104.

Figure 9:
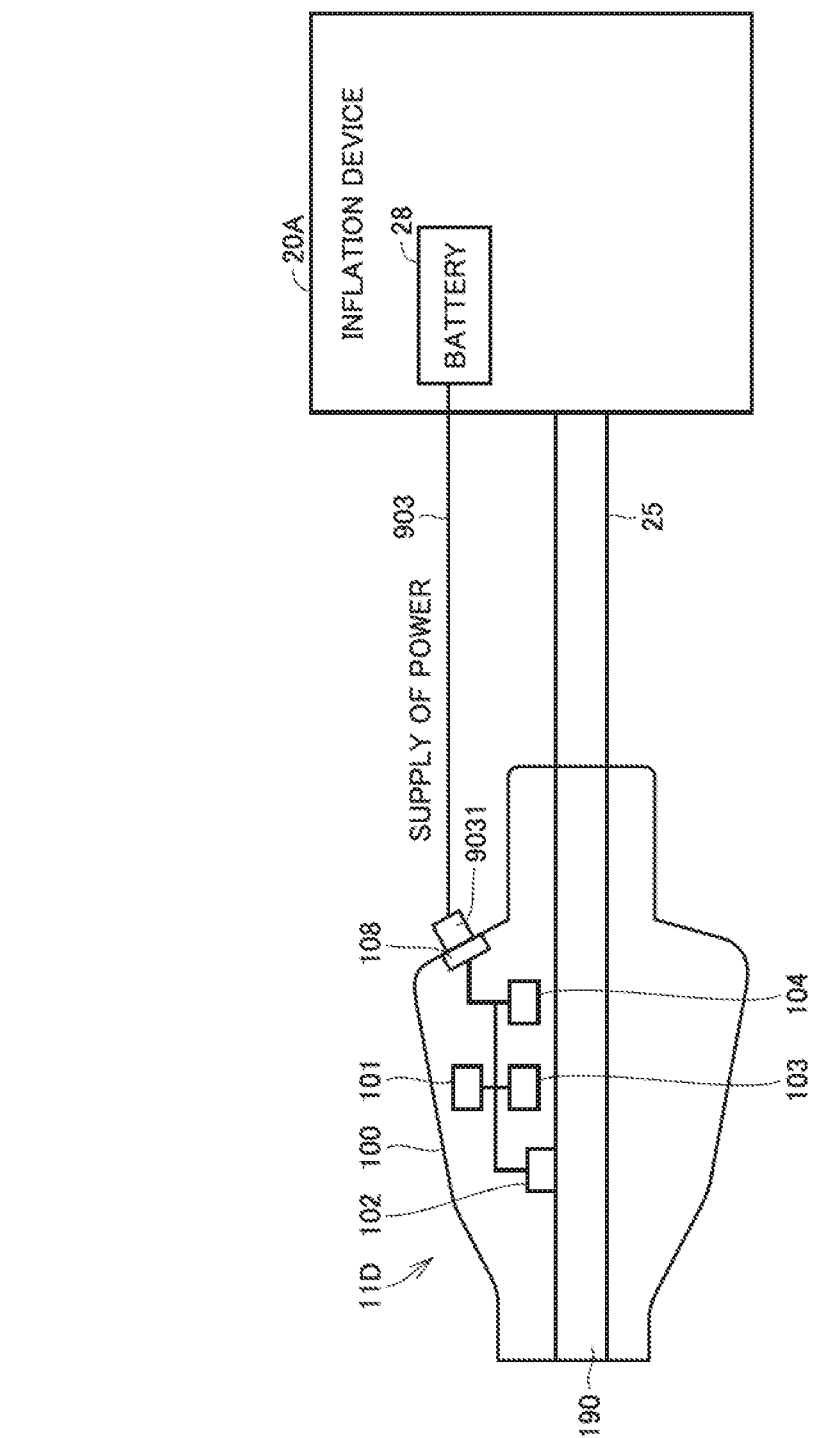
FIG. 9 is a diagram for illustrating a fourth modification of supply of power.

FIG. 9 is a diagram for illustrating a fourth modification of supply of power.

Referring to FIG. 9, balloon catheter 10 includes a hub 11D instead of hub 11. Hub 11D includes processor 101, pressure sensor 102, storage 103, communication interface unit 104, and a port 108. In the present example, port 108 functions as a power feed port and also functions as a communication port. Without being limited as such, hub 11D may separately include a power feed port and a communication port.

In this configuration, an inflation device 20A containing a battery 28 is employed as the inflation device instead of inflation device 20. Inflation device 20A is different from inflation device 20 in including battery 28 and otherwise the same as inflation device 20.

Inflation device 20A is connected to hub 11D through a cable 903. A connector 9031 for connection to port 108 is provided at a tip end (opposite to battery 28) of cable 903.

As connector 9031 is connected to port 108, power feed from battery 28 to processor 101, pressure sensor 102, storage 103, and communication interface unit 104 is started. With such a configuration as feeding power from inflation device 20 to balloon catheter 10, a side of balloon catheter 10 does not require a battery or a mechanism that generates electric power.

In the present example, cable 903 functions as a power supply cable and also functions as a communication cable. Inflation device 20A may include a port for connecting cable 903 and battery 28 to each other. In this case, cable 903 requires a connector for connection to inflation device 20A, separately from connector 9031.

Figure 10:
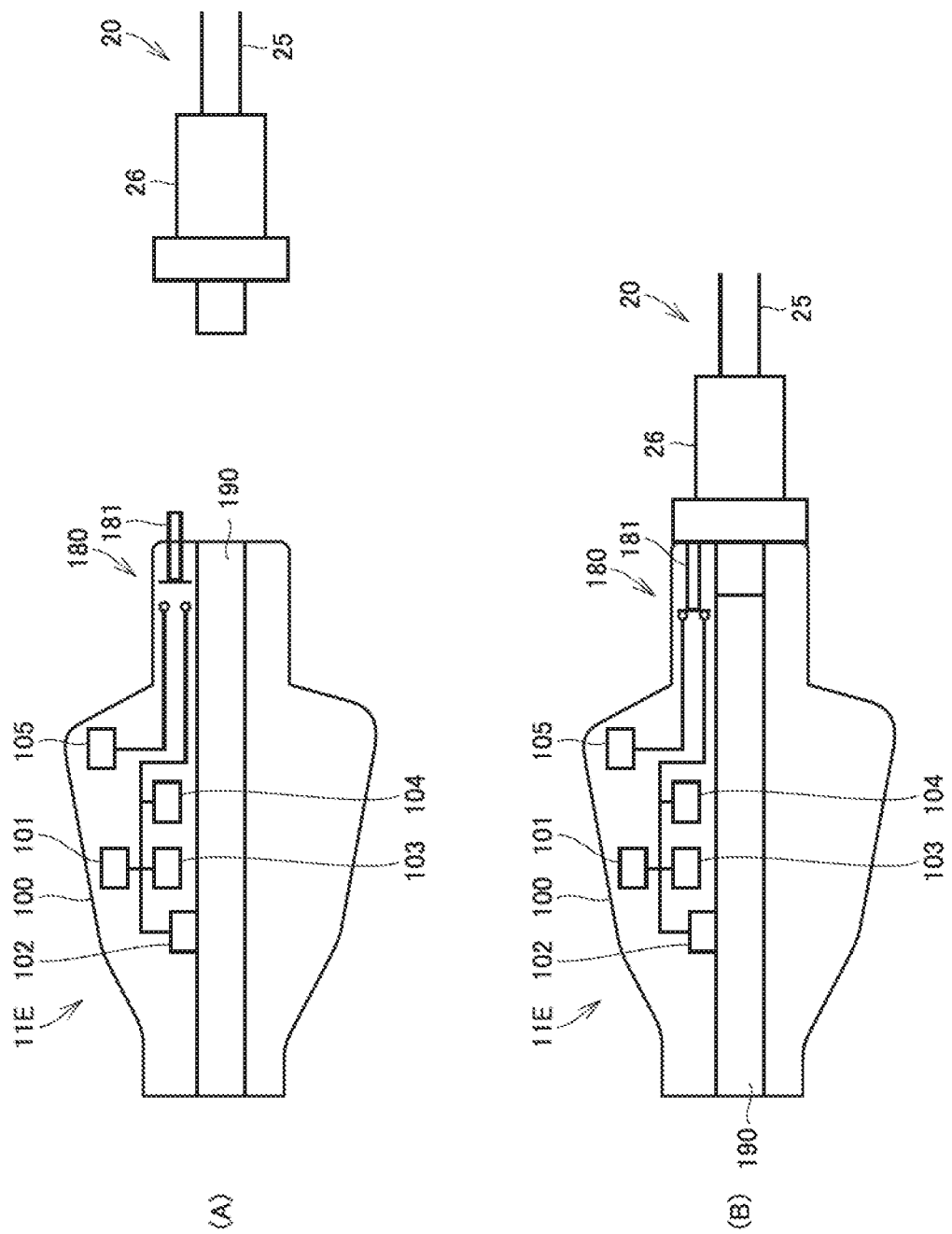
FIG. 10 is a diagram for illustrating a fifth modification of supply of power.

FIG. 10 is a diagram for illustrating a fifth modification of supply of power.

Referring to FIG. 10, balloon catheter 10 includes a hub 11E instead of hub 11. Hub 11E includes processor 101, pressure sensor 102, storage 103, communication interface unit 104, battery 105, and a switch 180.

Switch 180 is an a-contact switch by way of example. Switch 180 includes a movable member 181 for turning on the switch. Movable member 181 is formed of a non-conductive material such as a resin.

While T-shaped stopcock 26 of inflation device 20 is not connected to hub 11E, movable member 181 is set at a default position and switch 180 is off. Therefore, battery 105 and processor 101 and the like are not conducting to each other and power is not fed from battery 105 to processor 101 and the like.

When T-shaped stopcock 26 of inflation device 20 is connected to hub 11E, movable member 181 moves into hub 11E. Switch 180 thus makes transition from off to on. Therefore, battery 105 and processor 101 and the like conduct to each other and power feed from battery 105 to processor 101 and the like is started.

The configuration of the switch is not limited as described above. The configuration of the switch is not particularly limited so long as power is fed to processor 101 and the like when inflation device 20 is connected to balloon catheter 10.

Though a configuration in which detector 110 (processor 101, pressure sensor 102, and piezoelectric element 102A), storage 103, communication interface unit 104, antenna 104A, battery 105, storage battery 105A, and port 108 are arranged in housing 100 in hubs 11, 11A, 11B, 11C, 11D, and 11E is described by way of example, limitation thereto is not intended. Some or all of members may be arranged outside housing 100 of the hub.

(2) Sensing

Figure 11:
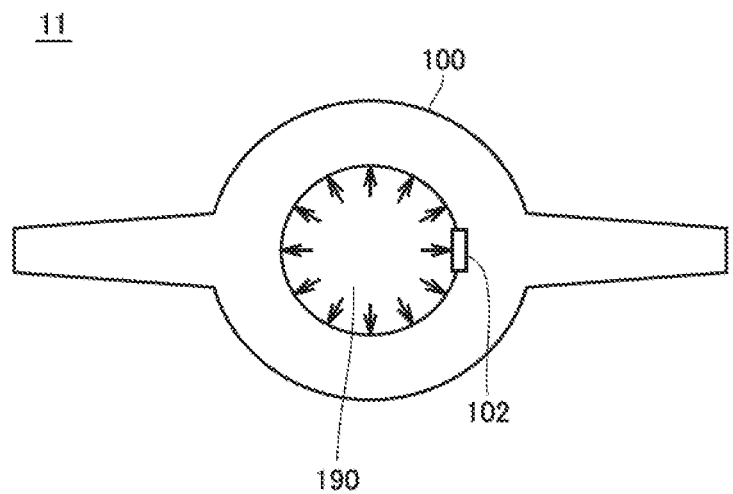
FIG. 11 is a cross-sectional view along the line xxi-xxi in FIG. 5.

FIG. 11 is a cross-sectional view along the line xxi-xxi in FIG. 5.

Referring to FIG. 11, pressure sensor 102 is typically set on a wall surface in pipe path 190 of housing 100 of hub 11 such that a detection surface where a pressure is detected is exposed at pipe path 190.

Pressure sensor 102 thus arranged within pipe path 190 can detect a pressure generated in pipe path 190.

Arrangement and a type of pressure sensor 102 are not limited so long as the pressure sensor can detect a pressure generated in pipe path 190.

A sensor that measures a flow rate of a solution that flows through pipe path 190 may be provided instead of pressure sensor 102 and processor 101 may estimate a pressure generated in pipe path 190 based on a result of measurement by the sensor.

(3) Stored Data

FIG. 12 is a diagram for illustrating overview of exemplary data detected by detector 110 of balloon catheter 10.

FIG. 12 (A) shows exemplary data detected by balloon catheter 10 including each of hub 11 and 11B to 11E (see FIGS. 5 and 7 to 10). FIG. 12 (B) shows exemplary data detected by balloon catheter 10 including hub 11A (see FIG. 6) including piezoelectric element 102A.

Referring to FIG. 12 (A), when a doctor performs surgery to inject a solution into balloon catheter 10 by using inflation device 20 for inflating balloon 14, a numeric value (for example, a voltage value) indicating a pressure output from pressure sensor 102 increases. When the doctor performs surgery to deflate balloon 14, a numeric value indicating a pressure output from pressure sensor 102 is lowered. In the figure, pressures Pa and Pb represent peak values of the pressure.

Referring to FIG. 12 (B), when a doctor performs surgery to inject a solution into balloon catheter 10 by using inflation device 20 for inflating balloon 14 and a pressure in pipe path 190 (a pressure applied to piezoelectric element 102A) exceeds a threshold value Th1, electric power is supplied from piezoelectric element 102A to processor 101, storage 103, and the like. Detector 110 can detect a state value including at least a pressure generated in pipe path 190 during a period for which electric power is supplied. In addition, detector 110 can have storage 103 store the detected state value (result of detection) during this period.

Therefore, when hub 11A including piezoelectric element 102A is employed, the state value is not detected nor stored in storage 103 while a pressure applied to piezoelectric element 102A does not exceed threshold value Th1.

Though FIG. 12 (A) and (B) shows change in pressure with a solid line for the sake of convenience of description, a calculated pressure has a temporally discrete value because processor 101 performs periodic computation processing based on a clock.

Figure 13:
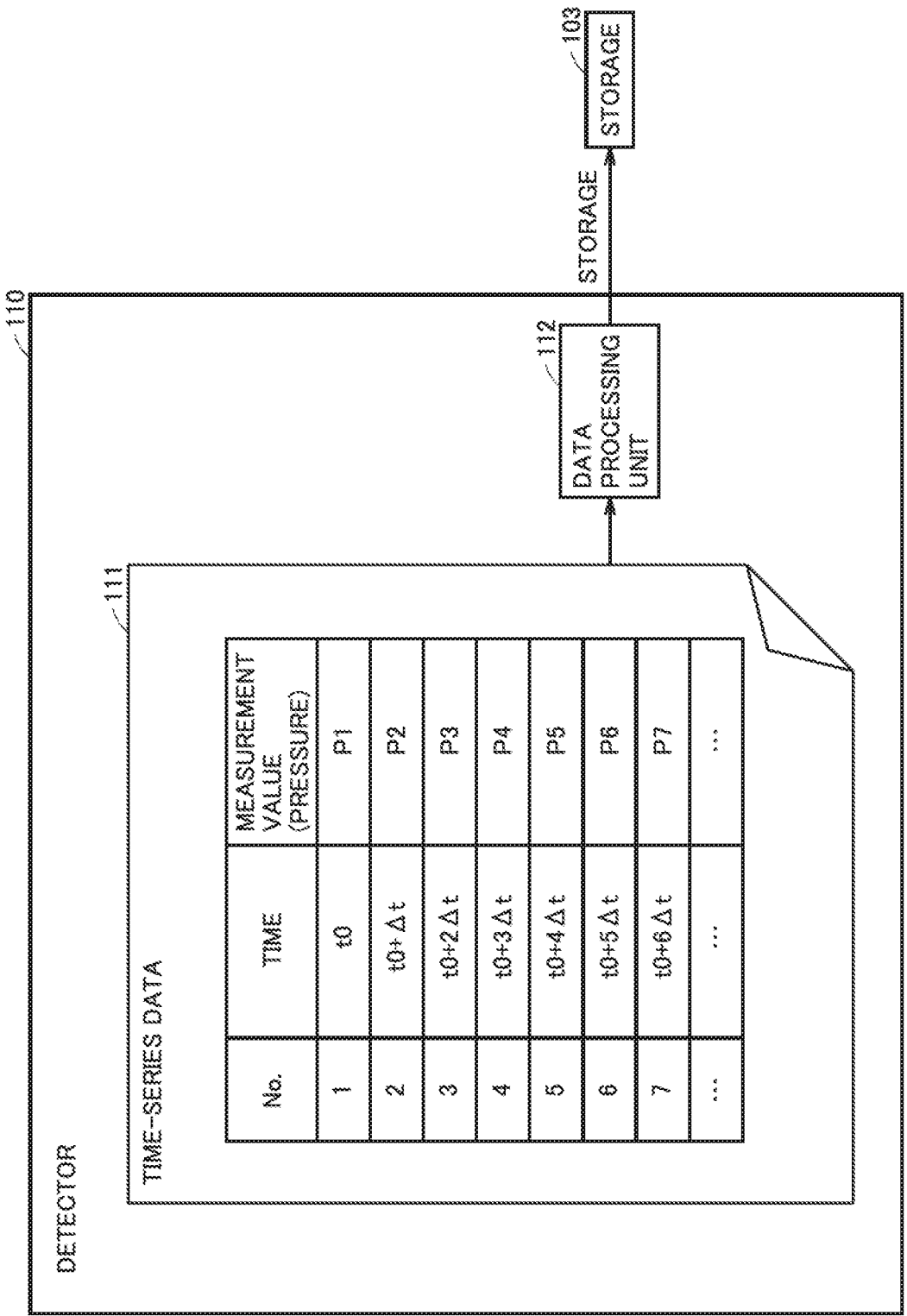
FIG. 13 is a diagram for illustrating a detector in the balloon catheter.

FIG. 13 is a diagram for illustrating detector 110 in balloon catheter 10.

Referring to FIG. 13, detector 110 generates time-series data 111 representing pressures in pipe path 190 as a result of processing by pressure sensor 102 and processor 101. Processor 101 associates time of measurement with each measurement value (pressure) based on a clock.

A data processing unit 112 obtains the state value (result of detection) described above by performing prescribed data processing on time-series data. Data processing unit 112 has storage 103 store the calculated state value. Data processing unit 112 is a functional block implemented by execution of a program by processor 101.

FIG. 14 is a diagram for illustrating a state value stored in storage 103 by means of data processing unit 112.

Referring to FIG. 14, storage 103 stores history data 1300 including a state value. History data 1300 includes a product ID 1301, time-series data 111 (see FIG. 13), pressure peak value data 1302, data 1303 that represents the number of times of appearance of a peak of the pressure, data 1304 representing a total time period of application of a pressure, chart data 1305 (FIG. 12 (A) or the like), data 1306 on cumulative damage in balloon catheter 10, data 1307 representing a rate of increase and lowering in pressure, and data 1308 representing the number of times of inflation of balloon 14.

Of history data 1300, data (111 and 1302 to 1308) except for product ID 1301 falls under a "state value." Balloon catheter 10 may manage product ID 1301 separately from other types of data, without including the product ID in history data 1300.

An expiration date of use of balloon catheter 10 is preferably stored in advance in storage 103 in association with the product ID. In particular, the expiration date of use is preferably managed as being included in history data 1300. A date of manufacturing together with the expiration date of use may be managed as being included in history data.

Chart data 1305 is data representing discrete pressure values described above in a continuous graph as shown in FIG. 12 (data representing relation between a pressure and time with a line segment).

Cumulative damage is obtained by integration of chart data 1305. Cumulative damage is expressed as a numeric value obtained by integrating an applied pressure with respect to a time period of application.

When detector 110 senses increase and lowering in pressure once, it increases by one a value of the number of times of inflation in data 1308. Specifically, when detector 110 detects increase and lowering in pressure by a predetermined value or more, it increments the number of times of inflation. The detector does so in order to prevent increment of the number of times of inflation in spite of inflation of balloon 14 only to a small extent.

a3. Reading of Data

A hardware configuration of management apparatus 30 will be described and then processing for reading of history data 1300 by management apparatus 30 from storage 103 of balloon catheter 10 will be described.

(1) Hardware Configuration of Management Apparatus 30

Figure 15:
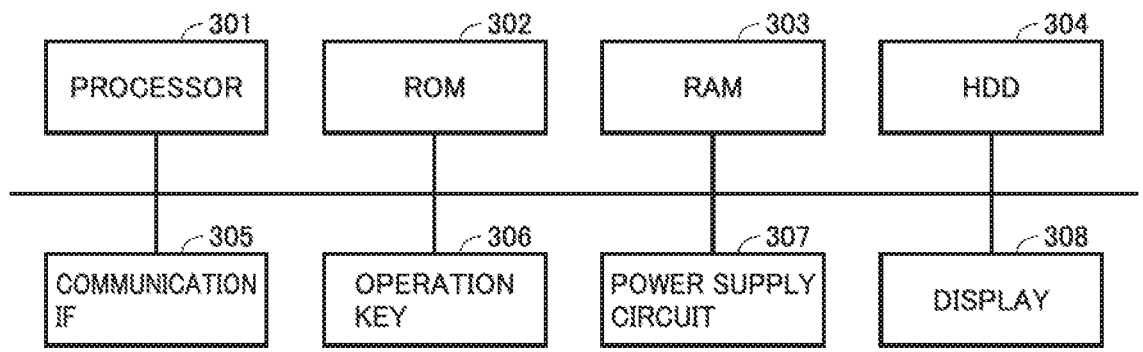
FIG. 15 is a diagram representing a typical example of a hardware configuration of a management apparatus.

FIG. 15 is a diagram representing a typical example of a hardware configuration of management apparatus 30.

Referring to FIG. 15, management apparatus 30 includes, as its main components, a processor 301 that executes a program, a read only memory (ROM) 302 that stores data in a non-volatile manner, a random access memory (RAM) 303 that stores in a volatile manner, data generated as a result of execution of a program by processor 301 or data input through an input apparatus, a hard disk drive (HDD) 304 that stores data in a non-volatile manner, a communication interface (IF) 305, an operation key 306, a power supply circuit 307, and a display 308. The components are connected to one another through a data bus. Communication IF 305 is an interface for communication with another device.

Processing in management apparatus 30 is performed by hardware and software executed by processor 301. Such software may be stored in advance in HDD 304. Software may be distributed as a program product as being stored in another storage medium. Alternatively, software may be provided as a program product that can be downloaded by an information provider connected to what is called the Internet. Such software is read from the storage medium by a reader or downloaded through communication IF 305 and thereafter once stored in HDD 304. Software is read from HDD 304 by processor 301 and stored in RAM 303 in a format of an executable program. Processor 301 executes the program.

Each component included in management apparatus 30 shown in the figure is a common component. Therefore, the essential part of the present invention can be said as residing in software stored in RAM 303, HDD 304, or a storage medium or software that can be downloaded through a network NW. Since an operation of hardware of management apparatus 30 has been well known, detailed description will not be repeated.

Each of servers 40, 60, 70, and 80 and a terminal apparatus 907 which will be described later also includes a hardware configuration as in management apparatus 30.

(2) Functional Configuration of Management Apparatus 30

Figure 16:
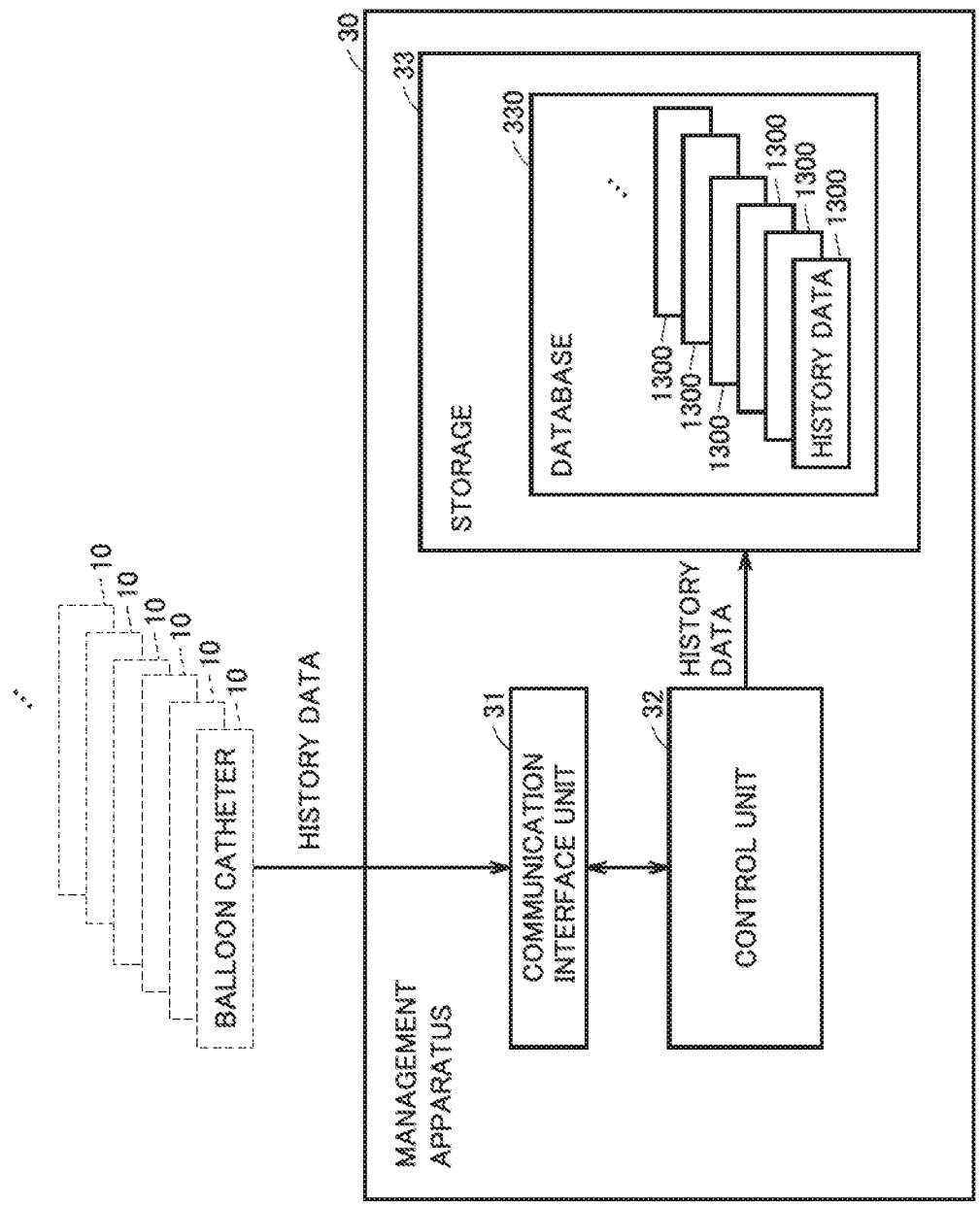
FIG. 16 is a functional block diagram representing a functional configuration of the management apparatus.

FIG. 16 is a functional block diagram representing a functional configuration of management apparatus 30.

Referring to FIG. 16, management apparatus 30 includes a communication interface unit 31, a control unit 32, and a storage 33. Storage 33 includes a database 330.

Control unit 32 is typically implemented by execution by processor 301 of a program stored in HDD 304 or the like and developed on the RAM. The communication interface unit corresponds to communication IF unit 305. Storage 33 typically corresponds to HDD 304.

Management apparatus 30 obtains history data 1300 (see FIG. 14) from each of a plurality of balloon catheters 10. Specifically, management apparatus 30 reads history data 1300 stored in each collected used balloon catheter 10 for each balloon catheter 10 (see the state (B) in FIG. 4).

Read history data 1300 is sent to control unit 32 through communication interface unit 31. Control unit 32 has database 330 of storage 33 store history data 1300.

In database 330, typically, history data 1300 is managed for each balloon catheter 10. Management for each balloon catheter is based on a product ID included in history data 1300.

Management apparatus 30 can thus manage history data for each used balloon catheter 10.

(3) Manner of Data Reading

As described above, communication interface unit 104 establishes wireless or wired communication with an external apparatus (management apparatus 30 in the present example) based on a predetermined communication protocol. Balloon catheter 10 can thus transmit history data 1300 stored in storage 103 to management apparatus 30.

A manner of data reading in an example in which balloon catheter 10 includes hub 11C (see FIG. 8) and an example in which balloon catheter 10 includes hub 11D (see FIG. 9) will be described below. Furthermore, a manner of data reading in an example in which balloon catheter 10 includes a hub 11F (see FIG. 19) including a configuration not described above will be described.

Figure 17:
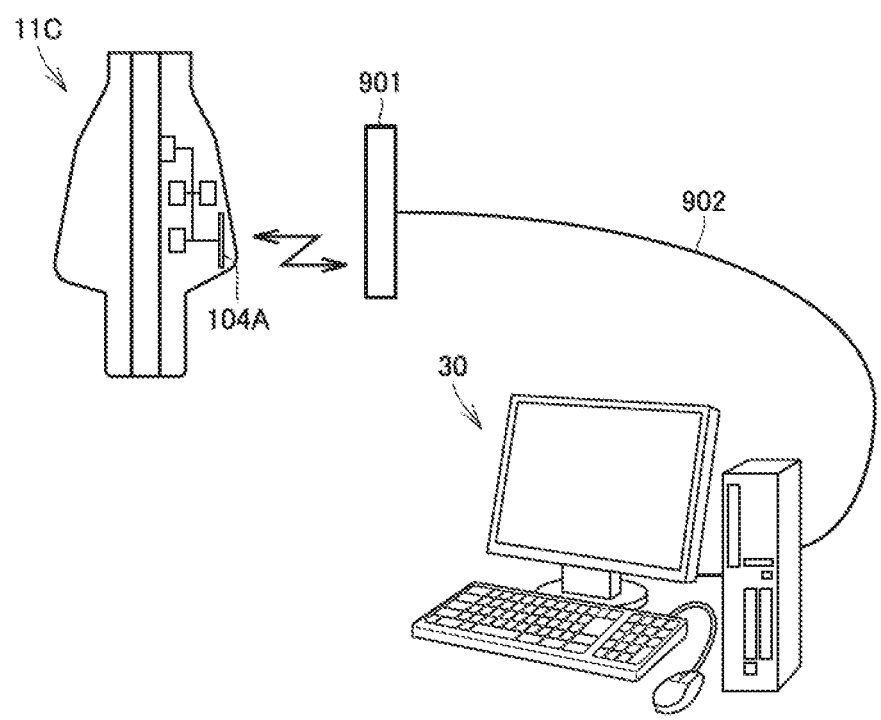
FIG. 17 is a diagram for illustrating processing for reading history data from a storage of a hub.

FIG. 17 is a diagram for illustrating processing for reading history data 1300 from storage 103 of hub 11C.

Referring to FIG. 17, a data reader 901 is connected to management apparatus 30 through a cable 902. As a user of management apparatus 30 sets antenna 104A as being opposed to data reader 901, history data 1300 stored in storage 103 of hub 11C is read by data reader 901. Thereafter, history data 1300 is transmitted to management apparatus 30 by data reader 901.

Figure 18:
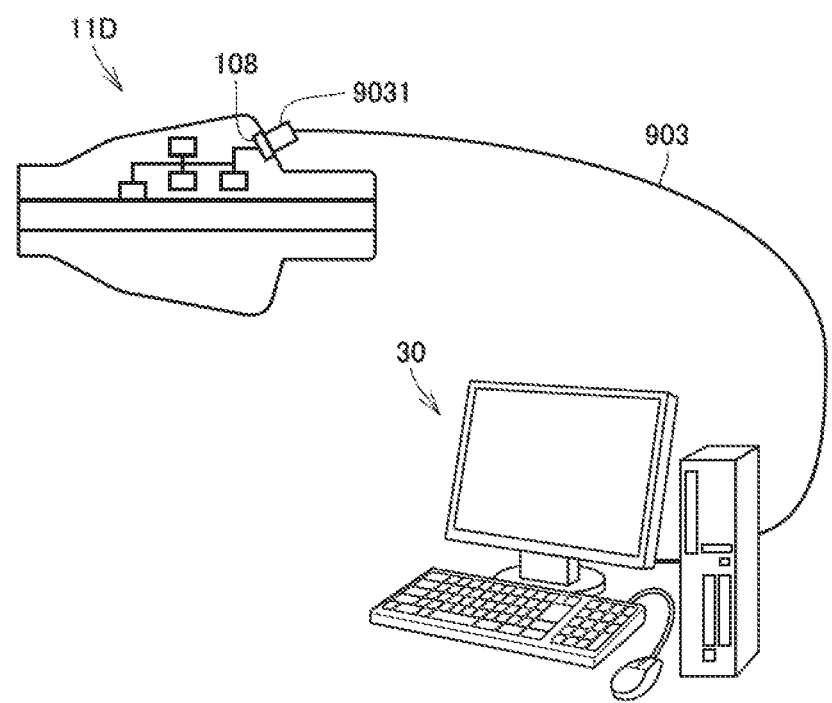
FIG. 18 is a diagram for illustrating processing for reading history data from a storage of a hub.

FIG. 18 is a diagram for illustrating processing for reading history data 1300 from storage 103 of hub 11D.

Referring to FIG. 18, cable 903 used for power feed (see FIG. 9) is connected to management apparatus 30 by way of example. Cable 903 is connected to port 108 through connector 9031.

As a user of management apparatus 30 sets antenna 104A as being opposed to data reader 901, history data 1300 stored in storage 103 of hub 11C is read by data reader 901. Thereafter, history data 1300 is transmitted to management apparatus 30 by data reader 901.

Figure 19:
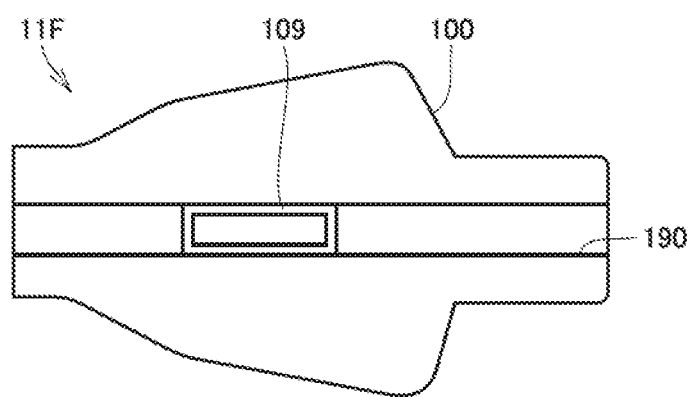
FIG. 19 is a diagram for illustrating a hub without requiring supply of power.

FIG. 19 is a diagram for illustrating hub 11F without requiring supply of power.

Referring to FIG. 19, hub 11F includes a device 109. Device 109 is provided in pipe path 190 and has its color varied depending on magnitude of a pressure in pipe path 190. Device 109 may be varied only in density of color depending on magnitude of a pressure in pipe path 190.

Figure 20:
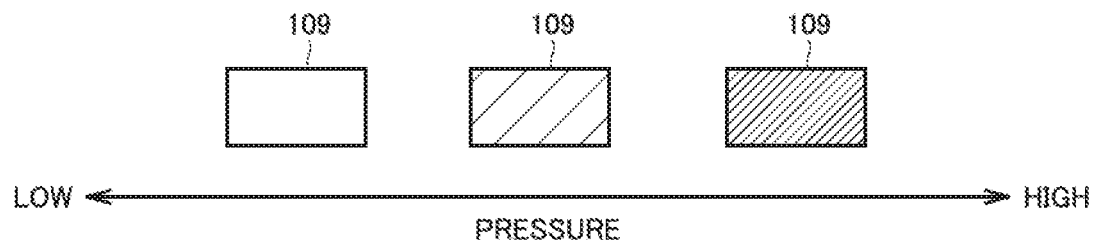
FIG. 20 is a diagram for illustrating variation in color of a device.

FIG. 20 is a diagram for illustrating variation in color of device 109. As shown in FIG. 20, as a pressure in pipe path 190 is higher, the color of the device (a hue or a density) is denser. Device 109 maintains the varied color even though the pressure is thereafter lowered.

Device 109 performs a function as a detector based on such variation in color. Device 109 performs a function as a storage by maintaining the varied color.

In this case, unlike other hubs 11, hub 11F (specifically, device 109) detects only a pressure in pipe path 190 as a "state value" described above.

Figure 21:
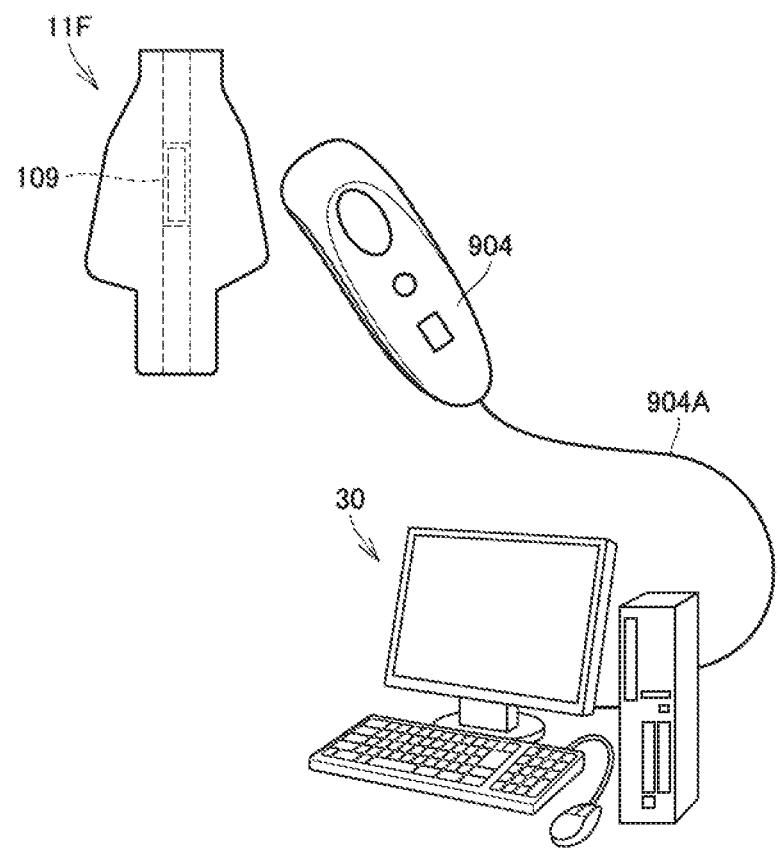
FIG. 21 is a diagram for illustrating processing for reading a state value (a result of detection) from the hub.

FIG. 21 is a diagram for illustrating processing for reading a state value (a result of detection) from hub 11F.

Referring to FIG. 21, a data reader 904 is connected to management apparatus 30 through a cable 904A. Data reader 904 includes an optical reader. Data reader 904 is typically implemented by a portable scanner.

As the user of management apparatus 30 sets a data reading section (not shown) as being opposed to device 109, information on a color of hub 11F is read by data reader 904. Thereafter, the read information on the color is transmitted to management apparatus 30 by data reader 904.

Management apparatus 30 further includes a data table representing relation between a color and a pressure. Management apparatus 30 specifies a pressure value read by data reader 904 and brought in correspondence with information on the color, by referring to the data table. Management apparatus 30 has storage 33 (see FIG. 16) store the specified pressure as the pressure in pipe path 190.

Device 109 thus performs not only a function as the detector and the storage but also a function as an interface unit.

(4) Control Structure

Figure 22:
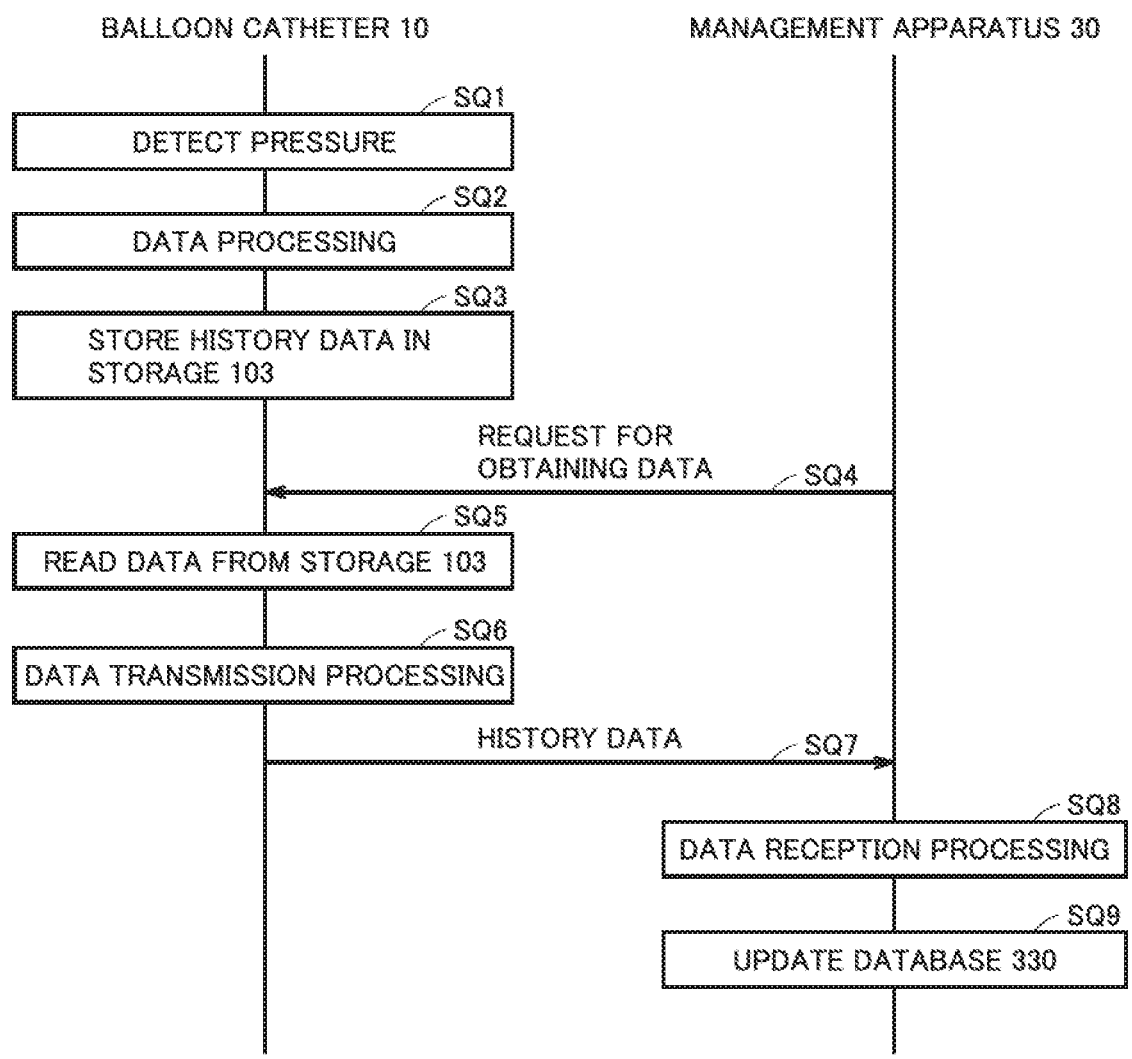
FIG. 22 is a sequence diagram for illustrating a flow of processing in an information processing system including a balloon catheter and a management apparatus.

FIG. 22 is a sequence diagram for illustrating a flow of processing in information processing system 1 including balloon catheter 10 and management apparatus 30. A configuration in which balloon catheter 10 includes hub 11 (see FIG. 5) will be described by way of example for the sake of convenience of description.

Referring to FIG. 22, in sequence SQ1, balloon catheter 10 detects, with detector 110, a pressure in pipe path 190 of balloon catheter 10. Typically, pressure sensor 102 outputs an electrical signal to processor 101.

In sequence SQ2, detector 110 subjects the electrical signal to data processing including various types of computation. Specifically, processor 101 generates time-series data 111 (see FIG. 13) on the pressure based on the electrical signal. Furthermore, processor 101 (specifically, data processing unit 112 in FIG. 13) generates history data 1300 except for the product ID.

In sequence SQ3, detector 110 (specifically, processor 101) has storage 103 store history data 1300 (see FIG. 14).

When balloon catheter 10 receives a data acquisition request signal that requests for transmission of history data 1300 from management apparatus 30 in sequence SQ4, detector 110 reads history data 1300 from storage 103 in sequence SQ5. In sequences SQ6 and SQ7, communication interface unit 104 transmits history data 1300 to management apparatus 30 from which the request for obtaining data was issued.

In sequence SQ8, management apparatus 30 receives history data 1300 from balloon catheter 10. In sequence SQ9, management apparatus 30 updates database 330 (see FIG. 16) with received history data 1300.

Though a configuration in which balloon catheter 10 includes hub 11 is described above by way of example, similar processing is performed also in an example where balloon catheter 10 includes hub 11A, 11B, 11C, 11D, or 11E. When balloon catheter 10 includes hub 11C, storage 30 issues a request (makes an access) for obtaining data to balloon catheter 10 through data reader 901 (see FIG. 17) and receives history data 1300 from balloon catheter 10 through data reader 901 (see FIG. 17).

B. Recycling of Balloon Catheter

Recycling of collected used balloon catheter 10 will now be described. Overview of recycling of balloon catheter 10 will initially be described. Then, determination as to reusability of a balloon catheter will specifically be described. Thereafter, a method of recycling a balloon catheter will be described and finally confirmatory inspection before shipment of a product will be described.

b1. Overview

Figure 23:
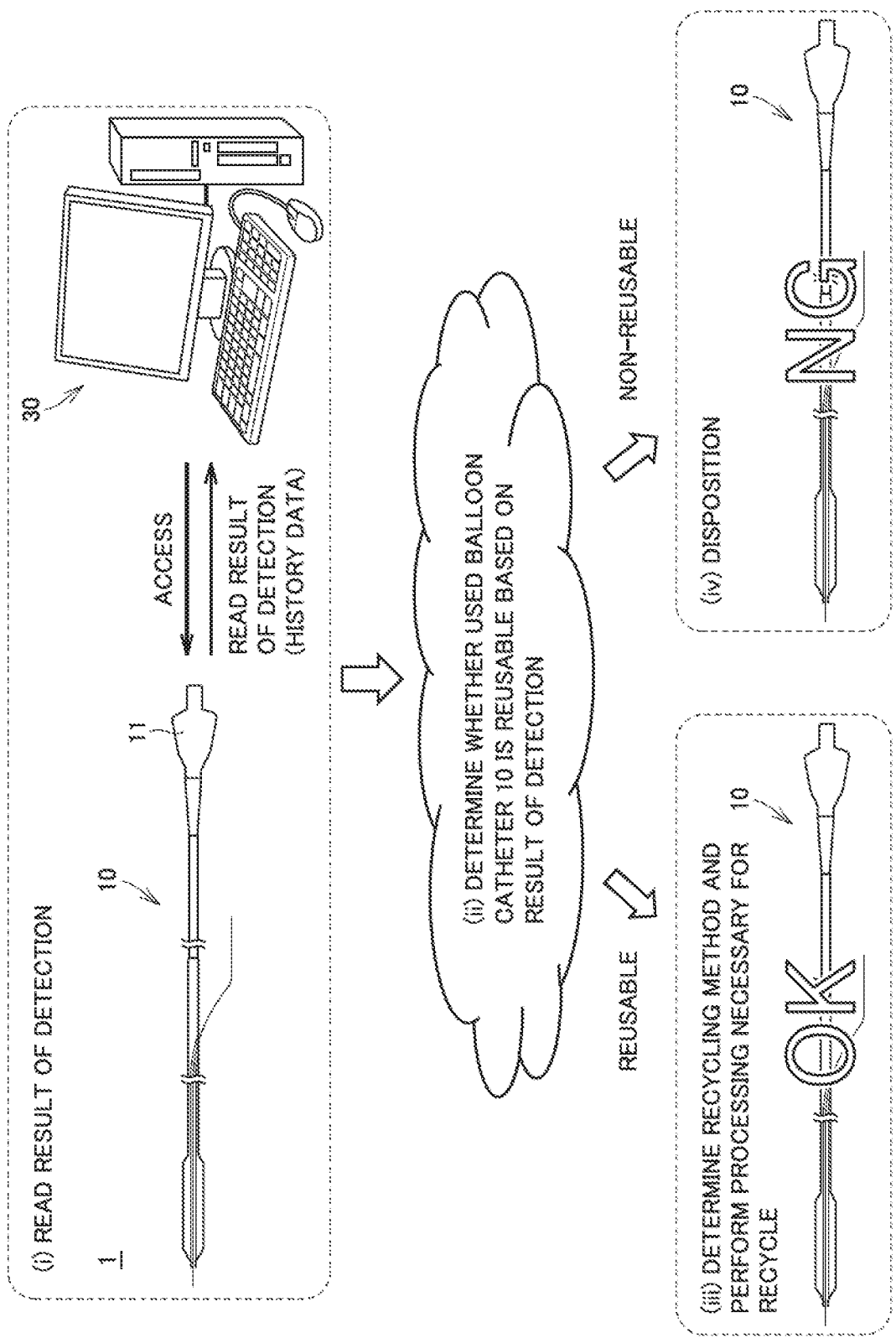
FIG. 23 is a diagram for illustrating a flow of recycling processing.

FIG. 23 is a diagram for illustrating a flow of recycling processing.

Referring to FIG. 23, as shown in a state (i), management apparatus 30 reads a result of detection (history data) stored in storage 103 of collected used balloon catheter 10. Then, as shown in a state (ii), the management apparatus determines whether or not collected used balloon catheter 10 is reusable based on the read result of detection.

When balloon catheter 10 is determined as being reusable, as shown in a state (iii), the management apparatus determines a method of recycling the collected used balloon catheter based on the read result of detection and performs processing necessary for recycling on balloon catheter 10. When balloon catheter 10 is determined as non-reusable, as shown in a state (iv), balloon catheter 10 is disposed of Though a flow from determination as to reusability of collected used balloon catheter 10 to determination as to a method of recycling balloon catheter 10 is described above by way of example, limitation thereto is not intended.

When reuse of a collected used balloon catheter is set as a precondition, the method of recycling a collected used balloon catheter may be determined based on the read result of detection, without making determination as to reusability. When the method of recycling a balloon catheter has uniquely been determined, reusability of a collected used balloon catheter should only be determined based on the read result of detection without determining a method of recycling a collected used balloon catheter.

Though a configuration in which a method of recycling a used balloon catheter is determined based on a read result of detection is described above by way of example, limitation thereto is not intended. The recycling method does not necessarily have to be determined based on the read result of detection. For example, the read result of detection may be used only for determining reusability of collected used balloon catheter 10.

Figure 24:
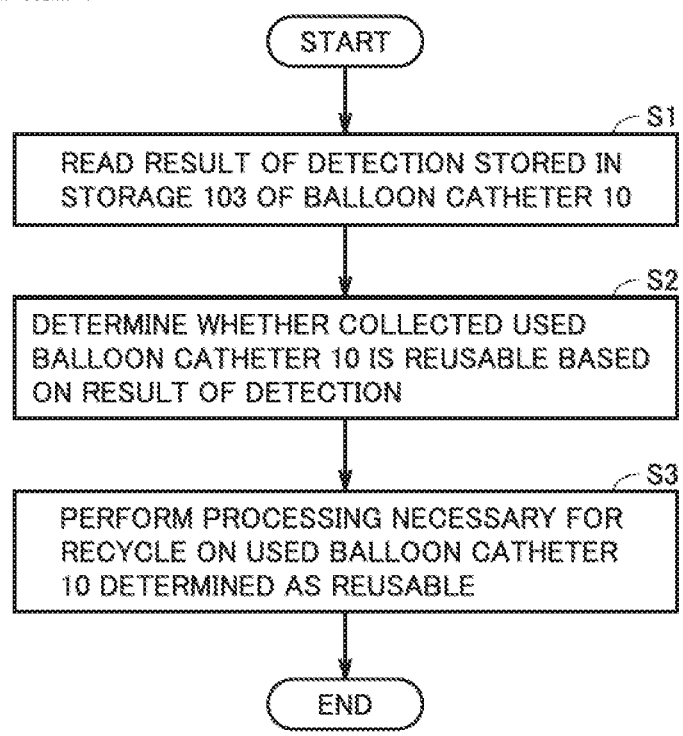
FIG. 24 is a flowchart representing a flow of the recycling processing shown in FIG. 23.

FIG. 24 is a flowchart representing a flow of the recycling processing shown in FIG. 23.

Referring to FIG. 24, in step S1, management apparatus 30 reads a result of detection (history data) stored in storage 103 of balloon catheter 10. In step S2, management apparatus 30 determines whether or not collected used balloon catheter 10 is reusable based on the result of detection. A part of determination as to reusability may be made by a human instead of management apparatus 30. A specific determination method (decision method) will be described later.

In step S3, processing necessary for recycling is performed on used balloon catheter 10 determined as reusable.

Figure 25:
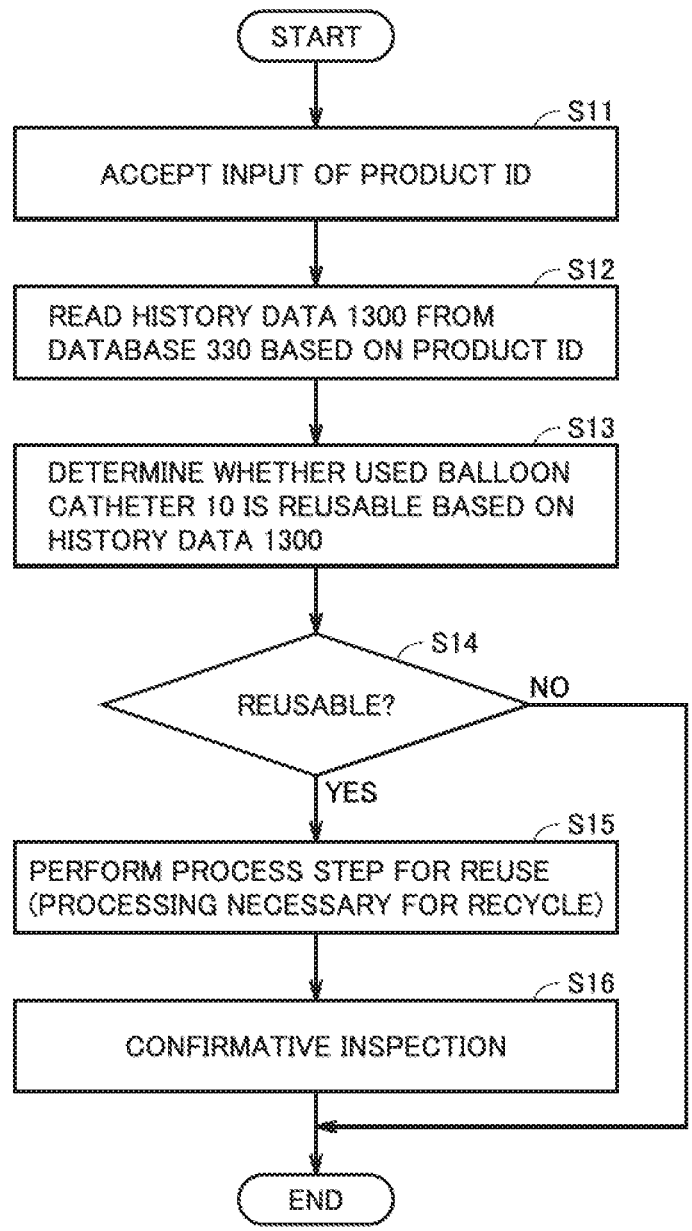
FIG. 25 is a flowchart more specifically representing a series of the processing (except for processing in step S1) shown in FIG. 24.

FIG. 25 is a flowchart more specifically representing a series of the processing (except for processing in step S1) shown in FIG. 24.

Referring to FIG. 25, in step S11, management apparatus 30 accepts input of a product ID from a user. In step S12, management apparatus 30 reads, based on the product ID, history data 1300 with that product ID from database 330 that stores a plurality of pieces of history data 1300.

In step S13, management apparatus 30 determines whether or not used balloon catheter 10 is reusable based on history data 1300.

When balloon catheter 10 is determined as being reusable (YES in step S14), in step S15, a process step for reuse (exemplary "processing necessary for recycling" in step S3 in FIG. 24) is performed by a worker of a maintenance service provider of a balloon catheter, on balloon catheter 10 of which reusability has been determined. Thereafter, in step S16, the worker conducts confirmatory inspection of balloon catheter 10 subjected to the process step in step S15.

When the balloon catheter is determined as being non-reusable (NO in step S14), a series of processing ends and balloon catheter 10 is disposed of.

b2. Determination as to Reusability of Balloon Catheter (1) Condition for Reuse

Details of determination as to reusability in step S13 in FIG. 25 will be described below. Typically, when all of six conditions P1 to P6 below are satisfied, management apparatus 30 determines balloon catheter 10 as being reusable.

Conditions P1 to P6 are exemplary conditions for determining whether or not balloon catheter 10 is reusable, and the number of conditions and contents of the conditions are not limited thereto. For example, whether or not balloon catheter 10 is reusable may be determined without determining whether or not one condition or a plurality of (five or less) conditions of the six conditions of conditions P1 to P6 is/are satisfied.

Another condition may be adopted together with or instead of any one of conditions P1 to P6. Another condition can be set based on data stored in history data 1300 (FIG. 14). For example, together with or instead of condition P5, such a condition that "a rate of increase in pressure has exceeded a predetermined value (upper limit value) in none of cases of use in the past" may be adopted.

P1: An expiration date of use set at the time of manufacturing has not yet come.

P2: A peak value of an applied pressure has exceeded a predetermined value (upper limit value) in none of cases of use in the past.

P3: The number of peak values (the number of times of appearance of peak) equal to or larger than a predetermined value (reference pressure) among pressure peak values has exceeded a reference value in none of cases of use in the past.

P4: Damage (cumulative damage) has exceeded a predetermined value (upper limit value) in none of cases of use in the past.

P5: A rate of lowering in pressure is equal to or higher than a predetermined value (a lower limit value) in all cases of use in the past.

P6: Balloon catheter 10 has been used by a patient with an infectious disease in none of cases of use in the past.

The reason why condition P3 is provided as above is to exclude frequently inflated balloon catheter 10 (frequently inflated sample) from balloon catheters to be reused. The reason why condition P4 is provided is to exclude balloon catheter 10 of which fatigue has developed (high-fatigue sample) from balloon catheters to be reused. Cumulative damage in condition P4 is expressed as a numeric value obtained by integration of an applied pressure with respect to a time period of application. The reason why condition P5 is provided is because a rate of lowering in pressure at an abnormally small value suggests the possibility of deformation or damage which may interfere smooth pressure lowering, which is one of factors that will cause a clinical trouble.

The "predetermined values" in conditions P1 to P5 are different from one another. For example, the predetermined value in condition P1 is larger than the predetermined value in condition P2. The predetermined values are stored in advance in storage 33 of management apparatus 30.

History data 1300 is stored in storage 33 of management apparatus 30. Control unit 32 of management apparatus 30 determines whether or not balloon catheter 10 satisfies conditions P1 to P6 by referring to history data 1300 of balloon catheter 10 of which reusability is to be determined.

Specifically, control unit 32 of management apparatus 30 determines whether or not condition P1 is satisfied based on an expiration date of use included in history data 1300. Control unit 32 determines whether or not condition P2 is satisfied based on peak value data 1302 (see FIG. 14). Furthermore, control unit 32 determines whether or not condition P3 is satisfied based on data 1303 representing the number of times of appearance of a pressure peak.

Control unit 32 determines whether or not condition P4 is satisfied based on data 1306 on cumulative damage. Control unit 32 further determines whether or not condition P5 is satisfied based on data 1307 representing a rate of increase and lowering in pressure.

Management apparatus 30 thus determines whether or not each of conditions P1 to P5 is satisfied based on the history data.

From a point of view of reduction in cost, management apparatus 30 preferably automatically determines whether or not each of conditions P1 to P5 is satisfied when it reads the history data from balloon catheter 10. In connection with conditions P1 to P5, from a point of view of improvement in accuracy in determination, management apparatus 30 preferably updates a numeric value (a predetermined value) that defines each condition by learning a plurality of pieces of history data 1300 with a prescribed learning algorithm.

(2) Details of Condition P6

A method of determination as to condition P6 relating to an infectious disease will now be described. Specifically, a configuration that allows determination as to whether or not balloon catheter 10 has been used for a patient with an infectious disease will be described.

Initially, a configuration that allows determination as to whether or not balloon catheter 10 has been used for a patient with an infectious disease based on an operation by a doctor will be described with reference to FIGS. 26 and 27. Then, a configuration that allows determination as to whether or not balloon catheter 10 has been used for a patient with an infectious disease in coordination with an electronic medical chart system will then be described with reference to FIG. 28. Finally, a configuration that allows determination as to whether or not balloon catheter 10 has been used for a patient with an infectious disease in coordination with a biosensor will be described with reference to FIG. 29.

FIG. 26 is a diagram representing a hub 11G of balloon catheter 10.

Referring to FIG. 26, hub 11G is bent and separated from a main body when force is applied to an end 170 (specifically, an end of a handle). An arrangement is made in advance such that, when a doctor uses balloon catheter 10 for a patient with an infectious disease, the doctor bends end 170 and separates the end from the main body.

According to such a configuration and an arrangement, when balloon catheter 10 from which end 170 is missing is collected, a worker of a maintenance service provider can know that balloon catheter 10 has been used for a patient with an infectious disease. When balloon catheter 10 from which end 170 is not missing is collected, the worker of the maintenance service provider can know that balloon catheter 10 has not been used for a patient with an infectious disease. The worker can determine whether or not condition P6 is satisfied based on presence of end 170.

So long as use of balloon catheter 10 for a patient with an infectious disease can be determined based on physical information, the configuration of balloon catheter 10 is not limited to the configuration shown in FIG. 26.

Figure 27:
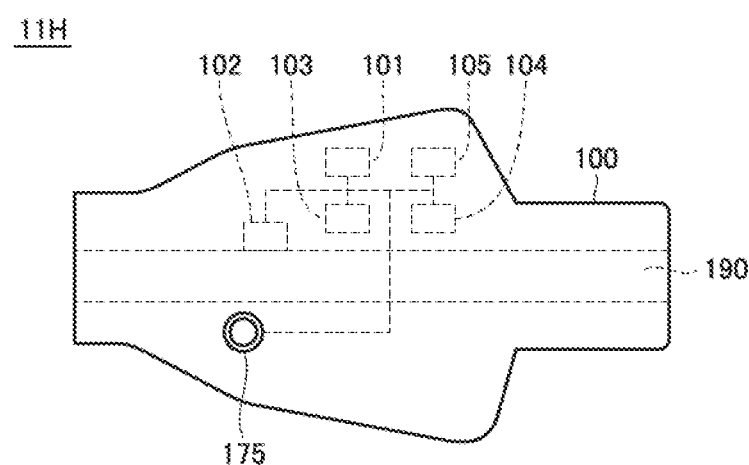
FIG. 27 is a diagram representing a hub of the balloon catheter.

FIG. 27 is a diagram representing a hub 11H of balloon catheter 10.

Referring to FIG. 27, hub 11H includes a button 175. Button 175 is exposed at the surface of housing 100 as being operable by a doctor or the like. When button 175 is pressed, information indicating that the button has been pressed is stored in history data 1300 in storage 103. An arrangement is made in advance such that, when a doctor uses balloon catheter 10 for a patient with an infectious disease, the doctor presses button 175.

According to such a configuration and an arrangement, when management apparatus 30 reads history data 1300 from storage 103 of balloon catheter 10, management apparatus 30 can determine whether or not the button has been pressed based on presence of information indicating pressing of button 175. Management apparatus 30 can determine whether or not balloon catheter 10 has been used for a patient with an infectious disease.

Though an example in which a doctor presses button 175 during surgery is described above by way of example, limitation thereto is not intended. Button 175 may be pressed when management apparatus 30 reads history data 1300 stored in storage 103. Button 175 may be pressed after surgery and before reading by management apparatus 30. Without being limited to a doctor, the button should only be pressed by a person who knows that balloon catheter 10 has been used for a patient with an infectious disease.

So long as use of balloon catheter 10 for a patient with an infectious disease can be determined based on electrical information, the configuration of balloon catheter 10 is not limited to the configuration shown in FIG. 27.

Figure 28:
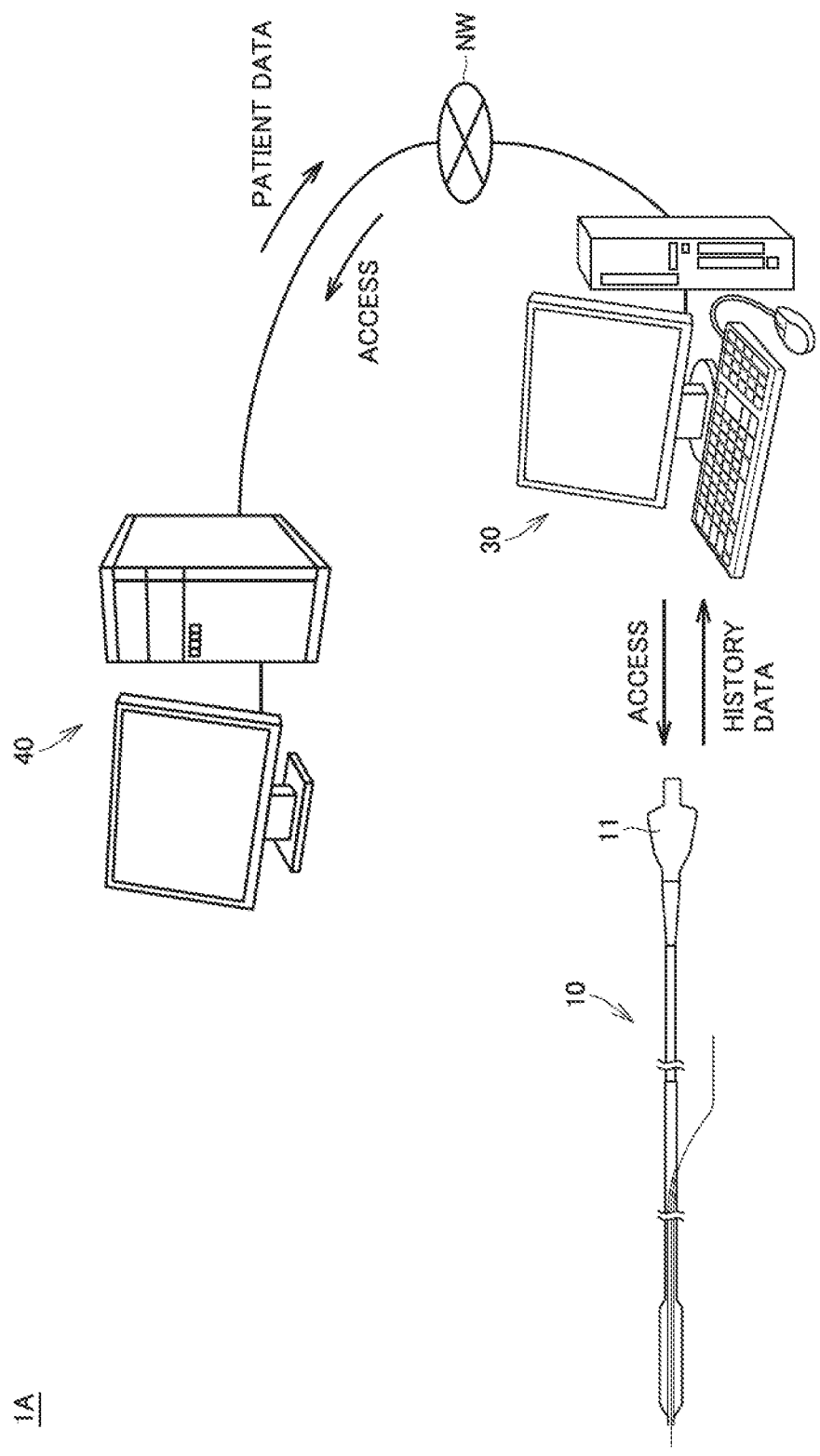
FIG. 28 is a diagram representing a system configuration that allows determination as to whether or not the balloon catheter has been used for a patient with an infectious disease, by being coordinated with an electronic medical chart system.

FIG. 28 is a diagram representing a system configuration that allows determination as to whether or not balloon catheter 10 has been used for a patient with an infectious disease by being in coordination with an electronic medical chart system.

Referring to FIG. 28, an information processing system 1A includes balloon catheter 10, management apparatus 30, and server 40.

Server 40 includes a database including electronic medical charts of a plurality of patients. By making an access from management apparatus 30 to server 40, management apparatus 30 can show an electronic medical chart and update data in server 40.

As described above, management apparatus 30 reads history data (a state value and a result of detection) from collected used balloon catheter 10 and has storage 33 store history data 1300.

Management apparatus 30 accesses server 40 and obtains from server 40, information on an electronic medical chart of a patient (which is also referred to as "patient data" below) for which balloon catheter 10 from which history data 1300 had been read was used. Management apparatus 30 should only obtain at least information indicating whether or not a patient has an infectious disease, among a plurality of pieces of information written in the electronic medical charts.

According to such a configuration, management apparatus 30 can determine whether or not balloon catheter 10 has been used for a patient with an infectious disease. In order to perform such processing, a product ID of balloon catheter 10 that will be used and identification information of a patient should only be associated with each other in advance in server 40 or management apparatus 30.

Though a configuration in which information on the electronic medical chart is transmitted from server 40 to management apparatus 30 is described above by way of example, patient data in server 40 may be stored in storage 103 of balloon catheter 10, without management apparatus 30 being interposed.

Patient data may be stored in storage 103 of balloon catheter 10 before or after use of balloon catheter 10 and before transfer of history data 1300 to management apparatus 30. Such processing for storing patient data in storage 103 can be performed, for example, by downloading patient data from server 40 to balloon catheter 10. Communication between server 40 and balloon catheter 10 may be wireless or wired.

According to such a configuration, as management apparatus 30 reads patient data together with history data 1300 from balloon catheter 10, management apparatus 30 can determine whether or not balloon catheter 10 from which history data 1300 is read has been used for a patient with an infectious disease, without accessing server 40.

Figure 29:
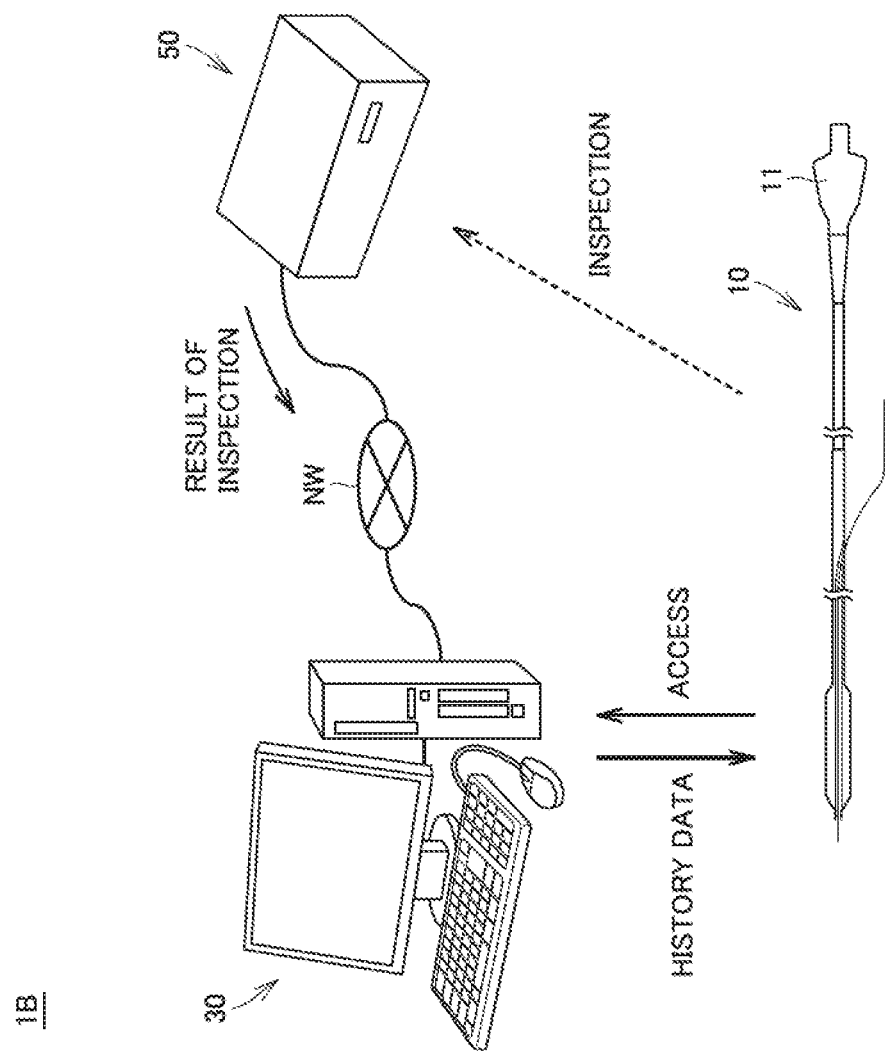
FIG. 29 is a diagram representing a system configuration that allows determination as to whether or not the balloon catheter has been used for a patient with an infectious disease, by being coordinated with a biosensor.

FIG. 29 is a diagram representing a system configuration that allows determination as to whether or not balloon catheter 10 has been used for a patient with an infectious disease, by being in coordination with a biosensor. Specifically, FIG. 29 is a diagram representing a system configuration for inspecting for a substance remaining in used balloon catheter 10 that causes an infectious disease.

Referring to FIG. 29, an information processing system 1B includes balloon catheter 10, management apparatus 30, and a biosensor 50.

For example, an external force-assisted near-field illumination biosensor can be adopted as biosensor 50. Such biosensor 50 can create a "moving light spot" by a magnet and near-field illumination by causing magnetic fine particles and fine particles that scatter light to adhere to a biological substance (virus) to be detected, to thereby detect the biological substance.

A worker of a maintenance service provider uses such biosensor 50 to inspect for viruses adhering to balloon catheter 10. Specifically, the worker inspects for viruses adhering to balloon catheter 10 that cause an infectious disease.

A result of inspection is transmitted, for example, from biosensor 50 to management apparatus 30 over network NW. A manner for management apparatus 30 to obtain a result of inspection is not limited to the manner over network NW. For example, a result of inspection may be stored together with a product ID in an electronic recording medium other than carrier waves and read by management apparatus 30. Alternatively, a result of inspection may be written on a recording medium such as paper and the worker may record incidence of an infectious disease in association with history data 1300 in management apparatus 30 by referring to the record on the paper.

According to such a configuration, management apparatus 30 can determine whether or not balloon catheter 10 has been used for a patient with an infectious disease.

Though a configuration in which a result of inspection is transmitted from biosensor 50 to management apparatus 30 is described above by way of example, the result of inspection may be stored in storage 103 of balloon catheter 10 without management apparatus 30 being interposed.

The result of inspection may be stored in storage 103 of balloon catheter 10 before or after use of balloon catheter 10 and before transfer of history data 1300 to management apparatus 30. Such processing for storing the result of inspection in storage 103 can be performed, for example, by downloading the result of inspection from biosensor 50 to balloon catheter 10. Communication between biosensor 50 and balloon catheter 10 may be wireless or wired.

According to such a configuration, as management apparatus 30 reads the result of inspection together with history data 1300 from balloon catheter 10, management apparatus 30 can determine whether or not balloon catheter 10 from which history data 1300 has been read had been used for a patient with an infectious disease without accessing biosensor 50.

(3) Summary

A part of determination processing in a first stage is summarized as below.

In connection with condition P1, storage 103 of balloon catheter 10 further includes expiration information that represents an expiration date of use of balloon catheter 10. A method of recycling balloon catheter 10 further includes reading the expiration information from storage 103 and determining whether or not balloon catheter 10 is reusable based on the expiration information.

In connection with condition P2, the result of detection (the history data and the state value) includes a pressure peak value. In determining whether or not balloon catheter 10 is reusable (step S2 in FIG. 24 and step S13 in FIG. 25), when the peak value exceeds a predetermined threshold value, balloon catheter 10 is determined as being non-reusable.

In connection with condition P3, the result of detection includes number information that represents the number of peak values equal to or larger than a predetermined threshold value, among pressure peak values (data 1303 that represents the number of times of appearance of a pressure peak). In determining whether or not balloon catheter 10 is reusable, when the number of peak values exceeds a predetermined threshold value, balloon catheter 10 is determined as being non-reusable.

In connection with condition P4, the result of detection includes a calculation value (data 1306 on cumulative damage) obtained by integrating a pressure with respect to a time period of pressure application. In determining whether or not balloon catheter 10 is reusable, balloon catheter 10 is determined as being non-reusable when the calculation value exceeds a predetermined threshold value.

In connection with condition P5, the result of detection includes rate information that represents a rate of lowering in pressure (data 1307 representing a rate of increase and lowering in pressure). In determining whether or not balloon catheter 10 is reusable, balloon catheter 10 is determined as being non-reusable when the rate of lowering in pressure is lower than a predetermined threshold value.

In connection with condition P6, storage 103 of balloon catheter 10 can store use history information that represents use of the balloon catheter for a patient with an infectious disease. The method of recycling balloon catheter 10 includes reading use history information from storage 103 and determining whether or not balloon catheter 10 is reusable based on the use history information.

The use history information is information representing, for example, pressing of button 175 (see FIG. 27). Alternatively, the use history information is patient data (see FIG. 28). Alternatively, the use history information is a result of inspection by biosensor 50 (see FIG. 29). Management apparatus 30 may obtain the use history information from server 40 (FIG. 28) or biosensor 50 (FIG. 29) instead of balloon catheter 10.

b3. Method of Recycling Balloon Catheter

Details of the method of recycling a balloon catheter will now be described. Specifically, details of a process step for reuse shown in step S15 in FIG. 25 will be described.

During surgery, balloon catheter 10 comes in contact with blood, a contrast agent, physiological saline, heparin, and a peptic juice. Therefore, after the surgery, blood and the contrast agent coagulate and firmly adhere to balloon catheter 10.

Therefore, from a point of view of reuse of balloon catheter 10, five steps of a washing step, a drying step, an inspection step, a sterilization step, and a step of rewriting a product ID are required as the process step in step S15 in FIG. 25.

For balloon catheter 10 in the present example, normally, it is not realistic to disassemble balloon catheter 10 and assemble the balloon catheter again, and it is also difficult to replace some of parts. The process step in step S15, however, may include such a step.

When balloon 14 is of a pharmaceutical drug application type, a step of applying a pharmaceutical drug is separately required. When balloon 14 is of a stent delivery type, a step of mounting a new stent is separately required.

In such a process step, processing based on history data 1300 can also be performed. For example, the number of inspection items may be increased or decreased depending on a history of use (a maximum inflation pressure, the number of times of inflation, or a time period of use) shown in history data 1300. Alternatively, the number of criteria in inspection may be increased or decreased depending on a history of use.

For example, at least one of a time period of washing and the number of times of washing of balloon catheter 10 may also be determined based on history data 1300. In determining the method of recycling the balloon catheter, at least one of the number of times of washing and the time period of washing of balloon catheter 10 may also be determined.

For example, as the number of times of appearance of the peak is larger, at least one of the number of times of washing and a time period of washing may also be increased. As a total time period of application of a pressure is longer, at least one of the number of times of washing and a time period of washing may also be increased. Alternatively, as cumulative damage is higher, at least one of the number of times of washing and a time period of washing may also be increased. Alternatively, the number of times of inflation is larger, at least one of the number of times of washing and a time period of washing may also be increased. Alternatively, as a peak value is larger, at least one of the number of times of washing and a time period of washing may also be increased.

b4. Confirmatory Inspection Before Shipment of Product

After the process step above ends, confirmatory inspection before shipment of balloon catheter 10 is carried out as shown in step S16 in FIG. 25. In other words, determination as to quality assurance (determination as to shipment) of balloon catheter 10 determined as recyclable is made. Specifically, when all of three conditions P7 to P9 below are satisfied, balloon catheter 10 is determined as passing confirmatory inspection.

P7: In a pressure test, a prescribed pressure can be maintained for a certain period of time.

P8: In a pressure responsiveness test, an outer diameter of a balloon within a prescribed range is maintained at the time of application of a reference pressure.

P9: In visual inspection, a shape, an outer diameter, and a degree of bending of balloon catheter 10 satisfy criteria (are within prescribed ranges).

The pressure test in condition P7 and the pressure responsiveness test in condition P8 are conducted with the use of dedicated equipment (not shown). Visual inspection is conducted, for example, manually by a worker rather than by a machine. Without being limited as such, visual inspection may be conducted as nondestructive inspection with the use of equipment. In such nondestructive inspection, for example, ultrasonic waves, radiation, radar, or an optical interferometric surface profiling apparatus can be used.

A result of the pressure test, a result of the pressure responsiveness test, and a result of visual inspection may be stored in storage 103 of balloon catheter 10. According to such a configuration, these results can later be checked by reading them from storage 103.

The results are preferably read by management apparatus 30 as a part of history data 1300. According to such a configuration, management apparatus 30 can have storage 33 store the results with balloon catheter 10 being interposed.

The results may be stored in management apparatus 30 in association with a product ID, without balloon catheter 10 being interposed.

As set forth above, the method of recycling collected used balloon catheter 10 further includes determining whether or not balloon catheter 10 can be shipped based on a result of the pressure test of balloon catheter 10.

The method of recycling balloon catheter 10 further includes determining whether or not an outer diameter of the balloon of balloon catheter 10 is within a prescribed range at the time of application of a reference pressure and determining whether or not balloon catheter 10 can be shipped based on a result of determination.

The method of recycling balloon catheter 10 further includes determining whether or not balloon catheter 10 can be shipped based on a result of visual inspection of balloon catheter 10.

C. Medical Assistance

Medical assistance for doctors, nurses, or technicians by making use of a balloon catheter will be described. Specifically, medical assistance will be described for each of a function of notification by using a balloon catheter (assistance at the time of use of the balloon catheter), a function to automatically regulate a pressure in the balloon catheter, procedural assistance in medical clerical works, and clinical research assistance.

c1. Notification Function

Figure 30:
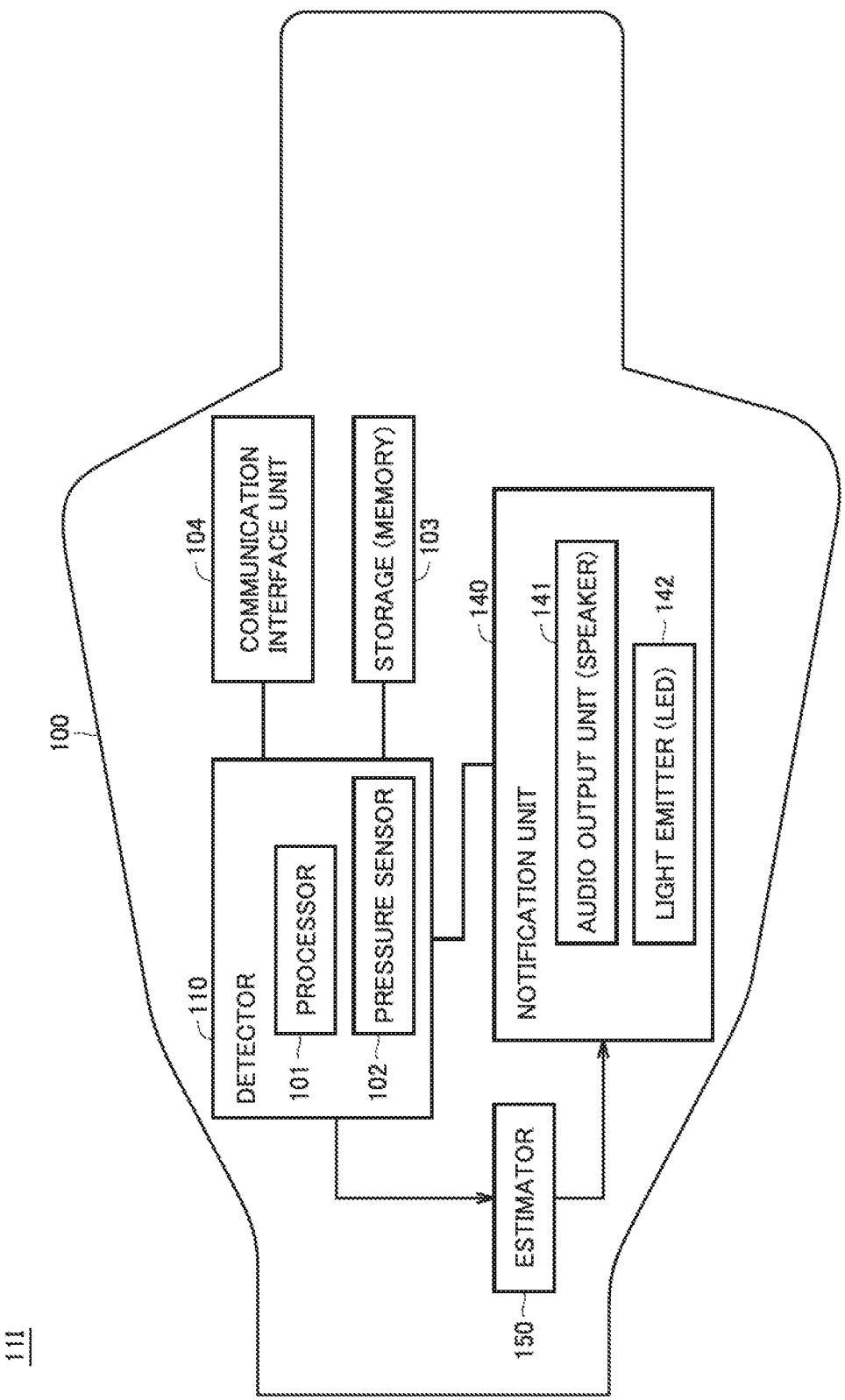
FIG. 30 is a diagram for illustrating a hub with a notification function.

FIG. 30 is a diagram for illustrating a hub with a notification function.

Referring to FIG. 30, balloon catheter 10 includes a hub 11I instead of hub 11. Hub 11I includes detector 110, storage 103, communication interface unit 104, a notification unit 140, and an estimator 150. Notification unit 140 includes an audio output unit 141 and a light emitter 142. Audio output unit 141 is typically implemented by a speaker. Light emitter 142 is typically implemented by a light emitting diode (LED). Notification unit 140 gives a notification about a state of pressure application in pipe path 190. Exemplary notification of the state of pressure application with the use of such notification unit 140 will be described below.

(1) First Example

When there is a point of leakage in balloon catheter 10, balloon catheter 10 is unable to maintain an internal pressure (pressure in pipe path 190). A doctor could immediately notice large leakage. The doctor, however, may not notice small leakage or pinhole rupture.

Balloon catheter 10 detects (measures) a pressure in pipe path 190 by means of detector 110. Therefore, a defect in a product can be sensed in real time based on a result of detection.

From such a point of view, estimator 150 of hub 11I estimates leakage of a solution contained in pipe path 190 to the outside of pipe path 190 based on variation in detected pressure. When estimator 150 senses lowering in pressure at a rate within a prescribed range after increase in pressure to a certain value or higher, estimator 150 estimates leakage of the solution to the outside of pipe path 190.

Notification unit 140 gives a predetermined notification based on estimation of occurrence of leakage by estimator 150. For example, audio output unit 141 emits alarm sound. Alternatively, light emitter 142 blinks. Notification unit 140 may cause emission of alarm sound and blinking.

According to such a configuration, balloon catheter 10 can immediately notify a doctor of leakage. Balloon catheter 10 may change the notification method depending on magnitude of leakage.

Estimator 150 is implemented by computation processing by a processor (not shown). Though a configuration in which estimator 150 is provided separately from detector 110 is described above by way of example, limitation thereto is not intended. Detector 110 may include estimator 150 and estimator 150 may be implemented by processing by processor 101.

(2) Second Example

When a pressure in pipe path 190 detected by detector 110 exceeds a rated burst pressure (RBP) of balloon catheter 10, notification unit 140 gives a predetermined notification. Processor 101 typically determines whether or not the pressure has exceeded the rated burst pressure. For example, notification unit 140 has audio output unit 141 emit alarm sound. Alternatively, light emitter 142 blinks. Notification unit 140 may cause emission of alarm sound and blinking.

According to such a configuration, labor by a doctor, a nurse, or a technician who cares a patient can be lessened.

(3) Third Example

On condition that a pressure (a pressure equal to or higher than a prescribed pressure) is applied to pipe path 190, notification unit 140 gives an aural notification about a value of the pressure. Such a configuration leads to lessening of labor by a doctor, a nurse, or a technician.

(4) Fourth Example

On condition that a pressure is applied to pipe path 190 and the pressure is constant (a pressure within a prescribed range), notification unit 140 gives a notification about elapsed time since the pressure attained to the constant pressure. Lapse of time is counted by a clock (not shown) stored in detector 110.

According to such a configuration, a doctor, a nurse, or a technician can be notified of a duration of inflation of a balloon after the pressure in pipe path 190 of balloon catheter 10 is maintained constant. Therefore, labor by a doctor, a nurse, or a technician can be lessened.

An example in which hub 111 includes piezoelectric element 102A instead of pressure sensor 102 is also applicable to each example (the first to fourth examples). When the situation shown in each example occurs, a pressure is applied to piezoelectric element 102A and hence electric power can be supplied to processor 101, notification unit 140, and the like.

(5) Fifth Example

Figure 31:
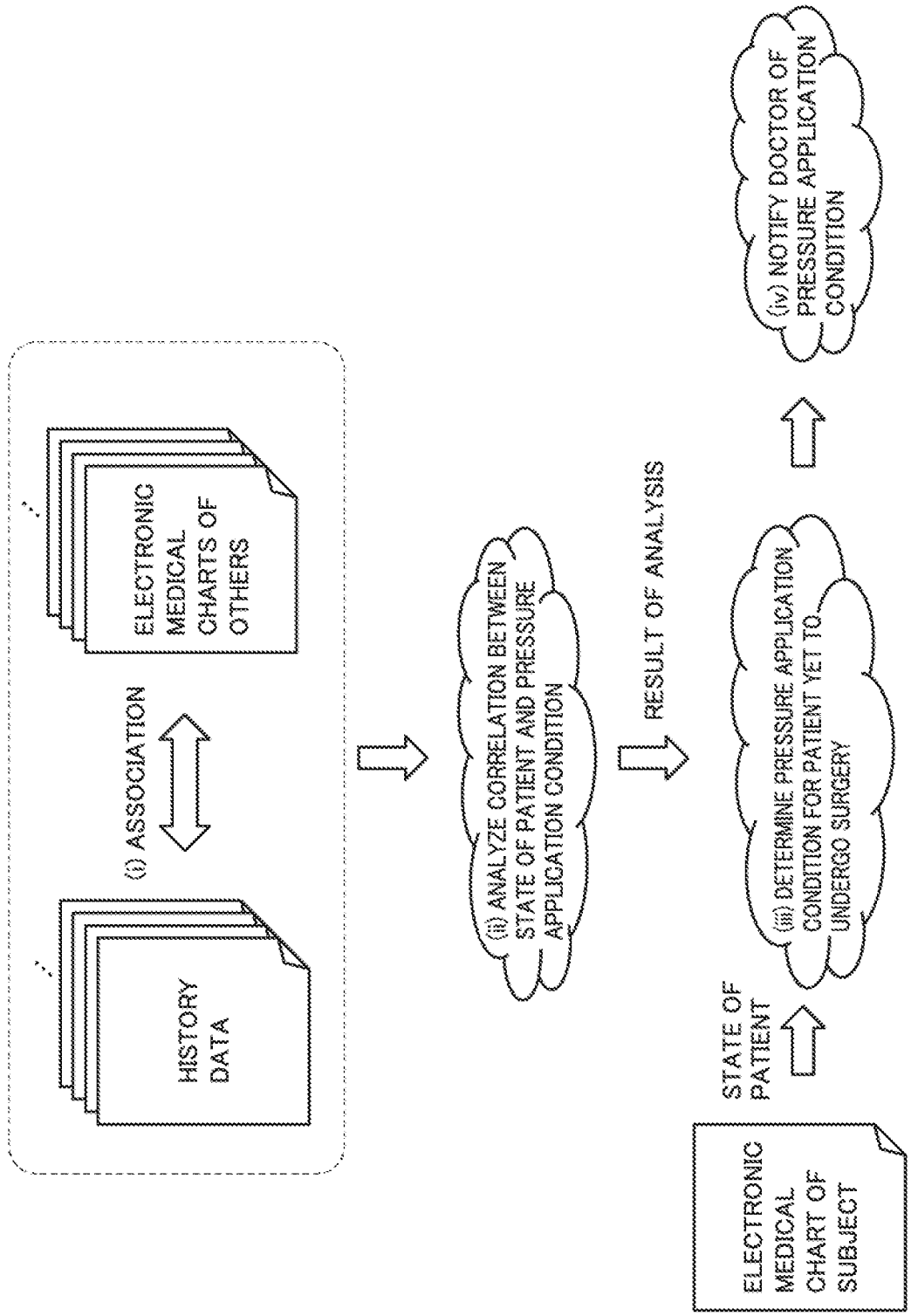
FIG. 31 is a diagram for illustrating an approach to notification of an optimal pressure application condition to a doctor.

FIG. 31 is a diagram for illustrating an approach to notification of an optimal pressure application condition to a doctor. The pressure application condition is defined as change over time in applied pressure. A constant pressure may be defined as the pressure application condition.

Referring to FIG. 31, management apparatus 30 associates a plurality of pieces of history data 1300 with electronic medical charts of a plurality of patients who underwent surgery in the past. Typically, as shown in a state (i), management apparatus 30 associates the plurality of pieces of history data 1300 with the electronic medical charts of the patients (electronic medical charts of others) other than a patient yet to undergo surgery (which is also referred to as a "subject" below). Specifically, for each of patients (which are also referred to as "other patients" below) other than the subject, history data 1300 of each of the patients detected by balloon catheter 10 is associated with the electronic medical chart of that patient. More specifically, among pieces of history data 1300 of other patients, data representing change over time in pressure (for example, time-series data 111 shown in FIG. 13) and the electronic medical chart are associated with each other.

Then, as shown in a state (ii), management apparatus 30 analyzes correlation between the pressure application condition and states of other patients. The states of other patients include vital signs after surgery (a pulse rate or a heart rate, a respiration rate, a blood pressure, a body temperature, and a level of consciousness). Analysis described above may be conducted with age, sex, or weight of other patients being included in the state of the patient. A result of analysis is expressed, for example, by a function where a vital sign is defined as an input (parameter) and a pressure application condition is defined as an output.

Furthermore, analysis described above may be conducted, with a past medical history (for example, diabetes or cardiovascular diseases) of other patients, history of smoking, a position of an affected area of a patient that is to be treated, a state of the affected area, a history of treatment around the affected area, a diagnosis image at the time of inspection before treatment, and data on analysis of the image being included in the state of the patient.

After analysis above, as shown in a state (iii), management apparatus 30 determines the pressure application condition for the patient based on the result of analysis described above and the state of the subject. When the pressure application condition for the patient yet to undergo surgery is determined, management apparatus 30 notifies a doctor of the pressure application condition as shown in a state (iv).

Though a configuration in which analysis is conducted by using electronic medical charts of others is described above by way of example, limitation thereto is not intended. The pressure application condition may be determined based on the electronic medical chart of the subject and one piece or a plurality of pieces of history data 1300 in the past of the subject patient.

Though a configuration in which management apparatus 30 conducts analysis described above and determines the pressure application condition is described above by way of example, limitation thereto is not intended. For example, server 40 may conduct analysis described above and determine the pressure application condition. In this case, the electronic medical chart does not have to be downloaded to management apparatus 30. A not-shown information processing apparatus other than management apparatus 30 may conduct analysis described above and determine the pressure application condition.

FIG. 32 is a diagram for illustrating a method of notifying a doctor of a pressure application condition.

As shown in FIG. 32 (A), the determined pressure application condition may be shown on a terminal apparatus 60 communicatively connected to server 40 and management apparatus 30 and used by a doctor. Alternatively, as shown in FIG. 32 (B), terminal apparatus 60 may notify a hub 11J including a display 143 of the determined pressure application condition through network NW, and hub 11J may show the pressure application condition on display 143. Management apparatus 30 may notify balloon catheter 10 of the determined pressure application condition without terminal apparatus 60 being interposed.

When the pressure application condition is shown on display 143 of balloon catheter 10, management apparatus 30 may specify in advance which balloon catheter 10 is to show the pressure application condition, based on the product ID. Thereafter, management apparatus 30 may notify terminal apparatus 60 of a result of specifying. Alternatively, after the pressure application condition is determined, balloon catheter 10 that has communicated with terminal apparatus 60 may show the determined pressure application condition.

With representation shown in FIG. 32 (A) and (B), a doctor can know an optimal pressure application condition before surgery. In particular, as shown in FIG. 32 (B), by showing the pressure application condition on display 143 of balloon catheter 10, the doctor does not have to check terminal apparatus 60.

Figure 33:
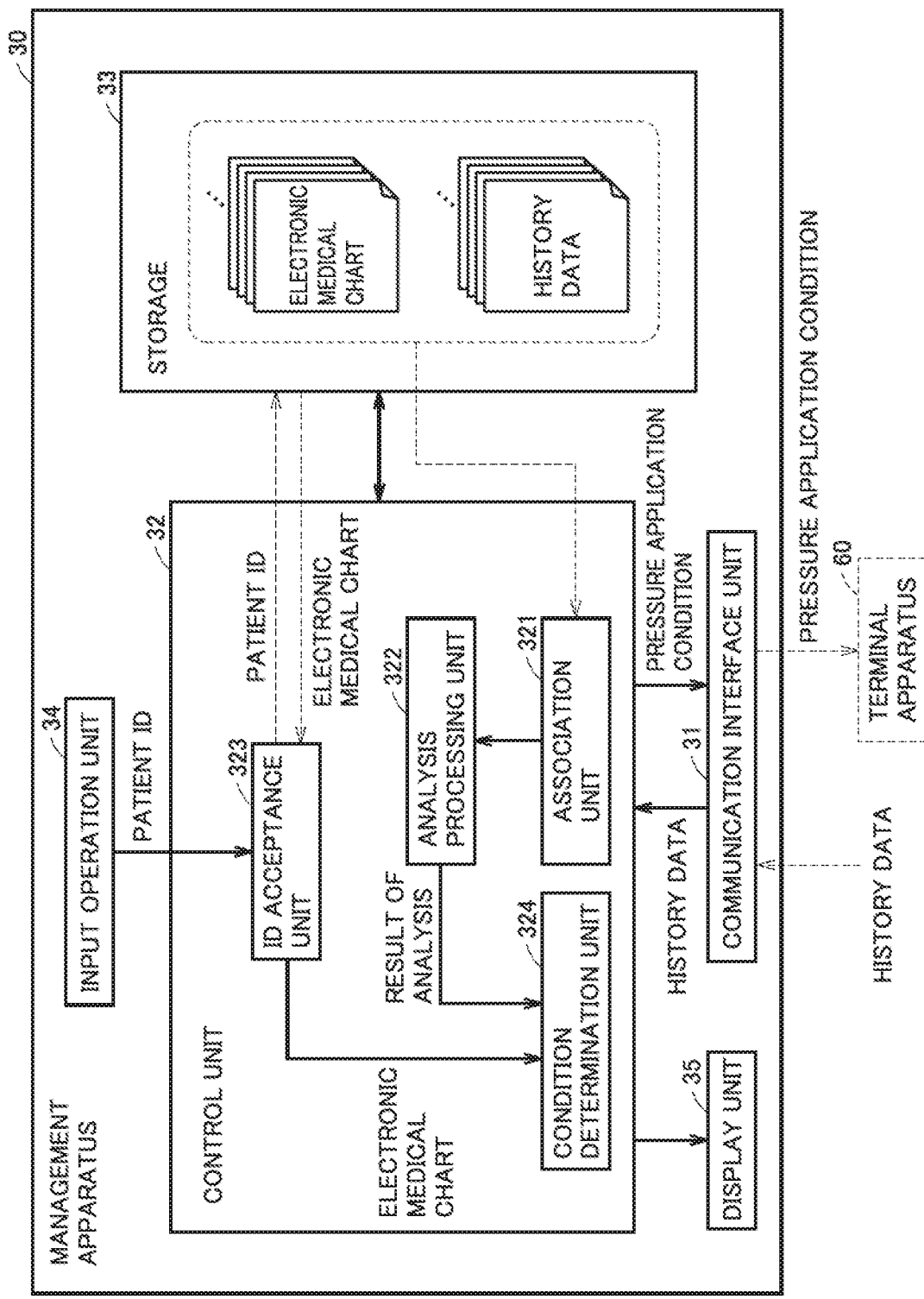
FIG. 33 is a diagram for illustrating a functional configuration of the management apparatus that can determine a pressure application condition.

FIG. 33 is a diagram for illustrating a functional configuration of management apparatus 30 that can determine a pressure application condition.

Referring to FIG. 33, management apparatus 30 includes communication interface unit 31, control unit 32, and storage 33 as shown in FIG. 16. Management apparatus 30 further includes an input operation unit 34 and a display unit 35.

Control unit 32 includes an association unit 321, an analysis processing unit 322, an ID acceptance unit 323, and a condition determination unit 324. Storage 33 stores a plurality of pieces of history data 1300 and a plurality of electronic medical charts. The electronic medical chart is downloaded in advance from server 40.

The input operation unit accepts input of a patient ID. The patient ID is sent to ID acceptance unit 323.

ID acceptance unit 323 extracts from storage 103, an electronic medical chart linked to the accepted patient ID based on the patient ID. ID acceptance unit 323 sends the extracted electronic medical chart to condition determination unit 324.

Communication interface unit 31 receives history data 1300 from balloon catheter 10 as described above (see FIG. 16). History data 1300 is sent to control unit 32 and thereafter stored in storage 103.

Association unit 321 associates the plurality of pieces of history data 1300 with the electronic medical charts of the plurality of patients as described above. Association unit 321 sends the associated data to analysis processing unit 322.

Analysis processing unit 322 analyzes correlation between the pressure application condition and the state of the patient who underwent surgery as described above. Analysis processing unit 322 sends a result of analysis to condition determination unit 324.

Condition determination unit 324 determines an optimal pressure application condition based on the result of analysis and the electronic medical chart (the electronic medical chart of the patient who will have surgery).

The determined pressure application condition is sent to terminal apparatus 60 or the like through communication interface unit 31.

Processing performed by a functional block included in control unit 32 may be performed by server 40, terminal apparatus 60, or a not-shown information processing apparatus connected to server 40, rather than management apparatus 30.

c2. Automatic Pressure Regulation Function

Management apparatus 30 may control an operation of the inflation device with terminal apparatus 60 being interposed, such that a pressure is actually applied to satisfy the determined pressure application condition.

Figure 34:
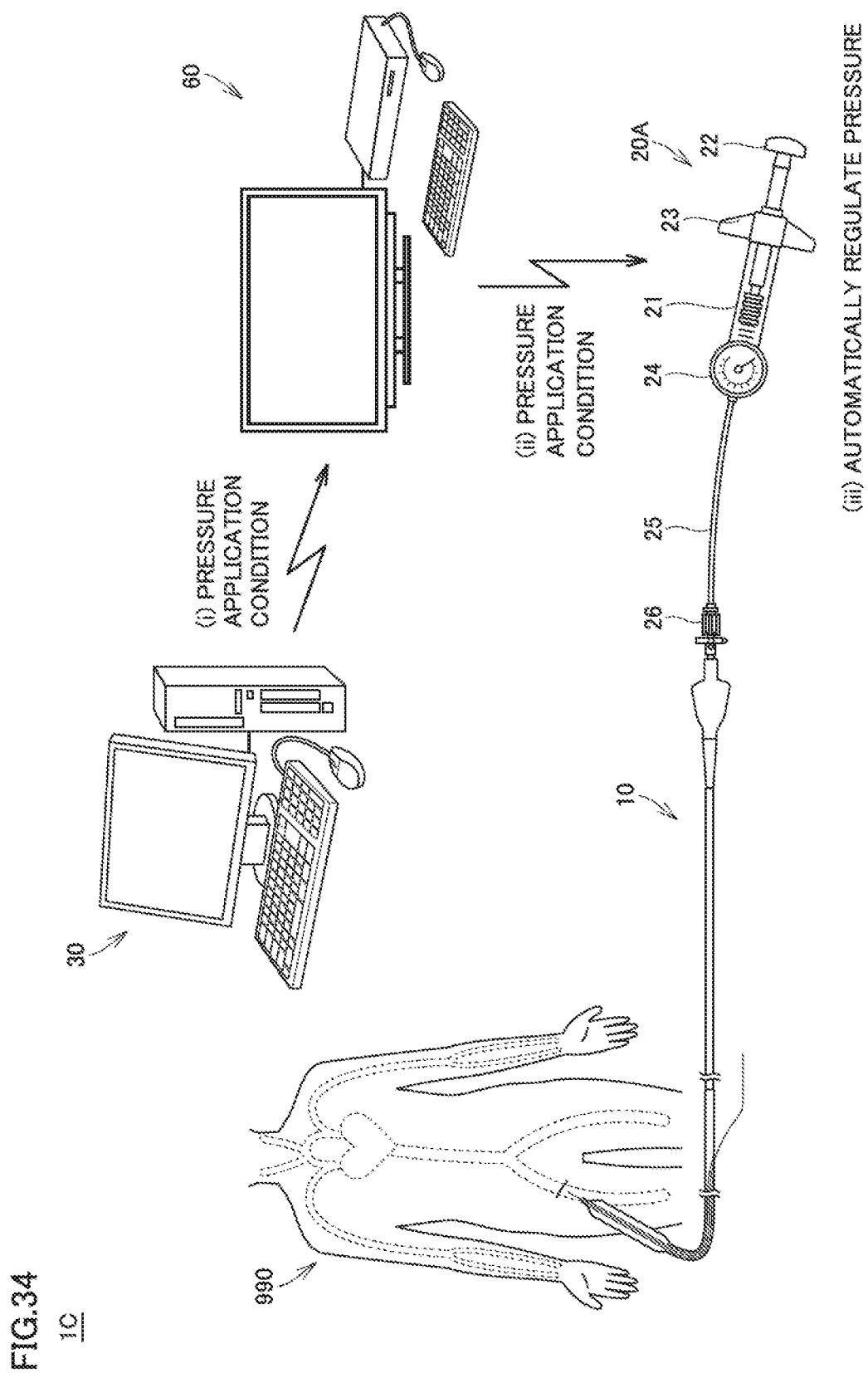
FIG. 34 is a diagram for illustrating automatic control of an inflation device.

FIG. 34 is a diagram for illustrating automatic control of an inflation device.

Referring to FIG. 34, an information processing system 1C includes balloon catheter 10, inflation device 20A, management apparatus 30, server 40 (not shown), and terminal apparatus 60.

As shown in states (i) and (ii), management apparatus 30 notifies inflation device 20A of a pressure application condition determined thereby, with terminal apparatus 60 used by a doctor being interposed.

Inflation device 20A includes a mechanism that regulates a pressure to be applied to balloon catheter 10. Specifically, when inflation device 20A receives the pressure application condition from terminal apparatus 60, it automatically activates piston 22 such that a pressure measured by gauge 24 attains to the pressure indicated by the pressure application condition.

For automatic regulation of the pressure described above after balloon catheter 10 is set at a treatment position within the body of patient 990, inflation device 20A is preferably provided with a mechanism such as a button for indicating start of automatic regulation.

Figure 35:
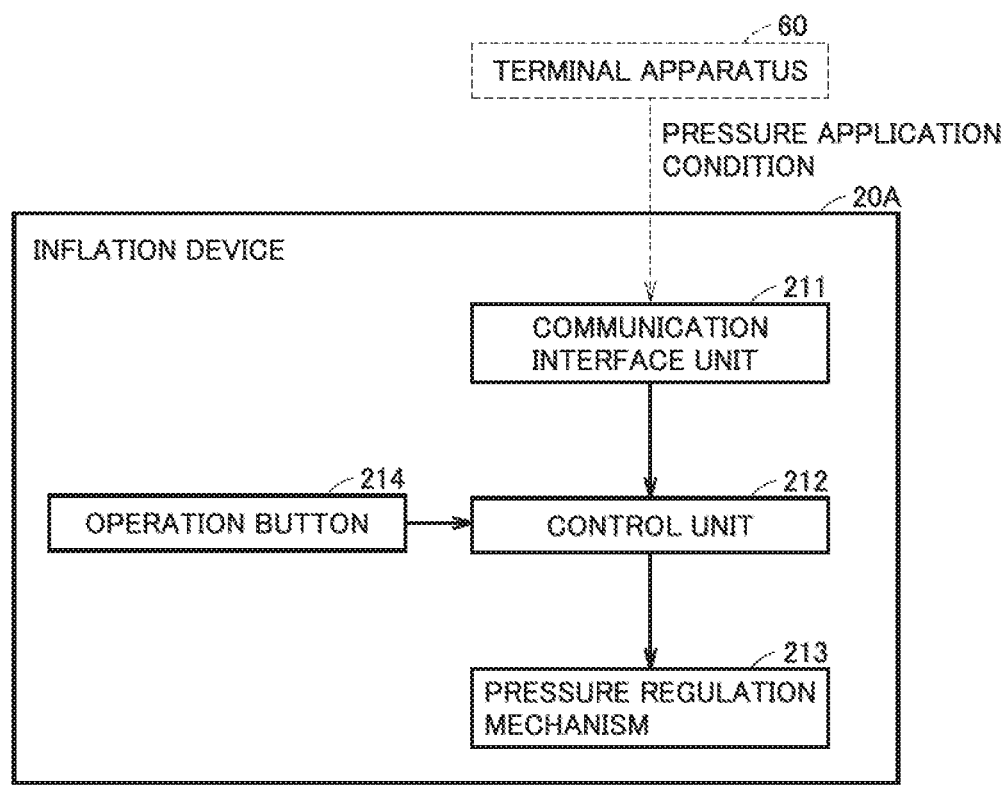
FIG. 35 is a diagram for illustrating a configuration of the inflation device.

FIG. 35 is a diagram for illustrating a configuration of inflation device 20A.

Referring to FIG. 35, inflation device 20A includes a communication interface unit 211, a control unit 212, a pressure regulation mechanism 213, and an operation button 214 as an operation portion.

Communication interface unit 211 receives a pressure application condition from management apparatus 30 with terminal apparatus 60 being interposed.

On condition that an operation onto operation button 214 is performed, control unit 212 transmits a drive command in accordance with the pressure application condition to the pressure regulation mechanism.

As pressure regulation mechanism 213 is driven, a pressure in accordance with the pressure application condition is applied to pipe path 190 in balloon catheter 10.

Thus, information processing system 1C further includes inflation device 20A that injects a solution into balloon catheter 10. Management apparatus 30 notifies inflation device 20A of the determined pressure application condition with terminal apparatus 60 being interposed. Inflation device 20A injects the solution into balloon catheter 10 such that the pressure in pipe path 190 in balloon catheter 10 satisfies the determined pressure application condition.

According to such a configuration, an operation by a doctor onto the inflation device can be simplified and balloon 14 can be inflated at an appropriate pressure.

c3. Clerical Procedure Assistance

(1) First Example

When surgery for a patient using balloon catheter 10 is performed, a doctor or a nurse records clinical courses and cares on prescribed paper (specifically, paper for recording catheter inspection and treatment). To this paper, a label showing information essential for claiming insurance (which is also referred to as "essential information" below) should be stuck. The essential information includes information on a name of a manufacturer, a lot number, or a catalog number. Convenience is further enhanced by printing not only the essential information but also a history of use of the product (a maximum inflation pressure, the number of times of inflation, and time of use).

Currently, a portion containing the essential information recorded on a storage box of balloon catheter 10 is separated from the storage box and the separated portion is stuck to the paper. Typically, the essential information is printed on the storage box itself. Therefore, separation requires scissors or the like and an adhesive such as glue is required for sticking. Though the portion containing the essential information may be arranged on a storage box as a seal, bothersome works still remain. The number of seals that can be prepared in advance is also limited.

A configuration that assists works for sticking essential information to paper will be described below.

Figure 36:
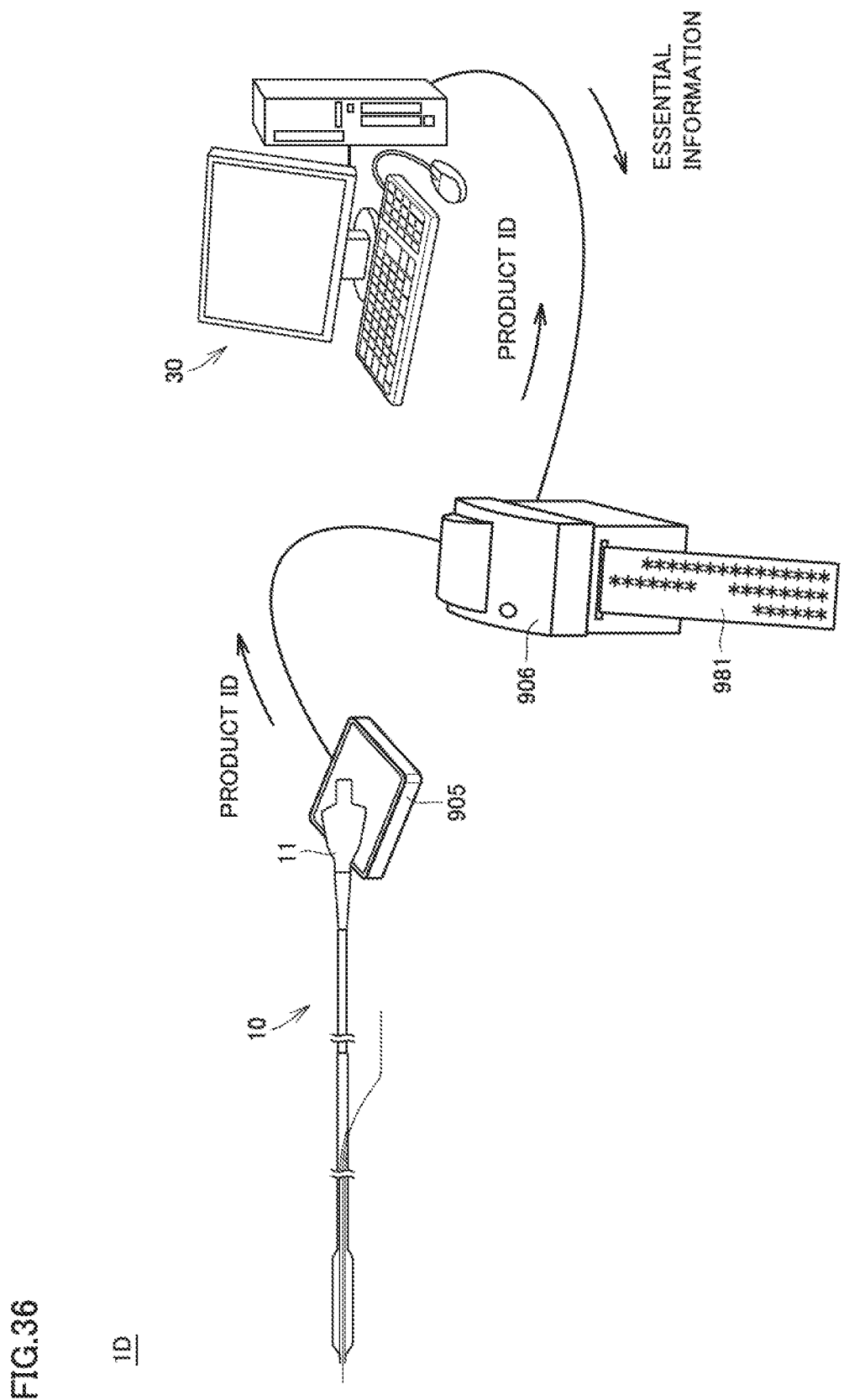
FIG. 36 is a diagram for illustrating a schematic configuration of an information processing system that can provide clerical procedure assistance.

FIG. 36 is a diagram for illustrating a schematic configuration of an information processing system that can provide clerical procedure assistance.

Referring to FIG. 36, an information processing system 1D includes balloon catheter 10, a printer 906, a data reader 905, management apparatus 30, and not-shown server 40.

Management apparatus 30 can communicate with printer 906. Management apparatus 30 further stores essential information in association with each product ID. When a product ID is designated, management apparatus 30 can thus identify corresponding essential information.

Data reader 905 is communicatively connected to printer 906. A form of connection may be wired or wireless.

When hub 11 of balloon catheter 10 comes closer to data reader 905, data reader 905 establishes contactless communication with communication interface unit 104 of hub 11. Through contactless communication, data reader 905 reads the product ID from storage 103 of hub 11.

Printer 906 receives the product ID from data reader 905. Printer 906 transmits the product ID to management apparatus 30.

Management apparatus 30 identifies essential information associated with the product ID received from printer 906, from among a plurality of pieces of essential information stored in advance in storage 33. Management apparatus 30 transmits the identified essential information to printer 906.

When printer 906 receives the essential information from management apparatus 30, it prints the essential information on a recording medium. Typically, printer 906 is an apparatus that makes printing on a seal, and prints the essential information on a seal. A doctor or a nurse separates from printer 906, a seal 981 on which the essential information has been printed, together with a seal mount (release paper).

FIG. 37 is a diagram representing exemplary paper for recording catheter inspection and treatment.

Referring to FIG. 37, paper 980 includes at least a field where time is to be written and a field where clinical course records are to be written.

As treatment with a catheter is performed, seal 981 output from printer 906 is separated from the seal mount as a result of a series of processing described with reference to FIG. 36, and thereafter a doctor or a nurse sticks seal 981 to the field where the clinical course records are to be written.

When information on a guide wire that was used is stored in management apparatus 30, printer 906 may print essential information on the guide wire on a seal. In this case as well, a doctor or a nurse sticks a seal 982 on which essential information has been printed to a field in paper 980 where the clinical course records are to be written.

Figure 38:
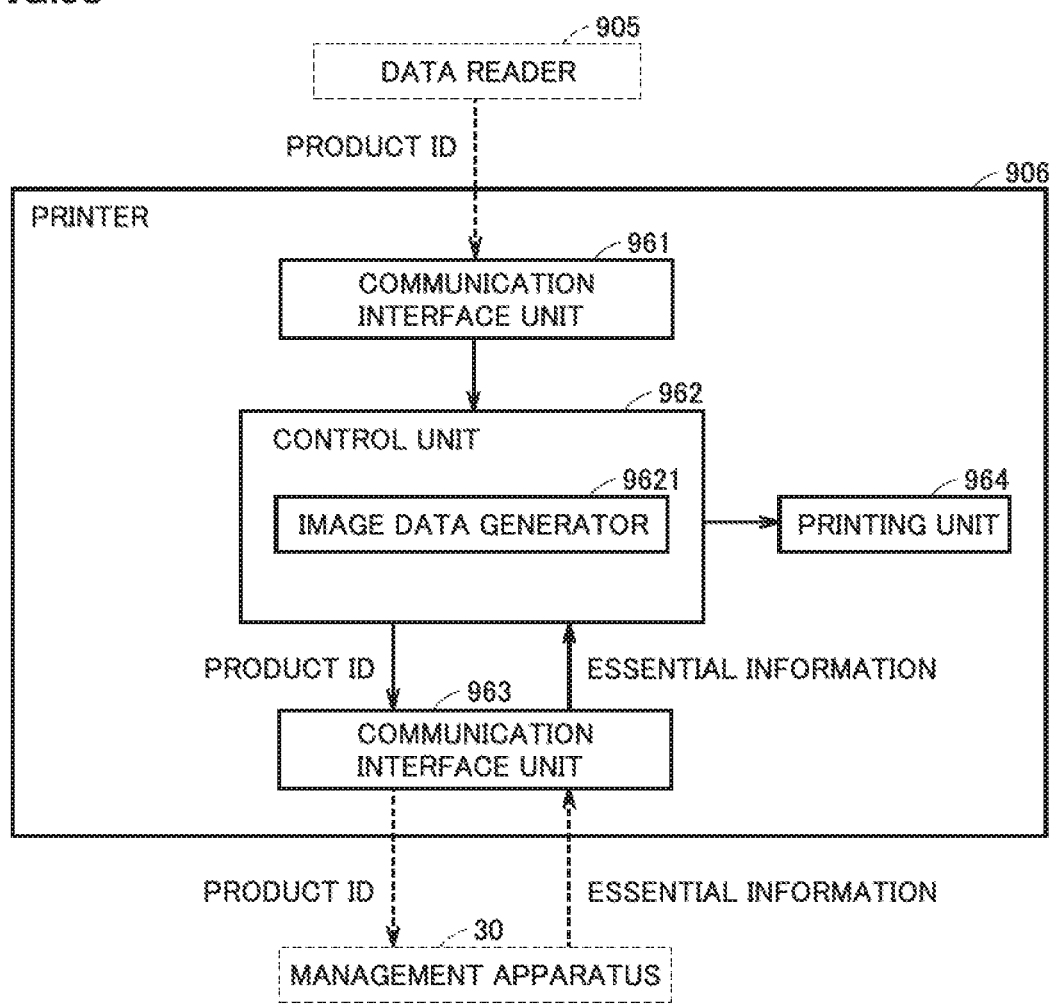
FIG. 38 a diagram for illustrating a functional configuration of a printer.

FIG. 38 a diagram for illustrating a functional configuration of printer 906.

Referring to FIG. 38, printer 906 includes communication interface units 961 and 963 and a control unit 962. Communication interface unit 961 is used for communicating with data reader 905. Communication interface unit 963 is used for communicating with management apparatus 30.

Control unit 962 controls operations of printer 906 as a whole. Printer 906 includes an image data generator 9621.

When control unit 962 receives a product ID through communication interface unit 961, it transmits the product ID to management apparatus 30 through communication interface unit 963. Thereafter, control unit 962 receives essential information associated with the product ID from management apparatus 30.

Image data generator 9621 of control unit 962 generates image data for printing based on the received essential information.

A printing unit 964 receives the image data from image data generator 9621 and prints an image on a seal based on the image data. Seal 981 (see FIG. 36) is thus obtained.

As set forth above, by making use of a specific product ID stored in storage 103 of balloon catheter 10, when used balloon catheter 10 is held over a prescribed apparatus, a label necessary for claiming insurance is output as a seal.

According to such a configuration, in case of emergency or when there are not enough doctors or nurses, labor by them can be lessened.

Data reader 905 preferably reads not only a product ID but also history data 1300 itself. According to such a configuration, printing of essential information and processing for reading history data 1300 can be performed by the same operation. In addition, a doctor can also positively be motivated to read history data 1300 stored in balloon catheter 10.

Modification

Though a configuration in which printer 906 transmits a product ID to management apparatus 30 and receives essential information from management apparatus 30 is described above by way of example, limitation thereto is not intended.

For example, data reader 905 instead of printer 906 may transmit a product ID to management apparatus 30 and receive essential information from management apparatus 30. According to such a configuration, as data reader 905 transmits essential information to printer 906, printer 906 prints essential information on a seal.

Storage 103 of balloon catheter 10 may store in advance not only a product ID but also essential information.

Figure 39:
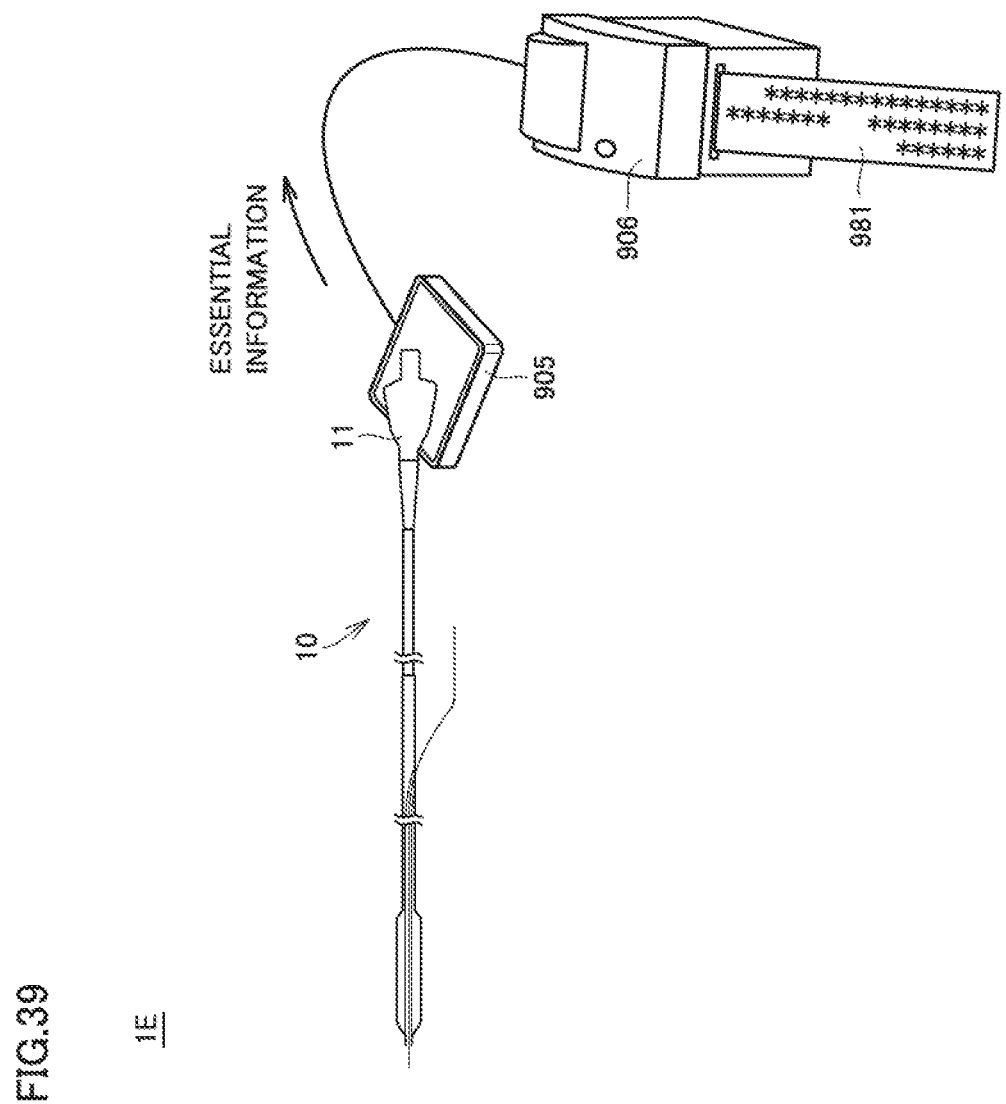
FIG. 39 is a diagram for illustrating a schematic configuration of an information processing system in an example where the balloon catheter stores essential information.

FIG. 39 is a diagram for illustrating a schematic configuration of an information processing system in an example where balloon catheter 10 stores essential information.

Referring to FIG. 39, an information processing system 1E includes balloon catheter 10, printer 906, data reader 905, and management apparatus 30 and server 40 that are not shown.

When hub 11 of balloon catheter 10 comes closer to data reader 905, data reader 905 establishes contactless communication with communication interface unit 104 of hub 11. As a result of contactless communication, data reader 905 reads essential information from storage 103 of hub 11.

Printer 906 receives essential information from data reader 905. Printer 906 prints the essential information on a seal. A doctor or a nurse separates from printer 906, seal 981 on which the essential information has been printed, together with a seal mount (release paper).

According to such a configuration as well, in case of emergency or when there are not enough doctors or nurses, labor performed by them can be lessened as described above.

Though an example in which a seal is employed as a printing medium in information processing systems 1D and 1E is described by way of example, limitation thereto is not intended. Though gluing is necessary, paper may be adopted as the medium.

Though a configuration in which printer 906 and data reader 905 are separate from each other is described above by way of example, limitation thereto is not intended. Printer 906 and data reader 905 may be integrated. Typically, the printer may perform a data reading function in addition to a printing function.

Summary

Information processing system 1D further includes printer 906. Storage 103 of balloon catheter 10 stores in advance a product ID (identification information) thereof. Management apparatus 30 reads the product ID from storage 103 and obtains essential information (prescribed information provided to balloon catheter 10) based on the product ID. Printer 906 obtains the essential information from management apparatus 30 and prints the essential information on a medium (typically, a seal).

Information processing system 1E further includes printer 906 that makes printing on a seal. Storage 103 of balloon catheter 10 stores essential information (prescribed information provided to the balloon catheter) in advance. Balloon catheter 10 further externally outputs the essential information. Printer 906 prints externally output essential information (specifically, information based on the essential information) on a seal. The information based on the essential information may be essential information itself or may be the essential information and information accompanying the essential information. For example, when a prescribed form (an input field) is prepared in advance as accompanying information, essential information is put (entered) into the form, and the essential information is printed altogether with the form, the information based on the essential information refers to information including the form.

Information processing system 1E further includes data reader 905 that establishes contactless communication with balloon catheter 10 and reads the essential information stored in storage 103 of balloon catheter 10. Data reader 905 transmits the essential information read from storage 103 to printer 906.

In information processing systems 1D and 1E, the essential information includes information necessary for claiming insurance. For example, the essential information includes a name of a manufacturer, a lot number, and a catalog number of balloon catheter 10.

(2) Second Example

Processing for updating an electronic medical chart will be described. Specifically, a function to assist input into an electronic medical chart will be described.

Figure 40:
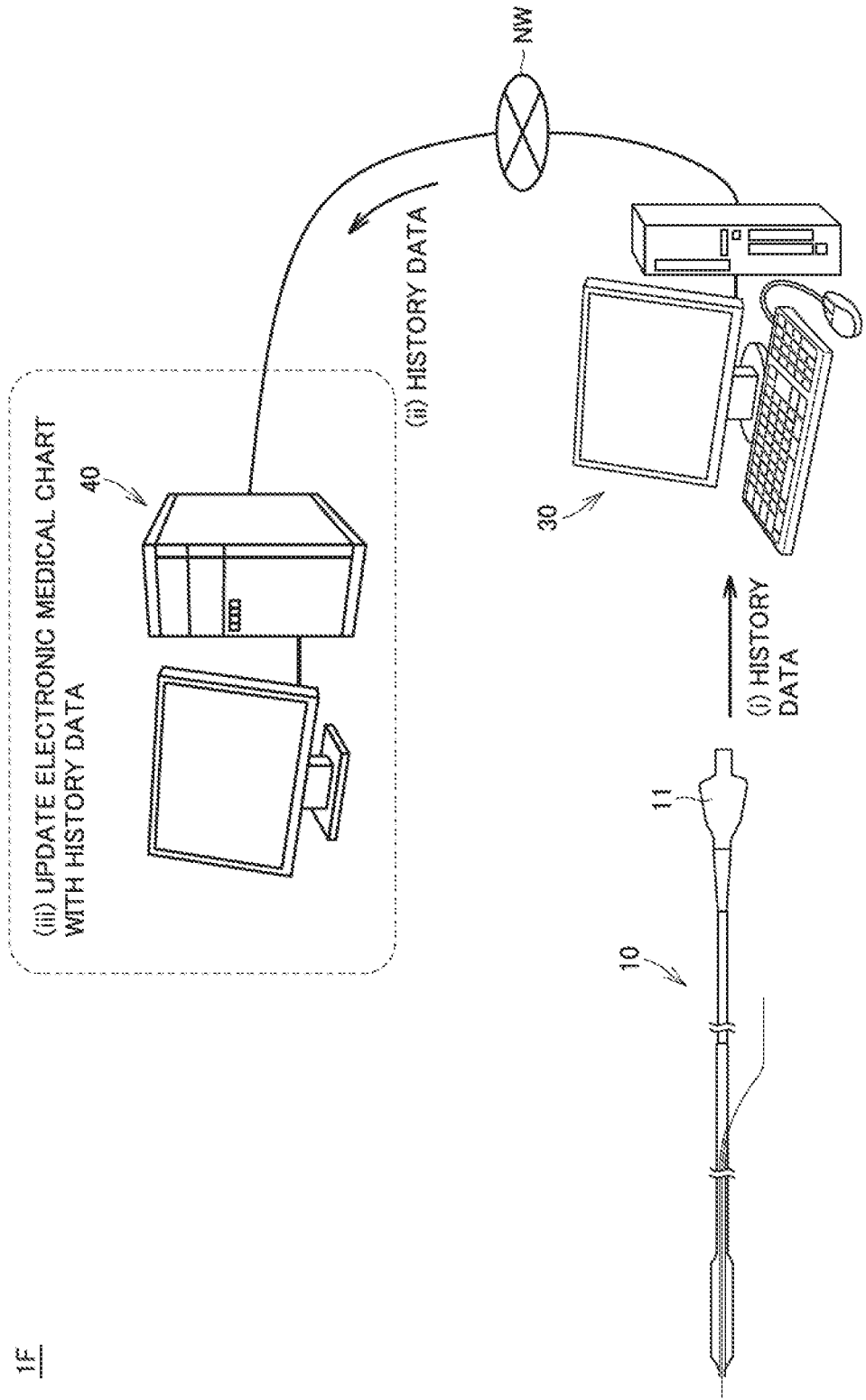
FIG. 40 is a diagram representing an information processing system that updates an electronic medical chart.

FIG. 40 is a diagram representing an information processing system that updates an electronic medical chart. Referring to FIG. 40, an information processing system 1F includes balloon catheter 10, management apparatus 30, and server 40.

As described above, server 40 includes a database including electronic medical charts of a plurality of patients.

As shown in a state (i), management device 30 reads history data (a state value and a result of detection) from collected used balloon catheter 10 and has storage 33 store history data 1300. As shown in a state (ii), management device 30 transmits history data 1300 to server 40 through network NW.

When server 40 receives history data 1300 from management apparatus 30, it updates a corresponding electronic medical chart. Specifically, management apparatus 30 updates an electronic medical chart of a patient who has undergone surgery using balloon catheter 10 with the product ID included in history data 1300. As management apparatus 30 accesses server 40, server 40 can update the electronic medical chart therein. Updated information is typically information written in the electronic medical chart and written also in history data 1300 (redundant information).

In order to perform such processing, server 40 or management apparatus 30 may associate in advance a product ID of balloon catheter 10 to be used with identification information of a patient (a patient ID). When the product ID of balloon catheter 10 has already been stored in the electronic medical chart, the electronic medical chart can be identified by the product ID and hence direct association between the product ID and the patient ID is not required.

According to such a configuration, in coordination with reading of history data 1300 from balloon catheter 10, the electronic medical chart can automatically be updated. Therefore, a work for input into an electronic medical chart by a doctor or the like can be lessened.

According to information processing system 1F, when the electronic medical chart does not store a product ID of balloon catheter 10, the product ID can also be written into the electronic medical chart. According to information processing system 1F, when the product ID of balloon catheter 10 has been stored in the electronic medical chart, a product ID of new balloon catheter 10 can also overwrite the product ID.

Figure 41:
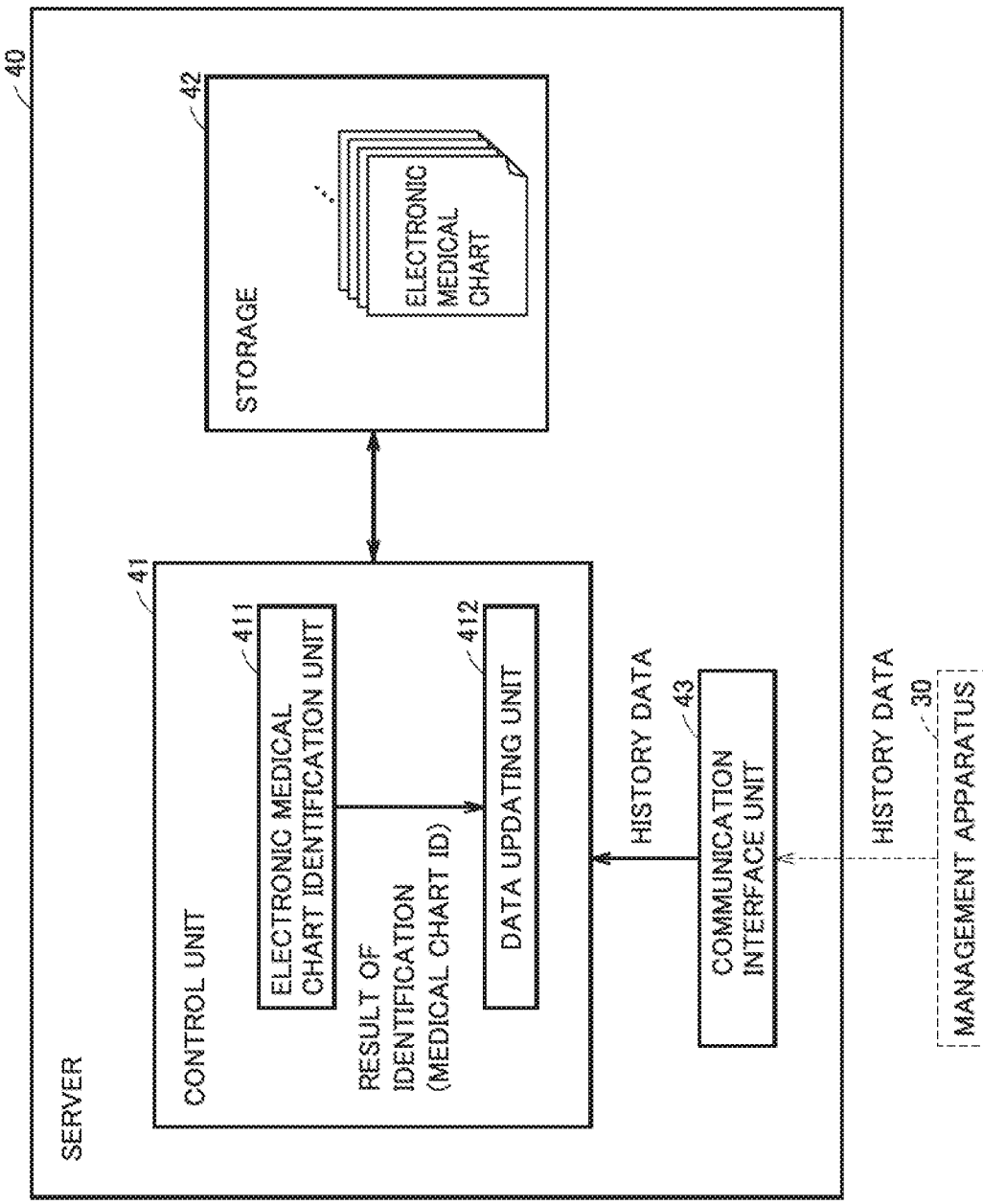
FIG. 41 is a diagram for illustrating a functional configuration of a server in an information processing system.

FIG. 41 is a diagram for illustrating a functional configuration of server 40 in information processing system 1F.

Referring to FIG. 41, server 40 includes a control unit 41, a storage 42, and a communication interface unit 43. Control unit 41 includes an electronic medical chart identification unit 411 and a data updating unit 412.

Communication interface unit 43 receives history data 1300 from management apparatus 30. History data 1300 is sent to control unit 41.

Electronic medical chart identification unit 411 of control unit 41 identifies a patient ID based on a product ID. Electronic medical chart identification unit 411 further identifies an electronic medical chart with the patient ID from among a plurality of electronic medical charts. Data updating unit 412 updates data in the identified electronic medical chart with history data 1300. Specifically, data updating unit 412 extracts data corresponding to an item in the electronic medical chart from history data 1300 and writes extracted data into the item.

Summary

Information processing system 1F includes server 40 that stores an electronic medical chart of a patient who has undergone surgery using balloon catheter 10. Management apparatus 30 transmits history data 1300 (a result of detection) to server 40. Server 40 writes the history data into the electronic medical chart.

Server 40 extracts data corresponding to an item in the electronic medical chart from history data 1300. Server 40 writes the extracted data into the item.

Management apparatus 30 obtains product ID identification information from balloon catheter 10 and transmits the obtained product ID to server 40. Server 40 writes the product ID into the electronic medical chart.

c4. Clinical Research Assistance

A plurality of pieces of history data 1300 accumulated in storage 33 of management apparatus 30 can be provided to a doctor as assistance for a method of using a balloon catheter or assistance for clinical research. In particular, provision of electronic medical charts and history data 1300 in association with each other to a doctor for each patient is extremely useful for assistance for the method of use and assistance for clinical research.

Since magnitude of a pressure or the number of times of inflation of balloon catheter 10 is different for each type of a product even though the doctor is the same, provision of history data 1300 is useful for each doctor.

D. Improvement in Product

History data 1300 may be information important also for a manufacturer of balloon catheter 10.

A manufacturer can improve balloon catheter 10 by using history data 1300 as a guide. In particular, there are various types of balloon catheters. Therefore, by managing and analyzing history data 1300 for each type, improvement for each type can be made. History data 1300 can also be used for newly developing a balloon catheter.

E. Individual Management

Individual management of balloon catheter 10 will be described.

In a process for treating used balloon catheter 10 as a reuse product (reclamation product), change of a product ID from an old ID to a new ID may be expected.

By changing a product ID as such, mix-up of products (balloon catheters) or loss of an ID may occur. Loss of the ID means that it becomes basically unclear of which product type a product is.

A checking mechanism for preventing occurrence of such a situation will be described below.

Figure 42:
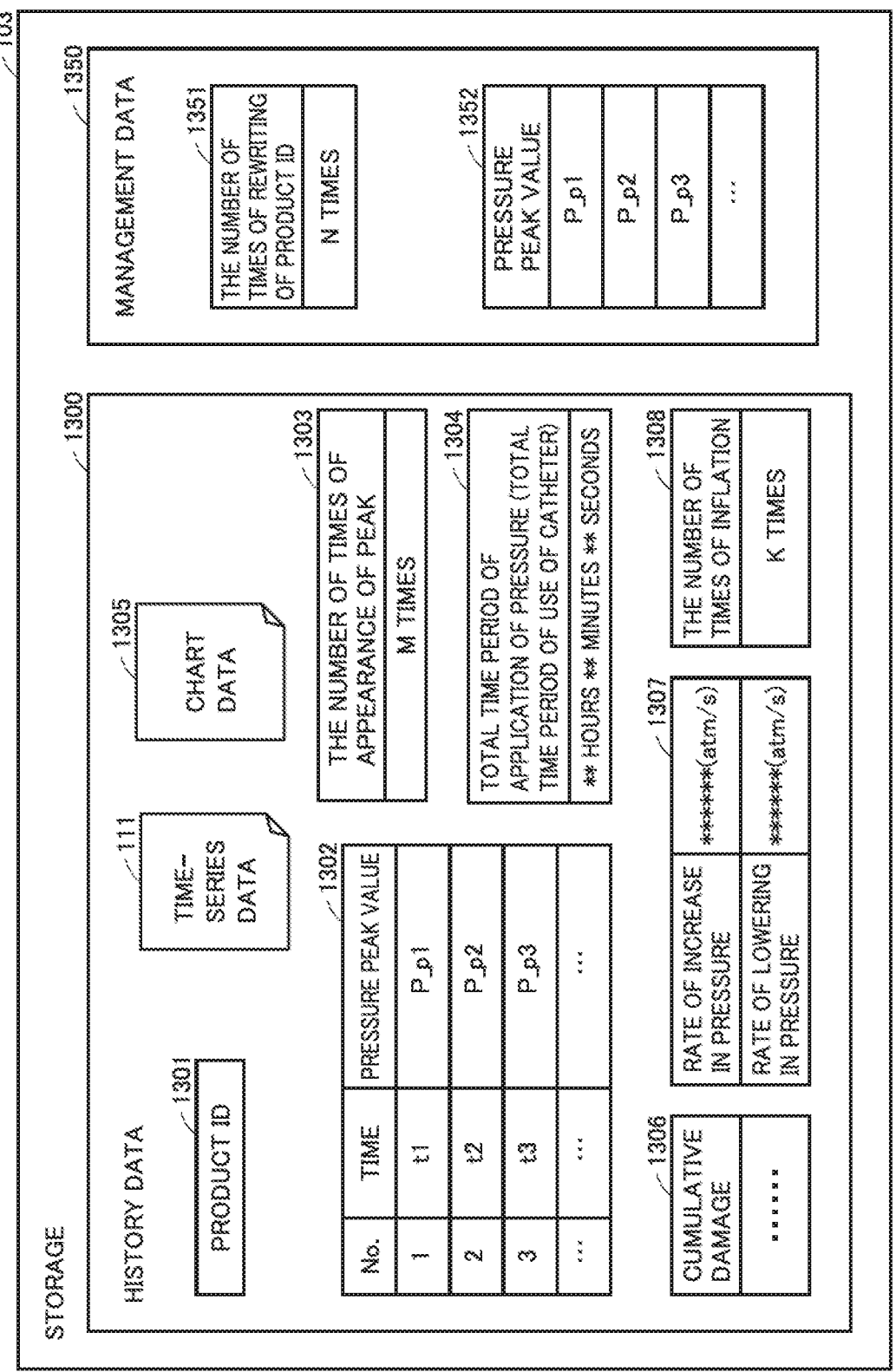
FIG. 42 is a diagram for illustrating a checking mechanism for individual management.

FIG. 42 is a diagram for illustrating a checking mechanism for individual management.

Referring to FIG. 42, storage 103 of balloon catheter 10 stores management data 1350 in addition to history data 1300. Management data 1350 includes data 1351 representing the number of times of rewriting of a product ID and data 1352 representing a peak value of a pressure in each time of detection.

Management data 1350 is protected so as not to be erased even though processing for reuse is performed, which is a difference from history data 1300.

Management apparatus 30 reads management data 1350 together with history data 1300 from balloon catheter 10, and has storage 33 store management data 1350 in association, for example, with the product ID in history data 1300. When ID loss occurs, processing below is performed.

Initially, management data 1350 is read from balloon catheter 10. Then, read management data 1350 is compared with a plurality of pieces of management data (management data obtained from a plurality of balloon catheters 10) accumulated in management apparatus 30. For example, management apparatus 30 makes such comparison. When management apparatus 30 finds management data that matches with read management data 1350, for example, it has display 308 show the product ID associated with the management data. According to such processing, ID loss can be addressed. When mix-up of products occurs as well, a product can accurately be identified through the processing above.

Summary

Storage 103 of balloon catheter 10 stores a product ID of balloon catheter 10. The product ID is rewritable by management apparatus 30. Balloon catheter 10 has storage 103 store the number of times of rewriting of the product ID.

A result of detection includes a plurality of types of data (each piece of data included in history data 1300). Even though balloon catheter 10 is reused, balloon catheter 10 keeps storage of specific data among the plurality of types of data in storage 103. Typically, storage 103 keeps storage as specific data, a peak value equal to or larger than a predetermined threshold value, among peak values of the pressure.

F. Management by Supply Chain

Management of inventory of balloon catheter 10 and management of a production schedule in a supply chain will be described. Reuse of balloon catheter 10 is not essential in the description below.

Figure 43:
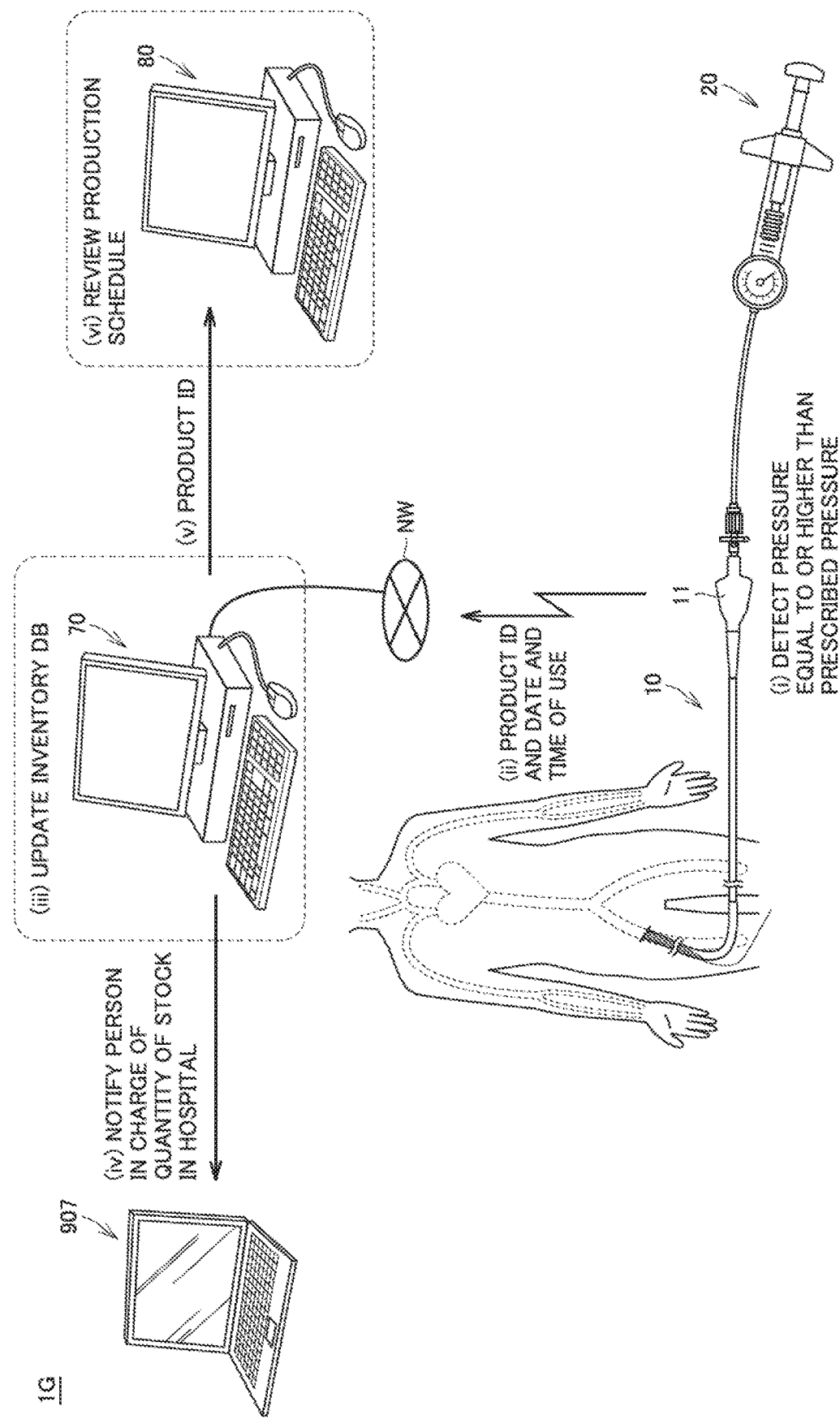
FIG. 43 is a diagram representing an information processing system that manages the balloon catheter in a distributor.

FIG. 43 is a diagram representing an information processing system that manages balloon catheter 10 in a distributor.

Referring to FIG. 43, an information processing system 1G includes balloon catheter 10, inflation device 20, a server 70, a terminal apparatus 907, and a server 80.

Management in the supply chain will be described below, for each of management of a production schedule by a manufacturer of balloon catheter 10 and management of inventory by a distributor that purchases balloon catheters from the manufacturer and sells balloon catheters to a hospital. Initially, management of inventory in the distributor will be described and then management of the production schedule in the manufacturer will be described. The distributor is not limited to a single company.

(1) Management of Inventory by Distributor

Server 70 is equipment that manages inventory of balloon catheters 10. Server 70 stores a product ID of balloon catheter 10 in association with information representing a hospital to which balloon catheter 10 has been delivered. A type of balloon catheter 10 is associated with the product ID.

Server 70 is made use of by the distributor of balloon catheter 10. Server 70 may be a server owned by the distributor or an external server.

Terminal apparatus 907 is equipment made use of by a person in charge who delivers balloon catheters 10 to a hospital. Terminal apparatus 907 may be a smartphone, a tablet terminal, or a lap-top or desk-top personal computer. Terminal apparatus 907 may be mobile equipment or stationary equipment.

A person in charge can access server 70 by performing a log-in operation on terminal apparatus 907. Terminal apparatus 907 can receive a notification which will be described later from server 70.

When detector 110 of balloon catheter 10 detects a pressure equal to or higher than a prescribed value as shown in a state (i), it transmits a predetermined signal to server 70 through network NW as shown in a state (ii). The predetermined signal typically includes a product ID of balloon catheter 10. The predetermined signal preferably includes date and time of use (that is, date and time of detection of a pressure equal to or higher than a prescribed value).

As server 70 receives the product ID from balloon catheter 10, it can sense use of balloon catheter 10 of a specific type. In particular, since the product ID is associated with information representing a hospital to which balloon catheter 10 has been delivered, server 70 can also determine in which hospital balloon catheter 10 has been used.

When server 70 identifies a type of balloon catheter 10 and a hospital where balloon catheter 10 has been used, it updates an inventory database (which is also referred to as an "inventory DB" below) used for management of inventory as shown in a state (iii). Specifically, server 70 decreases, in the inventory DB, the number of stocks of the type in that hospital.

When a quantity of stock is equal to or smaller than a threshold value set in advance, server 70 transmits information on the quantity of stock to terminal apparatus 907 (specifically, a person in charge of the hospital) as shown in a state (iv). In this case, terminal apparatus 907 shows information on the quantity of stock on a display based on reception of the information. The information on the quantity of stock may be transmitted via an electronic mail or given by pop-up representation on the display.

According to such a configuration, as the person in charge promptly delivers new products to the hospital where balloon catheters 10 have been used, occurrence of a situation that the hospital is short of balloon catheters 10 can be avoided.

Though a configuration in which a notification is given to terminal apparatus 907 when the quantity of stock is equal to or smaller than a threshold value set in advance is described above by way of example, limitation thereto is not intended. Each time balloon catheter 10 is used, a user of terminal apparatus 907 (specifically, a person in charge of the hospital) may be notified of use thereof, together with the quantity of stock.

Figure 44:
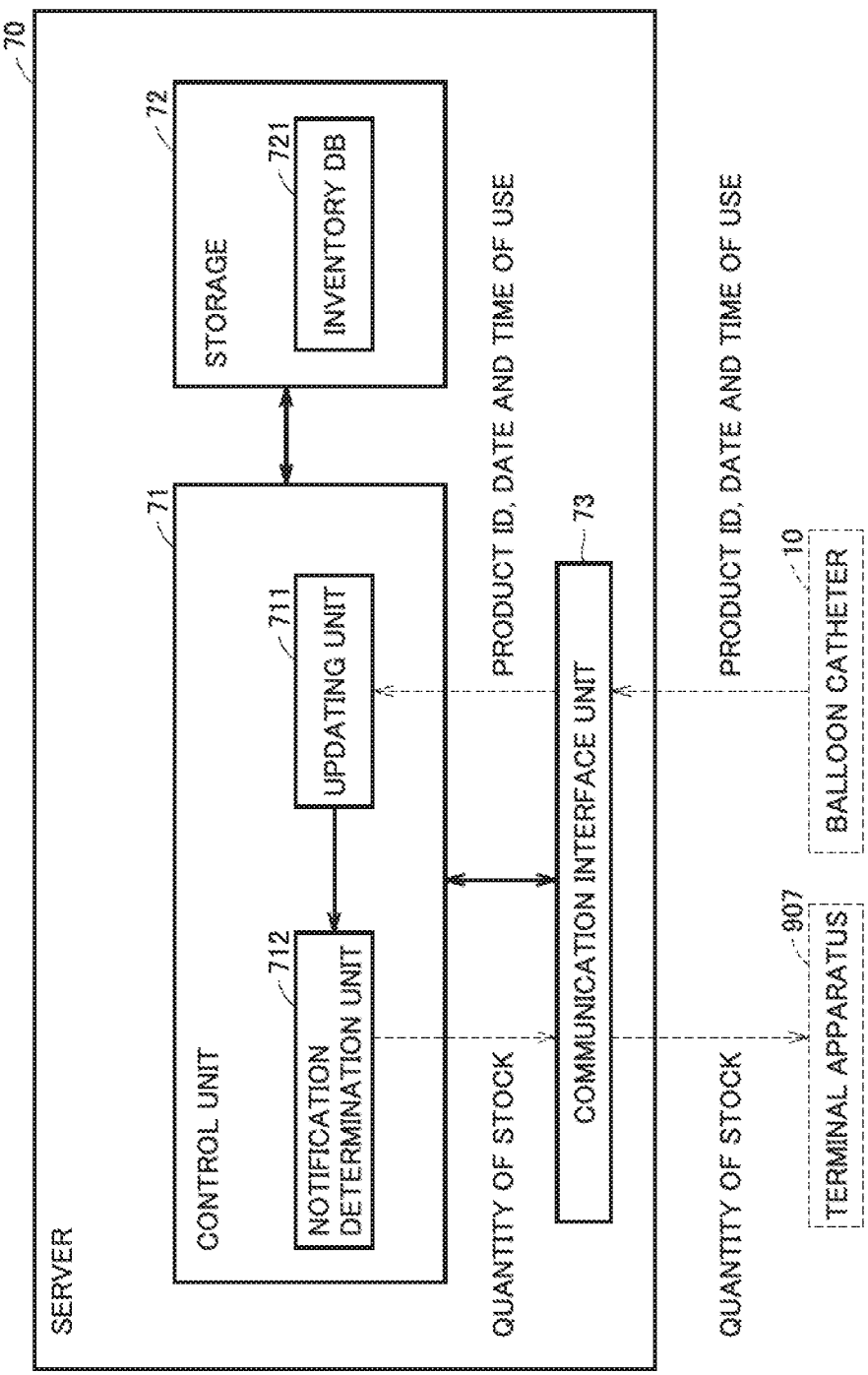
FIG. 44 is a diagram for illustrating a functional configuration of a server.

FIG. 44 is a diagram for illustrating a functional configuration of server 70.

Referring to FIG. 44, server 70 includes a control unit 71, a storage 72, and a communication interface unit 73.

Control unit 71 includes an updating unit 711 and a notification determination unit 712. Storage 72 stores an inventory DB 721. Inventory DB 721 records at least a quantity of stock of balloon catheters 10 for each type of balloon catheter 10.

Control unit 71 obtains a product ID and information on date and time of use from a plurality of balloon catheters 10 through communication interface unit 73. Updating unit 711 updates inventory DB 721 based on the product ID and information on date and time of use. Updating unit 711 sends the updated quantity of stock to notification determination unit 712.

Notification determination unit 712 compares the updated quantity of stock with a threshold value, and when the quantity of stock is equal to or smaller than the threshold value, it notifies terminal apparatus 907 of the quantity of stock through communication interface unit 73. Occurrence of a situation that the hospital is short of balloon catheters 10 can thus be avoided as described above.

(2) Management of Production Schedule in Manufacturer

Referring again to FIG. 43, server 80 is equipment that manages inventory of balloon catheters 10 in a manufacturer. Server 80 also functions as equipment that manages production of balloon catheters 10. Server 80 receives a product ID of balloon catheter 10 from server 70 as shown in a state (v), based on acquisition by server 70 of the product ID from balloon catheter 10.

Server 80 is made use of by the manufacturer of balloon catheter 10. Server 80 may be a server owned by the manufacturer or an external server.

Each time server 80 receives the product ID from server 70 of the distributor, it can determine which type of balloon catheter 10 has been used.

Therefore, server 80 can sense in real time, a state of use of balloon catheter 10. Therefore, the schedule of production of balloon catheters 10 can also be changed each time.

Figure 45:
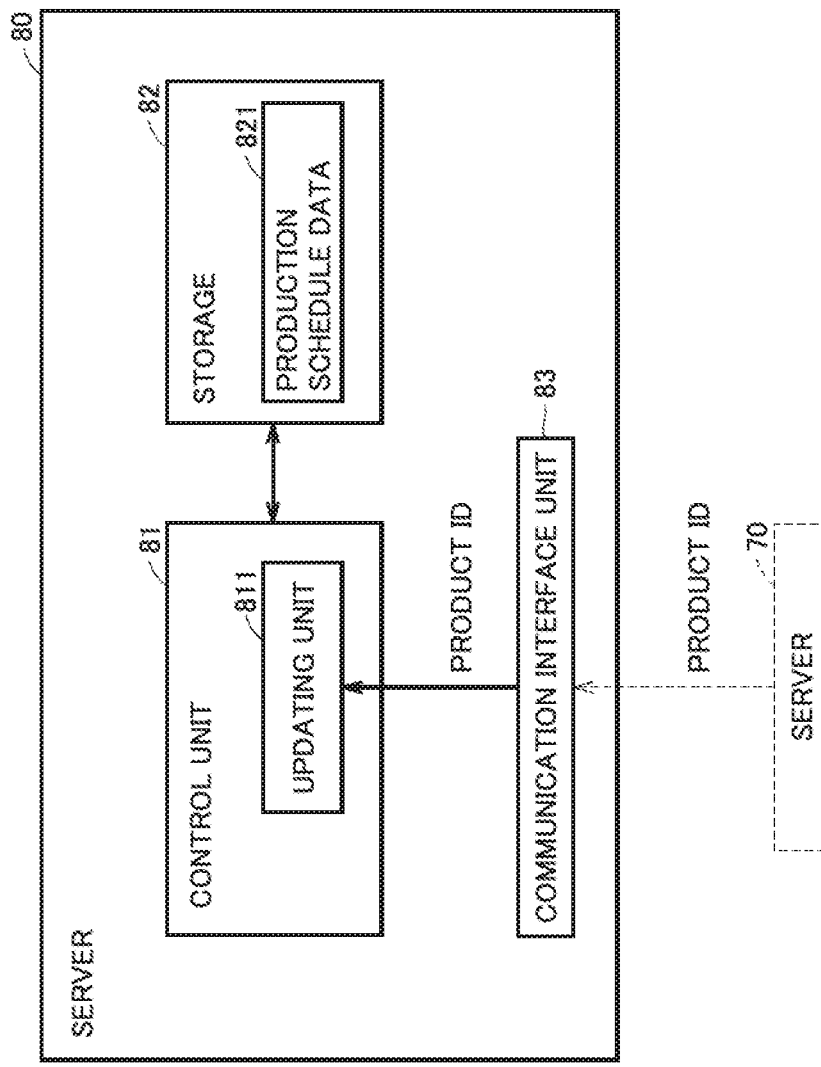
FIG. 45 is a diagram for illustrating a functional configuration of a server.

FIG. 45 is a diagram for illustrating a functional configuration of server 80.

Referring to FIG. 45, server 80 includes a control unit 81, a storage 82, and a communication interface unit 83.

Control unit 81 includes an updating unit 811. Storage 82 stores production schedule data 821.

Production schedule data 821 records a schedule of production of balloon catheters 10 for each type of balloon catheter 10. For example, production schedule data 821 records a production schedule for each month or each year.

Control unit 81 obtains a product ID from server 70 through communication interface unit 83. Updating unit 811 modifies the production schedule based on the product ID received from server 70 (see a state (vi) in FIG. 43). Typically, updating unit 811 modifies the production schedule based on the number of times of reception of a signal per unit period. Specifically, updating unit 811 modifies the production schedule at prescribed timing based on change in quantity of stock in inventory DB 721.

The production schedule is modified for each type of balloon catheter 10 based on the product ID. Prescribed timing may come every prescribed period (for example, every month) or when the total quantity of stock decreases by a threshold value or more.

According to such a configuration, the manufacturer can manufacture balloon catheters 10 in accordance with a highly accurate production schedule.

(3) Modification

Though an example in which a product ID is associated in advance in server 70 with information representing a hospital to which balloon catheter 10 has been delivered is described above by way of example, limitation thereto is not intended.

For example, balloon catheter 10 may be provided with a function to obtain position information thereof (typically, a GPS function). When balloon catheter 10 detects a pressure equal to or higher than a prescribed value, it transmits a predetermined signal including position information at the time of detection of the pressure to server 70. Server 70 identifies a hospital based on the position information.

According to such a configuration as well, server 70 can determine which type of balloon catheter 10 has been used and in which hospital balloon catheter 10 has been used.

Though an example in which the manufacturer and the distributor are different from each other is described above by way of example, a single server may manage inventory and production when the manufacturer directly delivers balloon catheters 10 to a hospital.

(4) Summary

Information processing system 1G further includes server 70 that manages a quantity of stock of balloon catheter 10 in a hospital. When balloon catheter 10 detects a pressure equal to or higher than a predetermined threshold value, it transmits a predetermined signal to server 70. Server 70 determines that the balloon catheter has been used, based on reception of the predetermined signal.

When a quantity of stock of balloon catheter 10 in the hospital is equal to or smaller than a prescribed quantity (threshold value), server 70 transmits information on the quantity of stock to terminal apparatus 907 (terminal apparatus 907 on which a person in charge of the distributor has performed the log-in operation). Terminal apparatus 907 shows information on the quantity of stock.

Information processing system 1G further includes server 80 that manages the schedule of production of balloon catheters 10 in the manufacturer of balloon catheter 10. The predetermined signal includes a product ID of balloon catheter 10 where a pressure equal to or higher than a prescribed pressure (predetermined threshold value) has been detected. Server 80 receives the product ID from server 70 and updates the production schedule in the manufacturer of balloon catheter 10 based on the product ID.

G. Management of Reuse Product by Maintenance Service Provider

Management of inventory described above may be applied to management of inventory in a maintenance service provider. Specifically, server 70 may be regarded as an apparatus that is made use of by a maintenance service provider of balloon catheter 10 and terminal apparatus 907 may be regarded as equipment made use of by a person in charge who delivers recycled balloon catheters 10 to a hospital.

According to such a configuration, as a person in charge in the maintenance service provider promptly delivers newly recycled products to a hospital where balloon catheter 10 has been used, occurrence of a situation that the hospital is short of balloon catheter 10 can be avoided.

H. Modification (1) Though a configuration in which balloon catheter 10 detects a state value (history data) is described above by way of example, limitation thereto is not intended.

Various types of computation processing described above by data processing unit 112 (see FIG. 13) of detector 110 may be performed, for example, by an apparatus such as management apparatus 30.

(2) A configuration including balloon catheter 10 including detector 110 that detects a pressure in pipe path 190 and printer 906 that prints essential information (information essential for claiming insurance) (see FIGS. 36 and 39) is described above.

When attention is paid only to printing of essential information, however, balloon catheter 10 should only store a product ID or essential information, and the balloon catheter does not have to include detector 110.

Such an information processing system can be concluded to be configured as below. The information processing system includes a balloon catheter and a printer that makes printing on a seal. The balloon catheter has a memory (storage 103) store in advance prescribed information (essential information) provided thereto and further externally outputs the prescribed information. Printer 906 prints the externally output prescribed information on a seal.

(3) Description is given above with attention being paid to the balloon catheter. A system configuration for addressing an infectious disease (a system configuration that determines whether or not balloon catheter 10 has been used for a patient with an infectious disease and a system configuration that inspects for a substance remaining in used balloon catheter 10 that causes an infectious disease), however, can also be applied to a catheter other than the balloon catheter.

A method for recycling a used balloon catheter, a balloon catheter, and an information processing system are described above for each section of "A. Acquisition of Data," "B. Recycling of Balloon Catheter," "C. Medical Assistance," "D. Improvement in Product," "E. Individual Management," "F. Management by Supply Chain," "G. Management of Reuse Product by Maintenance Service Provider," and "H. Modification." These contents can be combined as appropriate. Processing and configurations described above can be combined as appropriate unless particularly discouraged to do so.

I. Additional Aspects

[1]: A method for recycling a used balloon catheter includes:
accepting a used balloon catheter, the balloon catheter including a detector that detects a state value including at least a pressure generated in a pipe path formed within the balloon catheter and a storage that stores a result of detection by the detector; and
determining at least one of reusability of the used balloon catheter and a method of recycling the used balloon catheter based on the result of detection stored in the storage of the used balloon catheter.

[1A]: A method preferably includes reading a result of detection stored in a storage of a used balloon catheter and determining at least one of reusability of the used balloon catheter and a method of recycling the used balloon catheter based on the result of detection.

[1-1]: The method described in [1], wherein
the result of detection includes a peak value of the pressure, and
in the determining reusability of the balloon catheter, when the peak value exceeds a predetermined threshold value, the balloon catheter is determined as non-reusable.

[1-2]: The method described in [1], wherein
the result of detection includes number information that represents the number of peak values equal to or larger than a predetermined threshold value, of peak values of the pressure, and
in the determining reusability of the balloon catheter, when the number of peak values exceeds the predetermined threshold value, the balloon catheter is determined as non-reusable.

[1-3]: The method described in [1], wherein
the result of detection includes a calculation value obtained by integrating the pressure with respect to a time period of pressure application, and
in the determining reusability of the balloon catheter, when the calculation value exceeds a predetermined threshold value, the balloon catheter is determined as non-reusable.

[1-4]: The method described in [1], wherein
the result of detection includes rate information that represents a rate of lowering in pressure, and
in the determining reusability of the balloon catheter, when the rate of lowering exceeds a predetermined threshold value, the balloon catheter is determined as non-reusable.

[1-5]: The method described in any one of [1], [1-1], [1-2], [1-3], and [1-4], wherein
the storage further includes expiration information on expiration data that represents expiration date of use of the balloon catheter, and
the method further includes
reading the expiration information from the storage, and
determining reusability of the balloon catheter based on the expiration information.

[2]: The method described in [1] further includes inspecting for a substance remaining in the used balloon catheter that causes an infectious disease.

[3]: The method described in [1] or [2], wherein the storage can store use history information that represents use of the balloon catheter for a patient with an infectious disease, and
the method further includes
reading the use history information from the storage, and
determining reusability of the balloon catheter based on the use history information.

[4]: The method described in any one of [1], [2], and [3] further includes determining whether or not the balloon catheter can be shipped based on a result of a pressure test of the balloon catheter.

[5]: The method described in any one of [1], [2], [3], and [4] further includes determining whether or not the balloon catheter can be shipped based on a result of visual inspection of the balloon catheter.

[5-1]: The method described in any one of [1], [1-1] to [1-4], [2], and [3] further includes determining whether or not an outer geometry of a balloon of the balloon catheter is within a prescribed range at the time of application of a reference pressure and determining whether or not the balloon catheter can be shipped based on a result of determination.

[5-2]: The method described in any one of [1], [1-1] to [1-4], [2], [3], [5], and [5-1], wherein
in the determining a method of recycling the balloon catheter, at least one of the number of times of washing and a time period of washing of the balloon catheter is determined.

[6]: The method according to any one of [1], [1-1] to [1-4], [2], [3], [5], [5-1], and [5-2], wherein
the storage further stores identification information of the balloon catheter, and the method further includes
reading the identification information from the storage, and
associating the result of detection and the identification information with each other.

[7]: A balloon catheter with a pipe path, the balloon catheter includes:
a detector that detects a state value including at least a pressure generated in the pipe path;
a storage that stores a result of detection by the detector; and
an interface unit for output of a result of detection stored in the storage.

[7-1]: The balloon catheter described in [7], wherein
the result of detection includes at least one of a peak value of the pressure, number information that represents the number of peak values equal to or larger than a predetermined threshold value, of peak values of the pressure, a calculation value obtained by integrating the pressure with respect to a time period of pressure application, rate information that represents a rate of lowering in pressure, and the time period of pressure application.

[7-2]: The balloon catheter described in [7] or [7-1], wherein
the interface unit externally outputs the result of detection through wireless communication.

[8]: The balloon catheter described in [7] further includes
an estimator that estimates whether or not fluid contained in the pipe path leaks to the outside of the pipe path based on change in pressure, and
a notification unit that gives a predetermined notification based on estimation of occurrence of leakage by the estimator.

[9]: The balloon catheter described in [7] or [8] further includes a notification unit that gives a notification about a state of pressure application in the pipe path.

[9-1]: The balloon catheter described in any one of [7], [7-1], and [7-2] further includes a notification unit that gives a predetermined notification when the pressure exceeds a rated burst pressure of a balloon in the balloon catheter.

[9-2]: The balloon catheter described in [9], wherein
the notification unit gives a predetermined notification as a notification of the state of pressure application, when the pressure exceeds a rated burst pressure of a balloon in the balloon catheter.

[9-3]: The balloon catheter described in any one of [7], [7-1], and [7-2] further includes a notification unit that gives an aural notification about a value of the pressure, on condition that the pressure is applied to the pipe path.

[9-4]: The balloon catheter described in [9], wherein
the notification unit gives an aural notification about a value of the pressure, as a notification about the state of the pressure application, on condition that a pressure is applied to the pipe path.

[9-5]: The balloon catheter described in any one of [7], [7-1], and [7-2] further includes a notification unit that gives a notification about time elapsed since the pressure attains to a constant pressure, on condition that the pressure is applied to the pipe path and attains to the constant pressure.

[9-6]: The balloon catheter described in [9], wherein
the notification unit gives a notification about time elapsed since the pressure attained to a constant pressure, as a notification about the state of the pressure application, on condition that the pressure is applied to the pipe path and attains to the constant pressure.

[10]: An information processing system includes:
a balloon catheter including a pipe path; and
an information processing apparatus, wherein
the balloon catheter includes a memory, detects a state value including at least a pressure generated in the pipe path, stores a result of detection in the memory, and outputs the stored result of detection to the outside, and
the information processing apparatus receives the result of detection output to the outside.

[11]: The information processing system described in [10], wherein
the information processing apparatus receives the result of detection from each of a plurality of balloon catheters, determines a pressure application condition of the balloon catheter for a patient who will undergo surgery, based on electronic medical charts of a plurality of patients and the result of detection, and gives a notification about the determined pressure application condition.

[11-1]: The information processing system described in [11], wherein
the information processing apparatus notifies the balloon catheter to be used for the patient who will undergo surgery of the determined pressure application condition, and
the balloon catheter shows the pressure application condition.

[11-2]: The information processing system described in [11] further includes a server that stores the electronic medical charts and a terminal apparatus connected to the server, wherein
the information processing apparatus notifies the terminal apparatus of the determined pressure application condition with the server being interposed, and
the terminal apparatus shows the pressure application condition.

[11-3]: The information processing system described in [11] further includes an inflation device that injects liquid into the balloon catheter, wherein
the information processing apparatus notifies the inflation device of the determined pressure application condition, and
the inflation device injects the liquid into the balloon catheter such that the pressure in the pipe path of the balloon catheter satisfies the determined pressure application condition.

[11-4]: The information processing system described in [10] further includes a printer, wherein the memory stores in advance identification information of the balloon catheter, the information processing apparatus reads the identification information from the memory and obtains prescribed information provided to the balloon catheter based on the identification information, and the printer obtains the prescribed information from the information processing apparatus and prints the prescribed information on a medium.

[12]: The information processing system described in [10], wherein the memory stores in advance prescribed information provided to the balloon catheter.

[13]: The information processing system described in [12] further includes a printer, wherein the balloon catheter further outputs the prescribed information to the outside, and the printer prints on a medium, information based on the prescribed information output to the outside.

[14]: The information processing system described in [13] further includes a data reader that reads the prescribed information stored in the memory by establishing contactless communication with the balloon catheter, wherein the data reader transmits the prescribed information to the printer.

[14-1]: The information processing system described in any one of [11-4], [12], [13], and [14], wherein the prescribed information includes information necessary for claiming insurance.

[15]: The information processing system described in [12] further includes a server that stores an electronic medical chart of a patient who has undergone surgery using the balloon catheter, wherein the information processing apparatus obtains the prescribed information from the balloon catheter and transmits the result of detection and the prescribed information to the server, and the server writes the result of detection and the prescribed information in the electronic medical chart.

[16]: The information processing system described in [15], wherein the server extracts data corresponding to an item in the electronic medical chart from the result of detection and writes the extracted data in the item.

[17]: The information processing system described in [10], wherein the memory stores identification information of the balloon catheter, the identification information is rewritable by the information processing apparatus, and the balloon catheter stores the number of times of rewriting of the identification information in the memory.

[18]: The information processing system described in [17], wherein the result of detection includes a plurality of types of data, and even though the balloon catheter is reused, the balloon catheter keeps storage of specific data among the plurality of types of data in the memory.

[19]: The information processing system described in [18], wherein the specific data is a peak value equal to or larger than a predetermined threshold value, among peak values of the pressure.

[20]: The information processing system described in [10] further includes a first server that manages a quantity of stock of the balloon catheter in a hospital, wherein when the balloon catheter detects the pressure equal to or higher than a predetermined threshold value, the balloon catheter transmits a predetermined signal to the first server, and the first server determines that the balloon catheter has been used based on reception of the predetermined signal.

[21]: The information processing system described in [20], wherein when the quantity of stock of the balloon catheter in the hospital is equal to or smaller than a prescribed quantity, the first server transmits information on the quantity of stock to a predetermined terminal apparatus, and the terminal apparatus shows the information on the quantity of stock.

[22]: The information processing system described in [20] or [21] further includes a second server that manages a schedule of production of the balloon catheter in a manufacturer that manufactures the balloon catheter, wherein the predetermined signal includes identification information of the balloon catheter where a pressure equal to or higher than the predetermined threshold value has been detected, and the second server receives the identification information from the first server and updates the schedule of production in the manufacturer of the balloon catheter based on the identification information.

The embodiments disclosed herein are illustrative and not restricted only to the contents above. The scope of the present invention is defined by the terms of the claims and is intended to include any modifications within the scope and meaning equivalent to the terms of the claims.

REFERENCE SIGNS LIST 1, 1A, 1B, 1C, 1D, 1E, 1F, 1G information processing system; 10 balloon catheter; 11, 11A, 11B, 11C, 11D, 11E, 11F, 11G, 11H, 11I, 11J hub; 12 strain relief; 13 catheter shaft; 14 balloon; 15 guide wire port; 16 guide wire; 17 balloon inflation port; 20, 20A inflation device; 21 syringe; 22 piston; 23 locking lever; 24 gauge; 25 connection tube; 26 T-shaped stopcock; 28, 105 battery; 30 management apparatus; 31, 43, 73, 83, 104, 211, 961, 963 communication interface unit; 32, 41, 71, 81, 212, 962 control unit; 33, 42, 72, 82, 103 storage; 34 input operation unit; 35 display unit; 40, 70, 80 server; 50 biosensor; 60, 907 terminal apparatus; 100 housing; 101, 301 processor; 102 pressure sensor; 102A piezoelectric element; 104A antenna; 105A storage battery; 106 solar panel; 108 port; 109 device; 110 detector; 111 time-series data; 112 data processing unit; 131 inner pipe; 132 outer pipe; 140 notification unit; 141 audio output unit; 142 light emitter; 143, 308 display; 150 estimator; 170 end; 175 button; 180 switch; 181 movable member; 190 pipe path; 213 pressure regulation mechanism; 214 operation button; 302 ROM; 303 RAM; 305 communication IF unit; 306 operation key; 307 power supply circuit; 321 association unit; 322 analysis processing unit; 323 ID acceptance unit; 324 condition determination unit; 330 database; 411 electronic medical chart identification unit; 412 data updating unit; 711, 811 updating unit; 712 notification determination unit; 721 inventory DB; 821 production schedule data; 901, 904 data reader; 902, 903, 904A cable; 906 printer; 964 printing unit; 980 paper; 981, 982 seal; 990 patient; 1300 history data; 1302 peak value data; 1303, 1304, 1306, 1307, 1308, 1351, 1352 data; 1305 chart data; 1350 management data; 9031 connector; 9621 image data generator; NW network

The invention claimed is:

1. A method for recycling a used balloon catheter, the method comprising:
   accepting a used balloon catheter, the balloon catheter including a detector that detects a state value including at least a pressure generated in a pipe path formed within the balloon catheter and a storage that stores a result of detection of the state value by the detector; and
   determining at least one of a time period of washing and the number of times of washing of the balloon catheter necessary for recycling the used balloon catheter based on the result of detection stored in the storage of the used balloon catheter.

2. The method according to claim 1, further comprising inspecting a substance remaining in the used balloon catheter that causes an infectious disease.

3. The method according to claim 1, wherein
   the storage is configured to store use history information that represents use of the balloon catheter for a patient with an infectious disease, and
   the method further comprises:
      reading the use history information from the storage; and
      determining the time period of washing and the number of times of washing of the balloon catheter based on the use history information.

4. The method according to claim 1, further comprising:
   conducting a pressure test of the balloon catheter; and
   determining the time period of washing and the number of times of washing of the balloon catheter based on a result of the pressure test of the balloon catheter.

5. The method according to claim 1, further comprising:
   conducting a visual inspection of the balloon catheter; and
   determining the time period of washing and the number of times of washing of the balloon catheter based on a result of the visual inspection of the balloon catheter.

6. The method according to claim 1, wherein
   the storage further stores identification information of the balloon catheter, and
   the method further comprises:
      reading the identification information from the storage; and
      associating the result of detection and the identification information with each other.

7. An information processing system comprising:
   a balloon catheter including a pipe path, a pressure sensor, a first processor, a first memory, and a first communication interface; and
   an information processing apparatus including a second processor, a second memory, and a second communication interface, wherein
   the balloon catheter is configured such that the pressure sensor detects a state value including at least a pressure generated in the pipe path and the first processor stores a result of detection of the state value by the pressure sensor in the first memory,
   the information processing apparatus is configured such that the second processor transmits a prescribed request signal to the balloon catheter through the second communication interface,
   the first processor is further configured to transmit the result of detection stored in the first memory to the information processing apparatus through the first communication interface on condition that the first processor has received the request signal from the information processing apparatus, and
   the information processing apparatus is configured to receive the result of detection from each of a plurality of balloon catheters, determine a condition for pressure application by the balloon catheter for each patient who is to undergo surgery based on an electronic medical chart of each of a plurality of patients and the result of detection, and give a notification about the determined condition for pressure application of each of the balloon catheters.

8. An information processing system comprising:
   a balloon catheter including a pipe path, a pressure sensor, a first processor, a first memory, and a first communication interface;
   an information processing apparatus including a second processor, a second memory, and a second communication interface; and
   a first server that manages a quantity of stock of the balloon catheter in a hospital, wherein
   the balloon catheter is configured such that the pressure sensor detects a state value including at least a pressure generated in the pipe path and the first processor stores a result of detection of the state value by the pressure sensor in the first memory,
   the information processing apparatus is configured such that the second processor transmits a prescribed request signal to the balloon catheter through the second communication interface,
   the first processor is further configured to transmit the result of detection stored in the first memory to the information processing apparatus through the first communication interface on condition that the first processor has received the request signal from the information processing apparatus,
   the information processing apparatus is configured to receive the result of detection from the balloon catheter, and
   the balloon catheter and the first server are configured such that when the balloon catheter detects the pressure equal to or higher than a predetermined threshold value, the balloon catheter transmits a predetermined signal to the first server, and the first server determines that the balloon catheter has been used, based on reception of the predetermined signal.

9. The information processing system according to claim 8, wherein
   the first server is configured to transmit information on the quantity of stock to a predetermined terminal apparatus, so that the terminal apparatus shows the information on the quantity of stock, when the quantity of stock of the balloon catheter in the hospital is equal to or smaller than a prescribed quantity.

10. The information processing system according to claim 8, further comprising a second server that manages a production schedule of the balloon catheter in a manufacturer that manufactures the balloon catheter, wherein
   the predetermined signal includes identification information of the balloon catheter where a pressure equal to or higher than the predetermined threshold value has been detected, and
   the second server is configured to receive the identification information from the first server and update the production schedule in the manufacturer of the balloon catheter based on the identification information.

11. An information processing system comprising:
a plurality of balloon catheters each including a pipe path and a memory; and
an information processing apparatus, wherein
the plurality of balloon catheters and the information processing apparatus are configured such that each of the plurality of balloon catheters detects a state value including at least a pressure generated in the pipe path, stores a result of detection of the state value in the memory, and outputs the stored result of detection to the information processing apparatus, and the information processing apparatus receives the result of detection from each of the plurality of balloon catheters, and
the information processing apparatus is configured to receive the result of detection from each of the plurality of balloon catheters, determine a condition for pressure application by each of the plurality of balloon catheters for each patient who is to undergo surgery based on an electronic medical chart of each of a plurality of patients and the result of detection, and give a notification about the determined condition for pressure application of each of the plurality of balloon catheters.

* * * * *